(12) United States Patent
Vock et al.

(10) Patent No.: US 7,620,520 B2
(45) Date of Patent: Nov. 17, 2009

(54) METHODS FOR DETERMINING WEIGHT OF A PERSON

(75) Inventors: Curtis A. Vock, Boulder, CO (US); Burl W. Amsbury, Boulder, CO (US); Eric R. Edstrom, Colorado Springs, CO (US); Robert Muir Holme, Boulder, CO (US); Paul Jonjak, Lafayette, CO (US); Adrian F. Larkin, Essex (GB); Perry Youngs, Longmont, CO (US)

(73) Assignee: PhatRat Technology, LLC, Lafayette, CO (US)

( * ) Notice: Subject to any disclaimer, the term of this patent is extended or adjusted under 35 U.S.C. 154(b) by 406 days.

(21) Appl. No.: 11/647,035

(22) Filed: Dec. 28, 2006

(65) Prior Publication Data

US 2007/0112542 A1 May 17, 2007

Related U.S. Application Data

(60) Division of application No. 11/358,508, filed on Feb. 21, 2006, now Pat. No. 7,171,331, which is a continuation of application No. 10/601,208, filed on Jun. 20, 2003, now Pat. No. 7,174,277, and a continuation of application No. 10/297,270, filed on Dec. 4, 2002, which is a continuation of application No. PCT/US01/51620, filed on Dec. 17, 2001.

(60) Provisional application No. 60/323,601, filed on Sep. 20, 2001, provisional application No. 60/285,032, filed on Apr. 19, 2001, provisional application No. 60/261,359, filed on Jan. 13, 2001, provisional application No. 60/259,271, filed on Dec. 29, 2000, provisional application No. 60/257,386, filed on Dec. 22, 2000, provisional application No. 60/256,069, filed on Dec. 15, 2000.

(51) Int. Cl.
*G06F 15/00* (2006.01)
(52) U.S. Cl. ............................ 702/173; 324/109
(58) Field of Classification Search ......... 702/149–152, 702/160, 188; 342/104–107, 109, 113, 357.06–357.17
See application file for complete search history.

(56) References Cited

U.S. PATENT DOCUMENTS 5,636,146 A  6/1997  Flentov et al.

(Continued)

FOREIGN PATENT DOCUMENTS

EP  9303265  *  6/1995

OTHER PUBLICATIONS

U.S. Appl. No. 11/646,768; Office Action; Oct. 29, 2007.

(Continued)

*Primary Examiner*—Edward Raymond
(74) *Attorney, Agent, or Firm*—Lathrop & Gage LLP

(57) ABSTRACT

A method for monitoring fractional weight supported by one foot of a person, comprising the steps of adhering a movement monitor device underneath the foot such that the device is compressed when weight is applied to the foot; generating wireless signals representative of a target fractional weight of a total weight of the person; remotely receiving the wireless signals as information of the fractional weight. A method of monitoring weight of a person, comprising the steps of arranging one or more weight sensitive detectors underneath a foot of the person; processing signals from the detectors to determine weight; and wirelessly communicating the weight to a remote receiver.

19 Claims, 45 Drawing Sheets

U.S. PATENT DOCUMENTS

| | | | |
|---|---|---|---|
| 5,673,691 | A | 10/1997 | Abrams et al. |
| 6,356,856 | B1 | 3/2002 | Damen et al. |
| 6,611,789 | B1 | 8/2003 | Darley |
| 2003/0065805 | A1 | 4/2003 | Barnes |

OTHER PUBLICATIONS

U.S. Appl. No. 11/646,768; Response to Office Action of Oct. 29, 2007; filed Dec. 31,2007.

U.S. Appl. No. 11/646,768; Notice of Allowance mailed Jan. 18, 2008.

Phatrat Technology, Inc. v. Timex Corporation, In the US District Court, District of Colorado, Case No. 06-CV-01447-MSK-BNB, Garmin International, Inc.'s Answer, Affirmative Defenses And Jury Deamdn To Phatrat Technology's Inc.'s First Amended Complaint And Counter Claims Against Plantiff, Sep. 26, 2006.

Phatrat Technology, Inc. v. Timex Corporation, In the US District Court, District of Colorado, Case No. 06-CV-01447-MSK-BNB, Answer, Affirmative Defenses, Counterclaims and Demand For Jury Trial; Sep. 26, 2006.

Phatrat Technology, Inc. v. Timex Corporation, In The US District Court, District Court, District of Colorado, Case No. 06-CV-01447,MSK-BNB, Disclosure Statement; Sep. 26, 2006.

Janssens, J.P., et al. "Columbus: A Novel Sensor System for Domestic Washing Machines", Jun. 2002, pp. 1-9.

U.S. Appl. No. 11/646,768, Response to Office Action mailed May 7, 2007.

U.S. Appl. No. 11/646,768, Office Action mailed May 7, 2007.

U.S. Appl. No. 1/358,508, Notice of Allowability Interview Summary mailed Oct. 18, 2006.

U.S. Appl. No. 11/358,508, Notice of Non Compliance Amendment mailed Sep. 12, 2006.

U.S. Appl. No. 11/358,508, Office Action mailed Aug. 14, 2006.

U.S. Appl. No. 11/358,508, Preliminary Amendment mailed Mar. 30, 2006.

U.S. Appl. No. 11/358,508, Preliminary Amendment mailed May 30, 2006.

U.S. Appl. No. 11/358,508, Preliminary Amendment mailed Jul. 26, 2006.

U.S. Appl. No. 11/358,508, Preliminary Amendment mailed Jul. 28, 2006.

U.S. Appl. No. 11/358,508, Response to Notice mailed Sep. 12, 2006.

U.S. Appl. No. 11/358,508, Response to Office Action mailed Aug. 16, 2006.

U.S. Appl. No. 11/358,508, Rule 312 Amendment mailed Oct. 24, 2006.

PCT/US01/51620 International Search Report mailed Sep. 25, 2002.

* cited by examiner

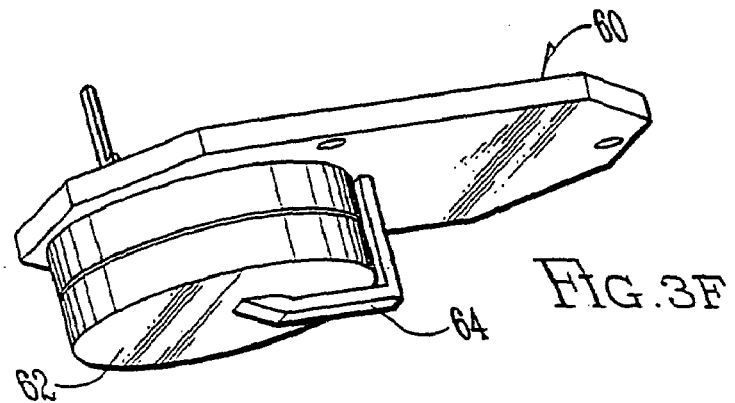
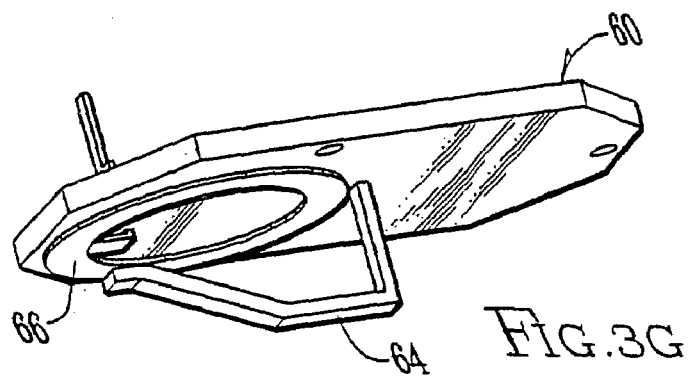
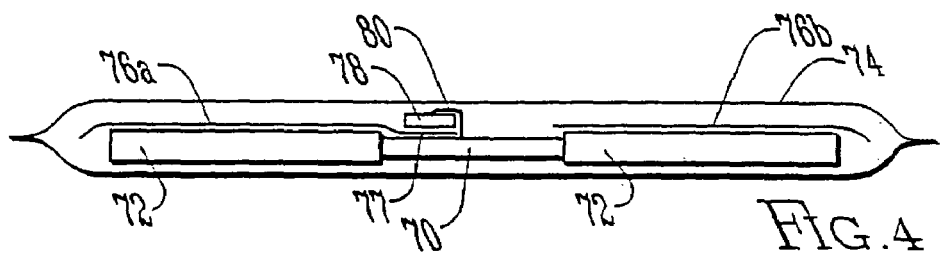
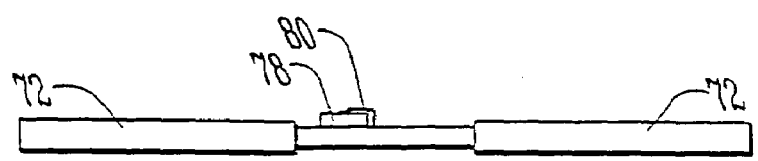

MAGNITUDE OF REPRESENTATIVE IMPACT

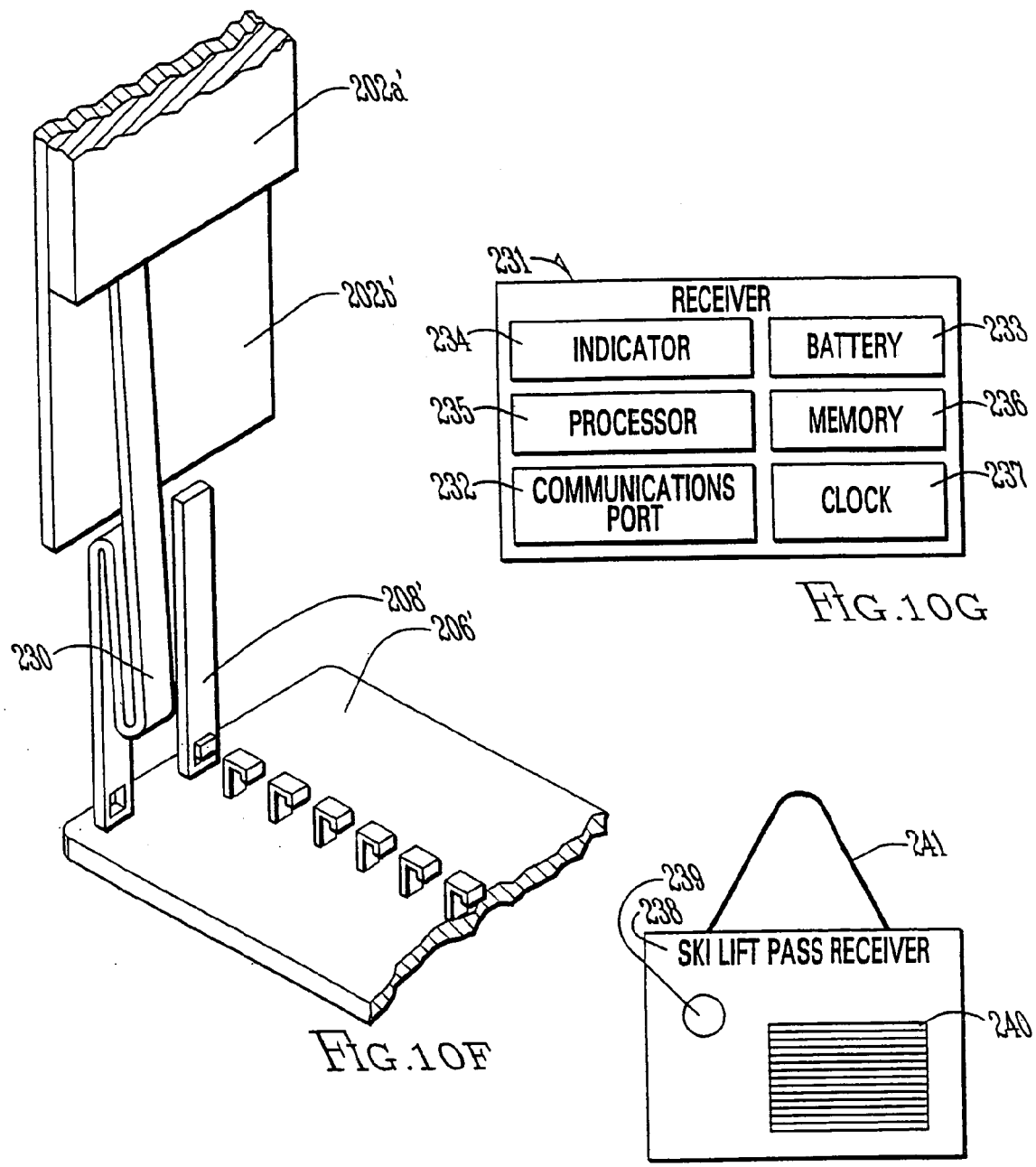
FIG.10G
FIG.10F
FIG.10H
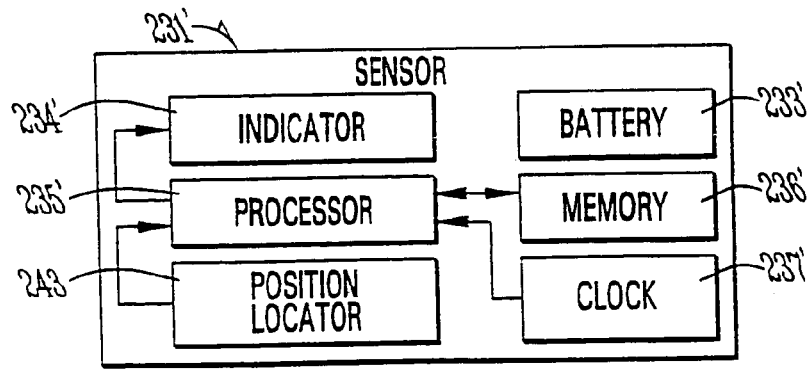
FIG.10I

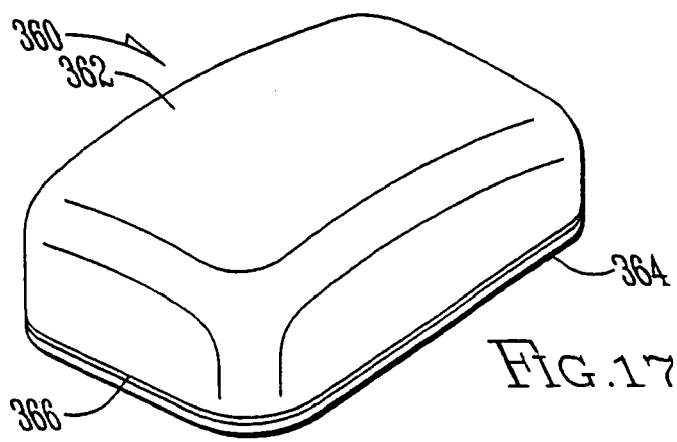
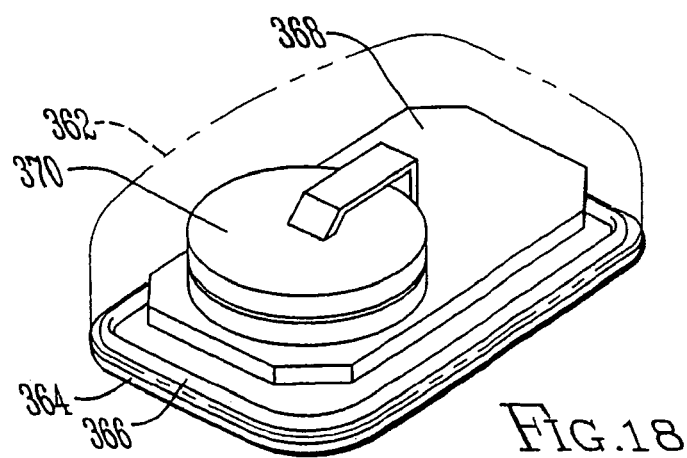
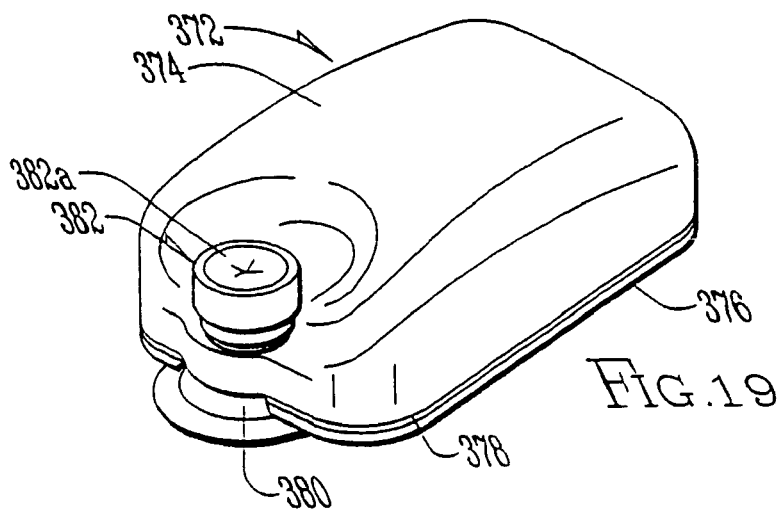

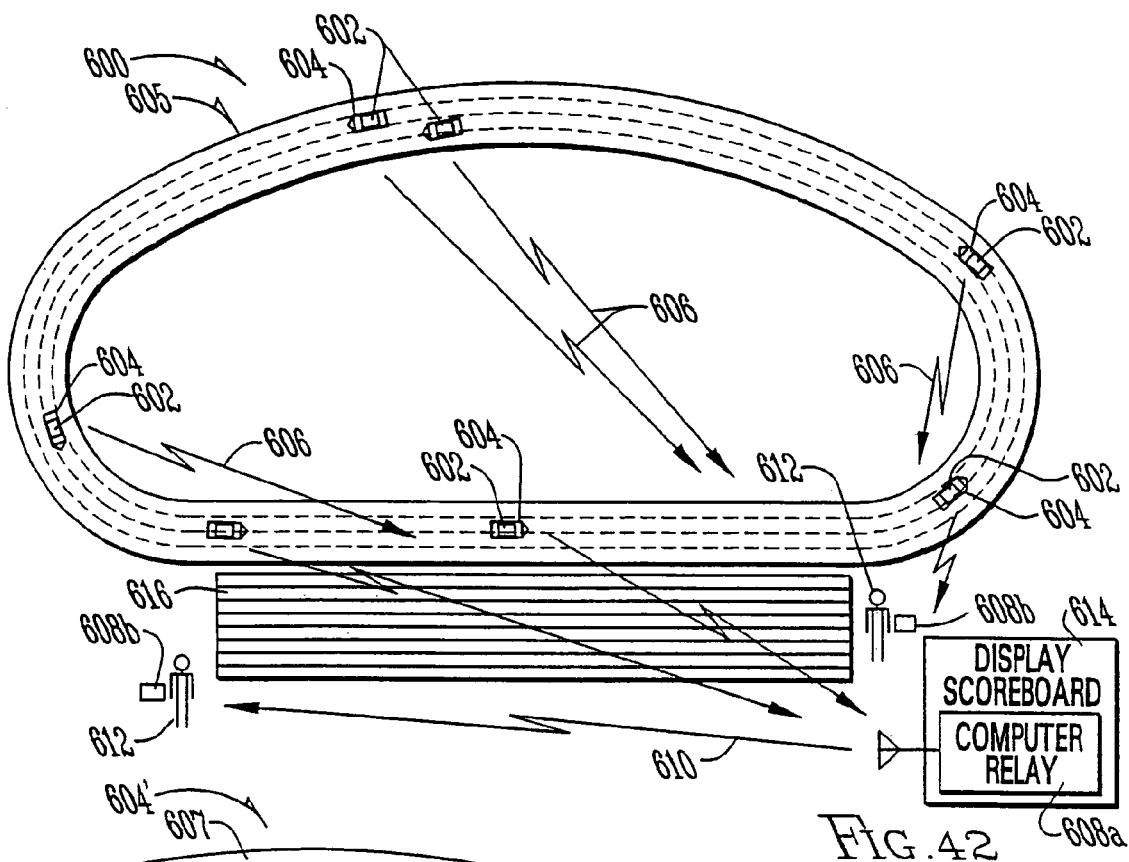
FIG. 42
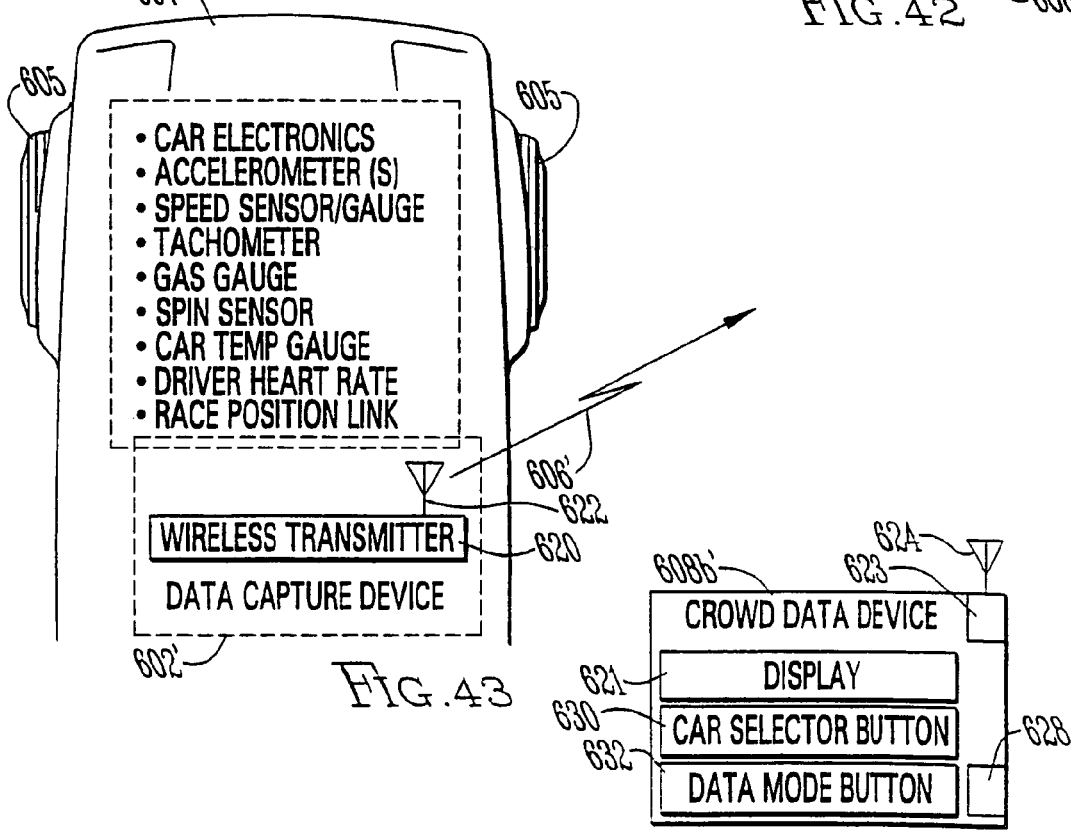
FIG. 43
FIG. 44

METHODS FOR DETERMINING WEIGHT OF A PERSON

This application is a divisional of application Ser. No. 11/358,508 filed Feb. 21, 2006 now U.S. Pat. No. 7,171,331, which is a continuation of application Ser. No. 10/601,208 filed Jun. 20, 2003 now U.S. Pat. No. 7,174,277 and a continuation of application Ser. No. 10/297,270 filed Dec. 4, 2002, which claims priority to PCT Application No. PCT/US01/51620, filed Dec. 17, 2001 and to the following six U.S. provisional applications: U.S. Provisional Application No. 60/256,069, filed Dec. 15, 2000; U.S. Provisional Application No. 60/257,386, filed Dec. 22, 2000; U.S. Provisional Application No. 60/259,271, filed Dec. 29, 2000; U.S. Provisional Application No. 60/261,359, filed Jan. 13, 2001; U.S. Provisional Application No. 60/285,032, filed Apr. 19, 2001; and U.S. Application No. 60/323,601, filed Sep. 20, 2001. The foregoing applications are expressly incorporated herein by reference.

FIELD OF THE INVENTION

The invention relates to sensing systems monitoring applications in sports, shipping, training, medicine, fitness, wellness and industrial production. The invention specifically relates to sensing and reporting events associated with movement, environmental factors such as temperature, health functions, fitness effects, and changing conditions.

BACKGROUND

The movement of objects and persons occurs continuously but is hardly quantified. Rather, typically only the result of the movement is known (i.e., object X moved from point A to point B; or, person Y ran to the store). Advances in technology have provided some quantification of movement. For example, GPS products now assist in determining the location of golf carts, vehicles and persons.

However, the detail of movement, minute to minute, second to second, is still not generally determinable in the prior art. For example, the movement of tangible objects typically involves (a) the shipment or carrying of goods and (b) electro-mechanical or motorized apparatus (e.g., planes, trains, automobiles, robots). The exact movements of such objects, and the conditions that they are subjected to, from point to point, are only qualitatively known. By way of example, a package is moved from location to location through delivery services like FEDERAL EXPRESS or UPS; however what occurred during transportation, and what transpired to the package, is anyone's guess. Occasionally, an object within the package is broken, indicating that the package experienced excessive abuse; but whose fault it is, or how or when it happened, are not known. What environments the package experienced is also not readily known.

The movement of persons, on the other hand, typically involves human-powered transportation, e.g., facilitated by biking, a wheelchair, or a motorized vehicle, e.g., a car. Body movement involved in transportation is subjected to many forces, some of which are dangerous. But the prior art does not provide for this knowledge; there is no effective way, currently, to efficiently quantify human movement. In sports, physical fitness, and training, precise information about movement would assist in many ways. By way of example, how effective a hand strike is in karate or boxing is, today, only qualitatively known. Quantitative feedback would be beneficial.

It is, accordingly, one feature of the invention to provide systems and methods addressing the afore-mentioned difficulties. A further feature of the invention is to provide methods and devices to quantify movement in a number of applications. Another feature of the invention is to monitor and report meaningful environment information such as temperature and humidity. These and other features will be apparent in the description that follows.

SUMMARY OF THE INVENTION

Movement Monitoring Devices

In one aspect, the invention provides a movement monitor device ("MMD") including an adhesive strip, a processor, a detector, and a communications port. In another aspect, two or more of the processor, port and detector are combined in a single application specific integrated circuit ("ASIC"). In one aspect the detector is an accelerometer, and preferably an accelerometer embedded into silicon within the ASIC. In other aspects, the detector is one of a strain gauge, force-sensing resistor, and piezoelectric strip. In still another aspect, the MMD includes a battery. In the preferred aspect of the invention, the MMD and battery are packaged in a protective wrapper. Preferably, the battery is packaged with the MMD in such a way that it does not "power" the MMD until the wrapper is removed. Preferably, the MMD includes a real time clock so that the MMD tags "events" (as hereinafter defined) with time and/or date information.

In yet another aspect, the MMD with adhesive strip collectively take a form similar to an adhesive bandage. More particularly, the adhesive strip of the invention is preferably like or similar to the adhesive of the adhesive bandage; and the processor (or protective wrapper) is embedded with the strip much the way the cotton is with the adhesive bandage. Preferably, a soft material (e.g., cotton or cloth) is included to surround the processor so as to (a) soften contact of rigid MMD components with a person and/or (b) protect the processor (and/or other components of the MMD). In still another aspect, the battery is also coupled with the soft material. In still another aspect, the processor and other elements of the MMD are combined into a single system-on-chip integrated circuit. A protective cover may surround the chip to protect the MMD from breakage.

In one aspect, one MMD of the invention takes a form similar to a smart label, with an adhesive substantially disposed with the label, e.g., on one side of the label. The adhesive strip of this MMD includes all or part of the back of the label with adhesive or glue permitting attachment of the label to other objects (or to a person).

In still another aspect, the MMD of the invention takes the form of a rigid monolithic that attaches to objects through one of known techniques. In this aspect, the device has a processor, communications port, and detector. A battery is typically included with the MMD. The MMD is attached to objects or persons by one of several techniques, including by glue or mechanical attachment (e.g., a pin or clip). An MMD of this aspect can for example exist in the form of a credit card, wherein the communications port is either a contact transponder or a contactless transponder. The MMD of one aspect includes a magnetic element that facilitates easily attaching the MMD to metal objects.

In operation, the MMD of the invention is typically interrogated by an interrogation device ("ID"). The MMD is responsive to the ID to communicate information within the MMD and, preferably, over secure communications protocols. By way of example, one MMD of the invention releases internal data only to an ID with the correct passwords and/or data protocols. The ID can take many forms, including a cell phone or other electronic device (e.g., a MP3 player, pager, watch, or PDA) providing communications with the MMD transmitter However, in another aspect, the MMD communicates externally to a remote receiver ("RR"). The RR listens for data from the MMD and collects that data for subsequent relay or use. In one aspect, the MMD's communications port is a one-way transmitter. Preferably, the MMD communicates data from the MMD to the RR either (a) upon the occurrence of an "event" or (b) in repeated time intervals, e.g., once every ten minutes. Alternatively, the MMD's communication port is a transceiver that handshakes with the RR to communicate data from the MMD to the RR. Accordingly, the MMD responds to data requests from the RR, in this aspect. In still another aspect, the RR radiates the MMD with transponder frequencies; and the MMD "reflects" movement data to the RR.

Accordingly, the communications port of one aspect is a transponder responsive to one or more frequencies to relay data back to an ID. By way of example, these frequencies can be one of 125 kHz and 13.56 MHz, the frequencies common with "contactless" RFID tags known in the art. In other aspects, communications frequencies are used with emission power and frequencies that fall within the permissible "unlicensed" emission spectrum of part 15 of FCC regulations, Title 47 of the Code of Federal Regulations. In particular, one desirable feature of the invention is to emit low power, to conserve battery power and to facilitate use of the MMD in various environments; and therefore an ID is placed close to the MMD to read the data. In other words, in one aspect, wireless communications from the MMD to the ID occurs over a short distance of a fraction of an inch to no more than a few feet. By way of example, as described herein, one ID of the invention takes the form of a cell phone, which communicates with the MMD via one or more secure communications techniques. Data acquired from the MMD is then communicated through cellular networks, if desired, to relay MMD data to end-users.

Or, in another aspect, the ID has a larger antenna to pick up weak transmission signals from a MMD at further distances separation.

In another aspect, the communications port is an infrared communications port. Such a port, in one aspect, communicates with the cell phone in secure communication protocols. In other aspects, an ID communicates with the infrared port to obtain the data within the MMD.

In yet another aspect, the communications port includes a transceiver. The MMD listens for interrogating signals from the RR and, in turn, relays movement "event" data from the MMD to the RR. Alternatively, the MMD relays movement "event" data at set time intervals or when the MMD accumulates data close to an internal storage limit. In one aspect, thereby, the MMD include internal memory; and the MMD stores one or more "event" data, preferably with time-tag information, in the memory. When the memory is nearly full, the MMD transmits the stored data wirelessly to a RR. Alternatively, stored data is transmitted to an IR when interrogated. In a third alternative, the MMD transmits stored data at set intervals, e.g., once per ½ hour or once per hour, to relay stored data to a RR. Other transmission protocols can be used without departing from the scope of the invention.

In still another aspect, data from the MMD is relayed to an ID through "contact" communication between the ID and the communications port. In one aspect, the MMD includes a small conductive plate (e.g., a gold plate) that contacts with the ID to facilitate data transfer. Smart cards from the manufacturer GEMPLUS may be used in such aspects of the invention.

In one aspect, the MMD includes a printed circuit board ("PCB"). A battery—e.g., a 2032 or 1025 Lithium coin cell—is also included, in another aspect of the invention. To make the device small, the PCB preferably has multilayers—and two of the internal layers have a substantial area of conducting material forming two terminals for the battery. Specifically, the PCB is pried apart at one edge, between the terminals, and the battery is inserted within the PCB making contact and providing voltage to the device. This advantageously removes then need for a separate and weighty battery holder.

In another aspect, the PCB has first and second terminals on either side of the PCB, and a first side of the battery couples to the first terminal, while a clip connects the second side of the battery to the second terminal, making the powered connection. This aspect advantageously removes the need for a separate and weighty battery holder.

In still another aspect, a terminal is imprinted on one side of the PCB, and a first side of the battery couples to that terminal. A conductive force terminal connects to the PCB and the second side of the battery, forming a circuit between the battery and the PCB.

By way of background for transponder technology, the following U.S. patents are incorporated herein by reference: U.S. Pat. No. 6,091,342 and U.S. Pat. No. 5,541,604.

By way of background for smart card and smart tag technology, the following U.S. patents are incorporated herein by reference: U.S. Pat. No. 6,151,647; U.S. Pat. No. 5,901,303; U.S. Pat. No. 5,767,503; U.S. Pat. No. 5,690,773; U.S. Pat. No. 5,671,525; U.S. Pat. No. 6,043,747; U.S. Pat. No. 5,977,877; and U.S. Pat. No. 5,745,037.

By way of background for adhesive bandages, the following U.S. patents are incorporated herein by reference: U.S. Pat. No. 5,045,035; U.S. Pat. No. 5,947,917; U.S. Pat. No. 5,633,070; U.S. Pat. No. 4,812,541; and U.S. Pat. No. 3,612,265.

By way of background for pressure and altitude sensing, the following U.S. patents are incorporated herein by reference: U.S. Pat. No. 5,178,016; U.S. Pat. No. 4,317,126; U.S. Pat. No. 4,813,272; U.S. Pat. No. 4,911,016; U.S. Pat. No. 4,694,694; U.S. Pat. No. 4,911,016; U.S. Pat. No. 3,958,459.

By way of background for rotation sensors, the following U.S. patents are incorporated herein by reference: U.S. Pat. No. 5,442,221; U.S. Pat. No. 6,089,098; and U.S. Pat. No. 5,339,699. Magnetorestrictive elements are further discussed in the following patents, also incorporated herein by reference: U.S. Pat. No. 5,983,724 and U.S. Pat. No. 5,621,316.

In accord with one aspect of the invention, the communications port is one of a transponder (including a smart tag or RFID tag), transceiver, or one-way transmitter. In other aspects, data from the MMD is communicated off-board (i.e., away from the MMD) by one of several techniques, including: streaming the data continuously off-board to get a real-time signature of data experienced by the MMD; transmission triggered by the occurrence of an "event" as defined herein; transmission triggered by interrogation, such as interrogation by an ID with a transponder; transmission staggered in "bursts" or "batches," such as when internal storage memory is full; and transmission at predetermined intervals of time, such as every minute or hour.

In one preferred aspect of the invention, the above-described MMDs are packaged like an adhesive bandage. Specifically, in one aspect, one or more protective strips rest over the adhesive portion of the device so as to protect the adhesive until the protective strips are removed. The strips are substantially stick-free so that they are easily removed from the adhesive prior to use. In another aspect, a "wrapper" is used to surround the MMD; the wrapper for example similar to wrappers of adhesive bandages. In accord with one preferred aspect, the battery electrically couples with the electronics of the MMD when the wrapper is opened and/or when the protective strips are removed. In this way, the MMD can be "single use" with the battery energizing the electronics only when the MMD is opened and applied to an object or person; the battery power being conserved prior to use by a decoupling element associated with the wrapper or protective strips. Those skilled in the art should appreciate that other techniques can be used without departing from the scope of the invention.

The MMDs of the invention are preferably used to detect movement "metrics," including one or more of airtime, speed, power, impact, drop distance, jarring and spin. WO9854581A2 is incorporated herein by reference as background to measuring speed, drop distance, jarring, impact and airtime. U.S. Pat. Nos. 6,157,898, 6,151,563, 6,148,271 and 6,073,086, relating to spin and speed measurement, are incorporated herein by reference. In one aspect, the detector and processor of the MMD collectively detect and determine "airtime," such as set forth in U.S. Pat. No. 5,960,380, incorporated herein by reference. By way of example, one detector is an accelerometer, and the processor analyzes acceleration data from the accelerometer as a spectrum of information and then detects the absence of acceleration data (typically in one or more frequency bands of the spectrum of information) to determine airtime. In another aspect, the detector and processor of the MMD collectively detect and determine drop distance. By way of example, one drop distance detector is a pressure sensor, and the processor analyzes data from the pressure sensor to determine changes in pressure indicating altitude variations (a) over a preselected time interval, (b) between a maximum and minimum altitude to assess overall vertical travel, and/or (c) between local minimums and maximums to determine jump distance. By way of a further example, a drop distance detector is an accelerometer, and the processor analyzes data from the accelerometer to determine distance, or changes in distance, in a direction perpendicular to ground, or perpendicular to forward movement, to determine drop distance.

In one preferred aspect, the accelerometer has "free fall" capability (e.g., with near zero hertz detection) to determine drop distance (or other metrics described herein) based, at least on part, on free fall physics. This aspect is for example useful in detecting dropping events of packages in shipment.

In another aspect, the detector and processor of the MMD collectively detect and determine spin. By way of example, one detector is a magnetorestrictive element ("MRE"), and the processor analyzes data from the MRE to determine spin (rotation per second, number of degrees, and/or degrees per second) based upon the MME's rotation through the earth's magnetic fields. By way of a further example, another detector is a rotational accelerometer, and the processor analyzes data from the rotational accelerometer to determine spin. In another aspect, the detector and processor of the MMD collectively detect and determine jarring, power and/or impact. By way of example, one detector is an accelerometer, and the processor analyzes data from the accelerometer to determine the jarring, impact and/or power. As used herein, jarring is a function a higher power of velocity in a direction approximately perpendicular to forward movement (typically in a direction perpendicular to ground, a road, or a floor). As used herein, power is an integral of filtered (and preferably rectified) acceleration over some preselected time interval, typically greater than about ½ second. As used herein, impact is an integral of filtered (and preferably rectified) acceleration over a time interval less than about ½ second. Impact is often defined as immediately following an "airtime" event (i.e., the "thump" of a landing).

In one aspect, the MMD continuously relays a movement metric by continuous transmission of data from the detector to a RR. In this way, a MMD attached to a person may beneficially track movement, in real time, of that person by recombination of the movement metrics at a remote computer. In one aspect, multiple MMDs attached to a person quantify movement of a plurality of body parts or movements, for example to assist in athletic training (e.g., for boxing or karate). In another aspect, multiple MMDs attached to an object quantify movement of a plurality of object parts or movements, for example to monitor or assess different components or sensitive parts of an object. For example, multiple MMDs can be attached to an expensive medical device to monitor various critical components during shipment; when the device arrives at the customer, these MMDs are interrogated to determine whether any of the critical components experienced undesirable conditions—e.g., a high impact or temperature or humidity.

By way of background for moisture sensing, the following U.S. patents are incorporated herein by reference: U.S. Pat. No. 5,486,815; U.S. Pat. No. 5,546,974; and U.S. Pat. No. 6,078,056.

By way of background for humidity sensing, the following U.S. patents are incorporated herein by reference: U.S. Pat. No. 5,608,374; U.S. Pat. No. 5,546,974; and U.S. Pat. No. 6,078,056.

By way of background for temperature sensing, the following U.S. patents are incorporated herein by reference: U.S. Pat. No. 6,074,089; U.S. Pat. No. 4,210,024; U.S. Pat. No. 4,516,865; U.S. Pat. No. 5,088,836; and U.S. Pat. No. 4,955,980.

In accord with further aspects of the invention, the MMD measures one or more of the following environmental metrics: temperature, humidity, moisture, altitude and pressure. These environmental metrics are combined into the MMD with a detector that facilitates the monitoring of movement metrics such as described above. For temperature, the detector of one aspect is a temperature sensor such as a thermocouple or thermister. For altitude, the detector of one aspect is an altimeter. For pressure, the detector of one aspect is a pressure sensor such as a surface mount semiconductor element made by SENSYM.

In accord with one aspect, a MMD monitors one or more movement metrics for "events," where data is acquired that exceeds some predetermined threshold or value. By way of example, in one aspect the detector is a triaxial accelerometer and the processor coupled to the accelerometer seeks to determine impact events that exceed a threshold, in any or all of three axes. In another aspect, a single axis accelerometer is used as the detector and a single axis is monitored for an impact event. In another example, the detector and processor collectively monitor and detect spin events, where for example it is determined that the device rotated more than 360 degrees in ½ second or less (an exemplary "event" threshold). In still another aspect, the detector is a force detector and the processor and detector collectively determine a change of weight of an object resting on the MMD over some preselected time period. In one specific object, the invention provides for a MMD to monitor human weight to report that weight, on demand, to individuals. Preferably, such a MMD is in a shoe.

In one aspect, the movement metric of rotation is measured by a MMD with a Hall effect detector. Specifically, one aspect of the Hall effect detector with a MMD of the invention monitors when the MMD is inverted. In one other aspect, the Hall effect detector is used with the processor to determine when an object is inverted or rotated through about 180 degrees. An "event" detected by this aspect can for example be one or more inversions of the MMD of about 180 degrees.

In still another aspect, the MMD has a MRE as the detector, and the MMD measures spin or rotation experienced by the MRE.

In one aspect, a plurality of MMDs are collated and packaged in a single container, preferably similar to the cans or boxes containing adhesive bandages. Preferably, in another aspect, MMDs of the invention are similarly programmed within the container. By way of example, one container carries 100 MMDs that each respond to an event of "10 g's." In another example, another container carries 200 MMDs that respond to an event of "100 g's." Packages of MMDs can be in any suitable number N greater than or equal to two; typically however MMDs are packaged together in groups of 50, 100, 150, 200, 250, 500 or 1000. A variety pack of MMDs are also provided, in another aspect, for example containing ten 5 g MMDs, ten 10 g MMDs, ten 15 g MMDs, ten 20 g MMDs, ten 25 g MMDs, ten 30 g MMDs, ten 35 g MMDs, ten 40 g MMDs, ten 45 g MMDs, and ten 50 g MMDs. Another variety package can for example include groups of MMDs spaced at 1 g or 10 g intervals.

In one preferred aspect, the MMD of the invention includes internal memory. Preferably the memory is within the processor or ASIC. Event data is stored in the memory, in accord with one aspect, until transmitted off-board. In this way, the MMD monitors and stores event data (e.g., an "event" occurrence where the MMD experiences 10 g's). Preferably, the event data is time tagged with data from a real-time clock; and thus a real time clock is included with the MMD (or made integral with the processor or ASIC). A crystal or other clocking mechanism may also be used.

In one aspect, the MMD is programmed with a time at the initial time of use (i.e., when the device is powered). In one other aspect, the MMD is packaged with power so that real time clock data is available when the product is used. In this aspect, therefore, a container of MMDs will typically have a "stale" date when the MMD's battery power is no longer usable. In one aspect, the MMD has a replaceable battery port so that a user can replace the battery.

The invention has certain advantages. A MMD of the invention can practically attach to almost anything to obtain movement information. By way of example, a MMD of the invention can attach to furniture to monitor shipping of furniture. If the furniture were dropped, an impact event occurs and is recorded within the MMD, or transmitted wirelessly, with an associated time tag. When the furniture is damaged prior to delivery, a reader (e.g., an ID) reads the MMD to determine when the damage occurred—leading to the responsible party who may then have to pay for the damage. In a further example, if furniture is rated to "10 g's", a MMD (programmed and enabled to detect 10 g events) is attached to the furniture when leaving the factory, so that any 10 g event before delivery is recorded and time-stamped, again leading to a responsible party. Similarly, in other aspects, devices of the invention are attached to packages (e.g., FED EX or UPS shipments) to monitor handling. By way of example, fragile objects may be rated to 5 g; and an appropriately programmed MMD of the invention is attached to the shipment to record and time-tag 5 g events. In another aspect, fragile objects that should be maintained at a particular orientation (i.e., packages shipped within "This Side Up" instructions) are monitored by a MMD detecting inversions of about 180 degrees, such as through a Hall Effect detector.

In one aspect, the MMD includes a tamper proof detector that ensures the MMD is not removed or tampered with once applied to an object or person, until an authorized person removes the MMD. In one aspect, the tamper proof detector is a piezoelectric strip coupled into or with the adhesive strip. Once the MMD is powered and applied to an object or person, a quiescent period ensues and the MMD continually monitors the tamper proof detector (in addition to the event detector) to record tampering activity. In the case of the piezoelectric strip, removal of the MMD from a person or object after the quiescent period provides a relatively large voltage spike, indicating removal. That spike is recorded and time stamped. If there are more than one such records (i.e., one record represents the final removal), then tampering may have occurred. Since date and time are tagged with the event data, the tamper time is determined, leading to identify the tampering person (i.e., the person responsible for the object when the tamper time was tagged).

In one aspect, the invention provides an ID in the form of a cell phone. Nearly one in three Americans use a cell phone. According to the teachings of the invention, data movement "metrics" are read from a MMD through the cell phone. Preferably, data communicated from the MMD to the cell phone is made only through secure communications protocols so that only authorized cell phones can access the MMD. In one specific aspect, MMD events are communicated to a cell phone or cellular network, and from that point are relayed to persons or additional computer networks for use at a remote location.

Miniature tension or compression load cells are used in certain aspects of the invention. By way of example, a MMD incorporating such cells are used in measuring and monitoring tension and/or compression between about fifty grams and 1000 lbs, depending upon the application. In one aspect, the MMD generates a warning signal when the load cell exceeds a preselected threshold.

In accord with the invention, several advantages are apparent. The following lists some of the non-limiting movement events monitored and captured by select MMDs of the invention, in accord to varied aspects of the invention:

- impact or "g's" experienced by the MMD that exceed a predetermined threshold, e.g., 10 or 50 g's
- accumulated or integrated rectified acceleration experienced by the MMD over a predetermined time interval
- rotations experienced by the MMD in increments of 90 degrees, such as 90, 180, 270, 360 degrees, or multiples thereof
- frequency-filtered, rectified, and low-pass filtered acceleration detecting impact events, by the MMD, exceeding thresholds such as 5, 10, 20, 25, 50 and 100 g's, preferably after an airtime event
- rotational velocities experienced by the MMD exceeding some preselected "degrees per second" or "revolutions per minute" threshold
- airtime events experienced by the MMD exceeding ¼, ⅓, or ½ second, or multiples thereof
- speed events experienced by the MMD exceeding miles per hour thresholds of 10, 20, 30, 40, 50, 60 mph (those skilled in the art should appreciate that other "speed" units can be used, e.g., km/hour, m/s or cm/s)
- drop distance events experienced by the MMD exceeding set distances such as 1, 2, 3, 4, 5, 10, 20, 50 and 100 feet (or inches, centimeters or meters)

altitude variation events between maximum and minimum values over a daily time interval jerk variations proportional to $V'''$ or $\partial'''V/\partial'''t$, where V is velocity in a direction perpendicular to movement along a surface (e.g., ground), where n is some integer greater than or equal to 2, and where t is time The above movement events may be combined for a variety of metrics useful to users of the invention. For example, in one aspect, altitude variations are used to accurately gauge caloric burn through the variations. Such information is particularly useful for mountain bikers and in mountain sports.

The invention of one aspect provides a quantizing accelerometer that detects one or more specific g-levels in a manner particularly useful as a detector in a MMD of the invention.

There are thus several applications of the invention, including the monitoring of movement for people, patients, packages, athletes, competitors, shipments, furniture, athletes in training (e.g., karate), and industrial robotics. The benefits derived by such monitoring can be used by insurance companies and manufacturers, which, for example, insure shipments and packages for safe delivery to purchasers. Media broadcasters, including Internet content providers, can also benefit by augmenting information associated with a sporting event (e.g., airtime of a snowboarder communicated in real time to the Internet, impact of a football or soccer ball during a game, boxing glove strike force during a fight, tennis racquet strike force during a match). The MMD of the invention is small, and may be attached to practically any object—so ease of use is clearly another advantage. By way of example, an MMD can be mounted to the helmet or body armor of each football player or motocross competitor to monitor movement and jerk of the athlete. In such applications, data from the MMD preferably transmits event data in real time to a RR in the form of a network, so that MMD data associated with each competitor is available for broadcast to a scoreboard, TV or the Internet. Other advantages should be apparent in the description within.

Event Monitoring Devices

The invention also provides certain sensors and devices used to monitor and report temperature, humidity, chemicals, heart rate, pulse, pressure, stress, weight, environmental factors and hazardous conditions.

In one aspect, the invention provides a event monitor device ("EMD") including an adhesive strip, a processor, a detector, and a communications port. In another aspect, two or more of the processor, port and detector are combined in a single application specific integrated circuit ("ASIC"). In one aspect the detector is an humidity or temperature sensor, and preferably that detector is embedded into silicon within the ASIC. In other aspects, the detector is one of an EKG sensing device, weight-sensing detector, and chemical detector. In still another aspect, the EMD includes a battery. In the preferred aspect of the invention, the EMD and battery are packaged in a protective wrapper. Preferably, the battery is packaged with the EMD in such a way that it does not "power" the EMD until the wrapper is removed. Preferably, the EMD includes a real time clock so that the EMD tags "events" with time and/or date information.

In yet another aspect, the EMD with adhesive strip collectively take a form similar to an adhesive bandage. More particularly, the adhesive strip of the invention is preferably like or similar to the adhesive of the adhesive bandage; and the processor is embedded with the strip much the way the cotton is with the adhesive bandage. Preferably, a soft material (e.g., cotton or cloth) is included to surround the processor so as to (a) soften contact of rigid EMD components with a person and/or (b) protect the processor (and/or other components of the EMD). In still another aspect, the battery is also coupled with the soft material. In still another aspect, the processor and other elements of the EMD are combined into a single system-on-chip integrated circuit. A protective cover may surround the chip to protect the EMD from breakage.

In one aspect, one EMD of the invention takes a form similar to a smart label, with an adhesive substantially disposed with the label, e.g., on one side of the label. The adhesive strip of this EMD includes all or part of the back of the label with adhesive or glue permitting attachment of the label to other objects (or to a person).

In still another aspect, the EMD of the invention takes the form of a rigid monolithic that attaches to objects through one of known techniques. In this aspect, the device has a processor, communications port, and detector. A battery is typically included with the EMD. The EMD is attached to objects or persons by one of several techniques, including by glue or mechanical attachment (e.g., a pin or clip). An EMD of this aspect can for example exist in the form of a credit card, wherein the communications port is either a contact transponder or a contactless transponder. The EMD of one aspect includes a magnetic element that facilitates easily attaching the EMD to metal objects.

In operation, the EMD of the invention is typically interrogated by an ID. The EMD is responsive to the ID to communicate information within the EMD and, preferably, over secure communications protocols. By way of example, one EMD of the invention releases internal data only to an ID with the correct passwords and/or data protocols. The ID can take many forms, including a cell phone or other electronic device (e.g., a MP3 player, pager, watch, or PDA) providing communications with the EMD transmitter However, in another aspect, the EMD communicates externally to a RR. The RR listens for data from the EMD and collects that data for subsequent relay or use. In one aspect, the EMD's communications port is a one-way transmitter. Preferably, the EMD communicates data from the EMD to the RR either (a) upon the occurrence of an "event" or (b) in repeated time intervals, e.g., once every minute or more. Alternatively, the EMD's communication port is a transceiver that handshakes with the RR to communicate data from the EMD to the RR. Accordingly, the EMD responds to data requests from the RR, in this aspect. In still another aspect, the RR radiates the EMD with transponder frequencies; and the EMD "reflects" the data to the RR.

Accordingly, the communications port of one EMD is a transponder responsive to one or more frequencies to relay data back to an ID. By way of example, these frequencies can be one of 125 kHz and 13.56 MHz, the frequencies common with "contactless" RFID tags known in the art. In other aspects, communications frequencies are used with emission power and frequencies that fall within the permissible "unlicensed" emission spectrum of part 15 of FCC regulations, Title 47 of the Code of Federal Regulations. In particular, one desirable feature of the invention is to emit low power, to conserve battery power and to facilitate use of the EMD in various environments; and therefore an ID is placed close to the EMD to read the data. In other words, in one aspect, wireless communications from the EMD to the ID occurs over a short distance of a fraction of an inch to no more than a few feet. By way of example, as described herein, one ID of the invention takes the form of a cell phone, which communicates with the EMD via one or more secure communications techniques. Data acquired from the EMD is then communicated through cellular networks, if desired, to relay EMD data to end-users. Or, in another aspect, or sensitive or directional antenna is used to increase the distance to detect data of the EMD.

In another aspect, the communications port is an infrared communications port. Such a port, in one aspect, communicates with the cell phone in secure communication protocols. In other aspects, an ID communicates with the infrared port to obtain the data within the EMD.

In yet another aspect, the communications port includes a transceiver. The EMD listens for interrogating signals from the RR and, in turn, relays "event" data from the EMD to the RR. Alternatively, the EMD relays "event" data at set time intervals or when the EMD accumulates data close to an internal storage limit. In one aspect, thereby, the EMD include internal memory; and the EMD stores one or more "event" data, preferably with time-tag information, in the memory. When the memory is nearly full, the EMD transmits the stored data wirelessly to a RR. Alternatively, stored data is transmitted to an IR when interrogated. In a third alternative, the EMD transmits stored data at set intervals, e.g., once per ½ hour or once per hour, to relay stored data to a RR. Other transmission protocols can be used without departing from the scope of the invention.

In still another aspect, data from the EMD is relayed to an ID through "contact" communication between the ID and the communications port. In one aspect, the EMD includes a small conductive plate (e.g., a gold plate) that contacts with the ID to facilitate data transfer. Smart cards from the manufacturer GEMPLUS may be used in such aspects of the invention.

In one aspect, the EMD includes a printed circuit board "PCB"). A battery—e.g., a 2032 or 1025 Lithium coin cell— is also included, in another aspect of the invention. To make the device small, the PCB preferably has multilayers—and two of the internal layers have a substantial area of conducting material forming two terminals for the battery. Specifically, the PCB is pried apart at one edge, between the terminals, and the battery is inserted within the PCB making contact and providing voltage to the device. This advantageously removes then need for a separate and weighty battery holder. Flex circuit boards may also be used.

In another aspect, the PCB has first and second terminals on either side of the PCB, and a first side of the battery couples to the first terminal, while a clip connects the second side of the battery to the second terminal, making the powered connection. This aspect advantageously removes then need for a separate and weighty battery holder.

In still another aspect, a terminal is imprinted on one side of the PCB, and a first side of the battery couples to that terminal. A conductive force terminal connects to the PCB and the second side of the batter, forming a circuit between the battery and the PCB.

In accord with one aspect of the invention, the communications port is one of a transponder (including a smart tag or RFID tag), transceiver, or one-way transmitter. In other aspects, data from the EMD is communicated off-board (i.e., away from the EMD) by one of several techniques, including: streaming the data continuously off-board to get a real-time signature of data experienced by the EMD; transmission triggered by the occurrence of an "event" as defined herein; transmission triggered by interrogation, such as interrogation by an ID with a transponder; transmission staggered in "bursts" or "batches," such as when internal storage memory is full; and transmission at predetermined intervals of time, such as every minute or hour.

In one preferred aspect of the invention, the above-described EMDs are packaged like an adhesive bandage. Specifically, in one aspect, one or more protective strips rest over the adhesive portion of the device so as to protect the adhesive until the protective strips are removed. The strips are substantially stick-free so that they are easily removed from the adhesive prior to use. In another aspect, a "wrapper" is used to surround the EMD; the wrapper being similar to existing wrappers of adhesive bandages. In accord with one preferred aspect, the battery electrically couples with the electronics of the EMD when the wrapper is opened and/or when the protective strips are removed. In this way, the EMD can be "single use" with the battery energizing the electronics only when the EMD is opened and applied to an object or person; the battery power being conserved prior to use by a decoupling element associated with the wrapper or protective strips. Those skilled in the art should appreciate that other techniques can be used without departing from the scope of the invention.

In one aspect, the EMD continuously relays an environmental metric (e.g., temperature, humidity, or chemical content) by continuous transmission of data from the detector to a RR. In this way, a EMD attached to a person or object may beneficially track conditions, in real time, of that person or object by recombination of the environmental metrics at a remote computer. In one aspect, multiple EMDs attached to a person or object quantify data for a plurality of locations, for example to monitor sub-parts of an object or person.

In accord with further aspects of the invention, the EMD measures one or more of the following environmental metrics: temperature, humidity, moisture, altitude and pressure. For temperature, the detector of one aspect is a temperature sensor such as a thermocouple or thermister. For altitude, the detector of one aspect is an altimeter. For pressure, the detector of one aspect is a pressure sensor such as a surface mount semiconductor element made by SENSYM.

In accord with one aspect, an EMD monitors one or more metrics for "events," where data is acquired that exceeds some predetermined threshold or value. By way of example, in one aspect the detector is a temperature sensor and the processor coupled to the temperature sensor seeks to determine temperature events that exceed a threshold. In another aspect, a humidity sensor is used as the detector and this sensor is monitored for a humidity event (e.g., did the EMD experience 98% humidity conditions). In another example, the detector and processor collectively monitor stress events, where for example it is determined that the EMD attached to a human senses increased heart rate of over 180 beats per minute (an exemplary "event" threshold). In still another aspect, the detector is a chemical (or pH) detector and the processor and detector collectively determine a change of chemical composition of an object connected with the EMD over some preselected time period.

In one aspect, a plurality of EMDs are collated and packaged in a single container, preferably similar to the cans or boxes containing adhesive bandages. Preferably, in another aspect, EMDs of the invention are similarly programmed within the container. By way of example, one container carries 100 EMDs that each respond to an event of "5 degrees" variation from some reference temperature. In another example, another container carries 200 EMDs that respond to an event of "90 degrees" change absolute. Temperature sensors may be programmed to determine actual temperatures, e.g., 65 degrees, or changes in temperature from some reference point, e.g., 10 degrees from reference.

Packages of EMDs can be in any suitable number N greater than or equal to two; typically however EMDs are packaged together in groups of 50, 100, 150, 200, 250, 500 or 1000.

In one preferred aspect, the EMD of the invention includes internal memory. Preferably the memory is within the processor or ASIC. Event data is stored in the memory, in accord with one aspect, until transmitted off-board. In this way, the EMD monitors and stores event data (e.g., an "event" occurrence where the EMD experiences 100 degree temperatures). Preferably, the event data is time tagged with data from a real-time clock; and thus a real time clock is included with the EMD (or made integral with the processor or ASIC). In one aspect, the EMD is programmed with a time at the initial time of use (i.e., when the device is powered). In one other aspect, the EMD is packaged with power so that real time clock data is available when the product is used. In this aspect, therefore, a container of EMDs will typically have a "stale" date when the EMD's battery power is no longer usable. In one aspect, the EMD has a replaceable battery port so that a user can replace the battery.

The invention has certain advantages. An EMD of the invention can practically attach to almost anything to obtain event information. By way of example, an EMD of the invention can attach to patients to track health and conditions in real time and with remote monitoring capability.

In one aspect, the EMD includes a tamper proof detector that ensures the EMD is not removed or tampered with once applied to an object or person, until an authorized person removes the EMD. In one aspect, the tamper proof detector is a piezoelectric strip coupled into or with the adhesive strip. Once the EMD is powered and applied to an object or person, a quiescent period ensues and the EMD continually monitors the tamper proof detector (in addition to the event detector) to record tampering activity. In the case of the piezoelectric strip, removal of the EMD from a person or object after the quiescent period provides a relatively large voltage spike, indicating removal. That spike is recorded and time stamped. If there are more than one such records (i.e., one record represents the final removal), then tampering may have occurred. Since date and time are tagged with the event data, the tamper time is determined, leading to identify the tampering person (i.e., the person responsible for the object when the tamper time was tagged).

In one aspect, the invention provides an ID in the form of a cell phone. Nearly one in three Americans use a cell phone. According to the teachings of the invention, data event "metrics" are read from an EMD through the cell phone. Preferably, data communicated from the EMD to the cell phone is made only through secure communications protocols so that only authorized cell phones can access the EMD. In one specific aspect, EMD events are communicated to a cell phone or cellular network, and from that point are relayed to persons or additional computer networks for use at a remote location.

In accord with the invention, several advantages are apparent. The following lists some of the non-limiting events monitored and captured by select EMDs of the invention, in accord to varied aspects of the invention:

absolute or relative temperatures heart rate or other fitness characteristics stress characteristics humidity or relative humidity fitness or patient health characteristics The invention will next be described in connection with preferred embodiments. In addition to those described above, certain advantages should be apparent in the description which follows.

BRIEF DESCRIPTION OF THE DRAWINGS

FIG. 3F shows one battery attachment mechanism, including batteries, for use with a monitor device of the invention;

FIG. 3G shows the mechanism of FIG. 3F without the batteries;

FIGS. 4 and 4A illustrate one technique for powering a monitor device, in accord with the invention;

FIG. 10F illustrates imparting time-tag information to a sensor through a canister such as in FIG. 10;

FIG. 10G shows one receiver constructed according to the invention;

FIG. 10H shows one receiver in the form of a ski lift ticket constructed according to the invention;

FIG. 10I shows one ticket sensor constructed according to the invention;

FIG. 17 shows a perspective view of one sensor housing constructed according to the invention, for use with a sensor such as a monitor device;

FIG. 18 illustrates a sensor, such as a MMD, within the housing of FIG. 17;

FIG. 19 shows a top perspective view of another housing constructed according to the invention, for use with a sensor such as a MMD and for mounting to a vehicle;

FIG. 42 shows one race-car monitoring system constructed according to the invention;

FIG. 43 shows one data capture device for operation with a racecar in a race monitoring system such as shown in FIG. 42;

FIG. 44 shows one crowd data device for operation with spectators in a race monitoring system such as shown in FIG. 42;

DETAILED DESCRIPTION OF PREFERRED EMBODIMENTS

Figure 1:
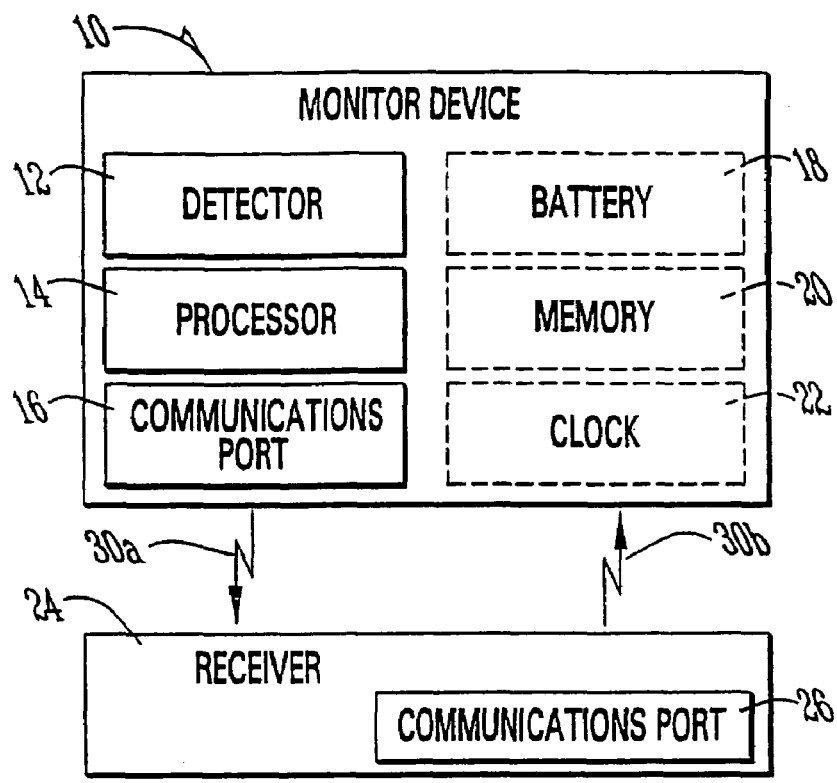
FIG. 1 shows a monitor device (e.g., a "MMD" or "EMD") and receiver (ID or RR) constructed according to the invention.

FIG. 1 shows a monitor device 10 constructed according to the invention. Device 10 can for example operate as a MMD or EMD described above. Device 10 includes a detector 12, processor 14, communications port 16, and battery 18. Preferably, device 10 also includes solid-state memory 20. Memory 20 can be integral with processor 14 (or other element of device 10, including port 16), or a stand-alone element within device 10. As a MMD, for example, detector 12 senses movement experienced by device 10 and generates signals indicative of that movement. Processor 12 then processes the signals to extract desired movement metrics, as described herein. Typically, when the movement metrics exceed a predetermined threshold, processor 12 stores data as an "event" within memory 20. Events are also preferably tagged with time information, typically date and time, as provided by clock 22.

As an EMD, for example, detector 12 senses temperature experienced by device 10 and generates signals indicative of temperature (either absolute, or relative). Processor 12 then processes the signals to extract desired data. Preferably, data such as temperature are time tagged with date and/or time information so that a limited recording is made of environmental conditions.

Communications port 16 communicates event data from device 10 to a receiver 24 as wireless data 30a. Port 16 typically performs such communications in response to commands from processor 14. Communications port 26 receives wireless data 30a for use within receiver 24. If desired, communications port 26 can also communicate with port 16 to transmit wireless data 30b to device 10. In such an embodiment, ports 16, 26 are preferably radio-frequency, infrared or magnetically-inductive transceivers. Alternatively, port 26 is a transmitter that interrogates device 10; and port 16 is a transponder that reflects event data to receiver 24. In one preferred embodiment, receiver 24 is part of the circuitry and packaging of a cell phone, which relays events (e.g., a movement event) to a remote storage facility. In other embodiments, receiver 24 is part of the circuitry and packaging of a MP3 player, pager, watch, or electronic PDA. Receiver 24 may connect with headphones (not shown) to provide information to a user and corresponding to "event" data.

Data communication between device 10 and receiver 24 is preferably "secure" so that only a receiver with the correct identification codes can interrogate and access data from device 10. In such a mode, receiver 24 is an interrogation device ("ID"); and wireless communications 30a, 30b between ports 16, 26 can be through one of several electromagnetic communications spectrums, including radio-frequencies, microwave frequencies, ultrasound or infrared. However, communications between device 10 and receiver 24 can also be one way, e.g., wireless data 30a from device 10 to receiver 24; and in such an embodiment receiver 24 preferably understands the communications protocols of data 30a to correctly interpret the data from device 10. Receiver 24 in this embodiment "listens" for data transmitted from device 10. Receiver 24 thus may function as a remote receiver ("RR") stationed some distance (e.g., tens or hundreds of feet or more) from device 10.

Figure 1A:
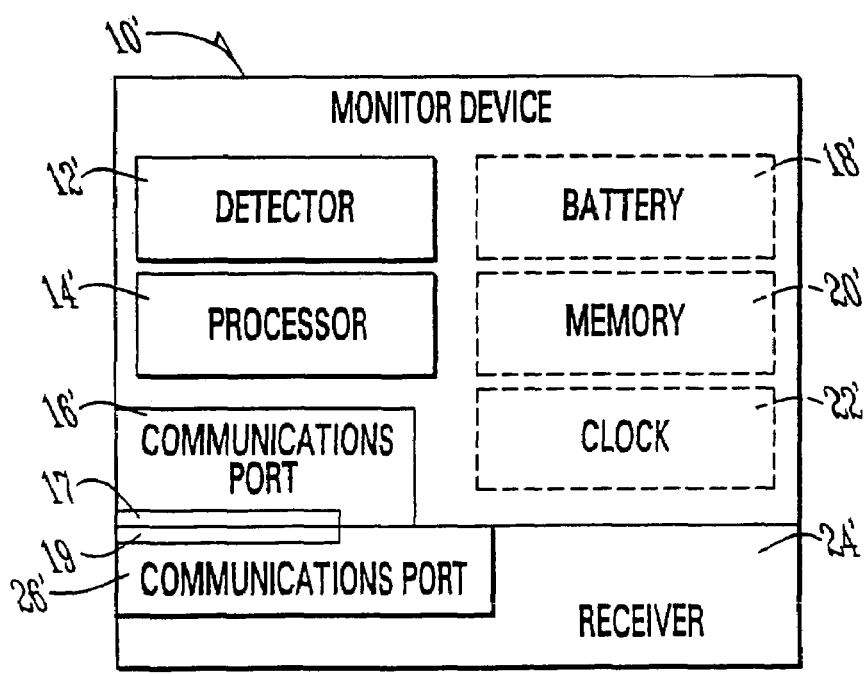
FIG. 1A shows an alternative monitor device of the invention, and in data communication with a receiver via "contact" transponder technology.

FIG. 1A shows an alternative communication scheme between device 10' and receiver 24'. Like numbered items in FIG. 1A have like functions as in FIG. 1; except that in FIG. 1A, ports 16', 26' function to transfer data from device 10' to receiver 24' as a "contact" transponder. Device 10' and receiver 24' are separate elements, though they appear immediately adjacent. A conductive pad 17 with port 16' facilitates communication with port 26' via its conductive pad 19. Accordingly, event data from device 10' transfers data to receiver 24' without "wireless" data 30 (FIG. 1), but rather through the circuit formed between device 10' and receiver 24' when contact is made between pads 17, 19, as shown in FIG. 1A.

Figure 2:
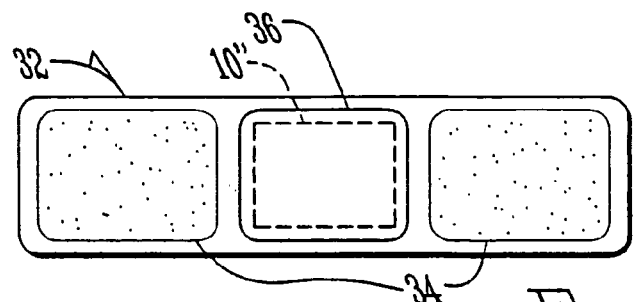
FIG. 2 shows a front view of one monitor device of the invention and formed with an adhesive strip and padding to soften physical connection to persons or objects.

A monitor device 10, 10' of the invention preferably includes an adhesive strip that provides for convenient attachment of the device to an object or person. As shown in FIG. 2, one such device 10" is shown coupled to adhesive strip 32 for just this purpose. Strip 32 is preferably flexible so as to bend and attach device 10" to nearly any surface shape. Strip 32 includes an adhesive 34 that bonds strip 32 to a person or object, such that device 10" attaches to that person or object in a substantially fixed location. FIG. 2 also shows that device 10" preferably resides adjacent to padding 36, to protect device 10" from physical harm and to provide a cushion interface between device 10" and a person or object. Padding 36 can for example be cotton or other soft material; and padding 36 can be made from soft material typically found with adhesive bandages of the prior art. Device 10" preferably includes a protective housing 11 (FIG. 2A) surrounding integrated circuits to protect the circuits from breakage.

Figure 2A:
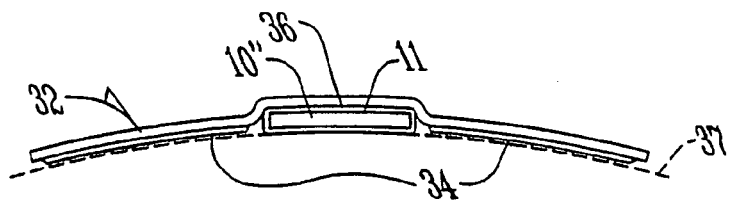
FIG. 2A shows a cross-sectional top view of the monitor device and strip of FIG. 2.

FIG. 2A shows a top cross-sectional view of monitor device 10" and strip 32. As illustrated, strip 32 is a flexible such that it can conform to a surface (e.g., curved surface 37) for attachment thereto. Adhesive 34 is shown covering substantially all of the back of strip 32 to provide for complete attachment to surface 37. Though padding 36 is not required, it preferably encapsulates device 10" to provide for optimum protection for device 10" when attached to surface 37. Note that padding 36 also protects surface 37 from scratching by any rigid elements of device 10" (e.g., battery 18, FIG. 1). Those skilled in the art should appreciate that padding 36 can be formed partially about device 10" to achieve similar goals and without departing from the scope of the invention; for example, padding 36 can reside adjacent only one side of device 10".

Those skilled in the art should appreciate that two or more of elements 14, 16, 18, 22 (FIG. 1) can be, and preferably are, integrated within an ASIC. Further, in one preferred embodiment, the detector 12 is also integrated within the ASIC as a solid-state accelerometer (e.g., using MEM technology). However, detector 12 can be a stand-alone element such as a piezoelectric strip, strain gauge, force-sensing resistor, weight sensor, temperature sensor, humidity sensor, chemical sensor, or heart rate detector.

Figure 2B:
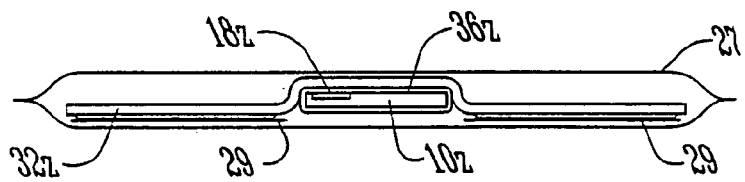
FIG. 2B shows a cross-sectional top view of one monitor device of the invention integrated with (a) a battery and (b) protective non-stick strips over the adhesive strip, all enclosed within a protective wrapper.
Figure 2C:
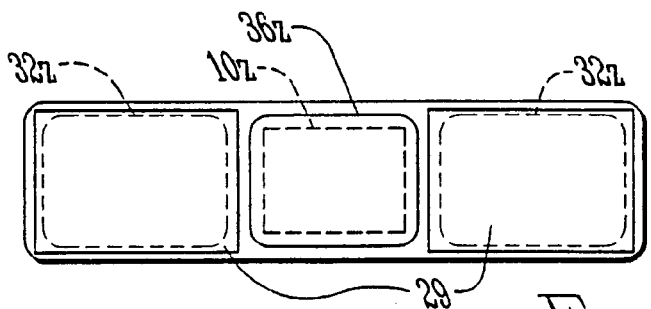
FIG. 2C shows a front view of the monitor device of FIG. 2B, without a protective wrapper.

FIG. 2B shows one monitor device 10z, with battery 18z, coupled within a protective wrapper 27. Protective non-stick strips 29 are also shown to cover adhesive (e.g., adhesive 34, FIG. 2) on adhesive strips 32z until device 10z is operatively used and applied to a person or object. Preferably, wrapper 27 and non-stick strips 29 are similar in design to the wrapper and strips of a common adhesive bandage. Accordingly, users of device 10z intuitively know how to open and attach device 10z to an object or surface (e.g., surface 37, FIG. 2A)—by opening wrapper 27, removing device 10z by pulling adhesive strip 32z from wrapper 27, and then removing non-stick strips 29 so that adhesive strips 32z are exposed for application to the object or surface. FIG. 2C illustrates device 10z in a back view with wrapper 27 removed, showing fuller detail of non-stick strips 29 covering and protecting the underlying adhesive (e.g., adhesive 34, FIG. 2) on strip 32z.

Figure 2D:
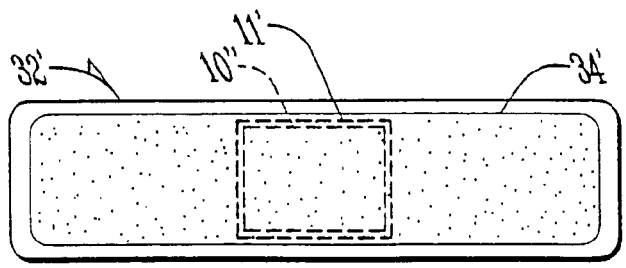
FIG. 2D shows an alternative monitor device of the invention and integrated directly with the adhesive strip to ensure detector contact.

A device 10 can also integrate directly with the adhesive strip, as shown in FIG. 2D. Specifically, device 10" of FIG. 2D couples directly with adhesive strip 32'. In addition, there is no padding with device 10"—as in certain circumstances it is desirable to have optimal fixation between device 10" and strip 32'. A housing 11' preferably protects device 10" from breakage. In one example, when the detector of device 10" is an accelerometer, direct coupling between device 10" and strip 32' provides for more accurate data capture of accelerations of the object to which strip 32' is adhered. As such, adhesive 34' preferably extends across the whole width of strip 32', as shown, such that device 10" is tightly coupled to the object adhered to by strip 32'.

Figure 2E:
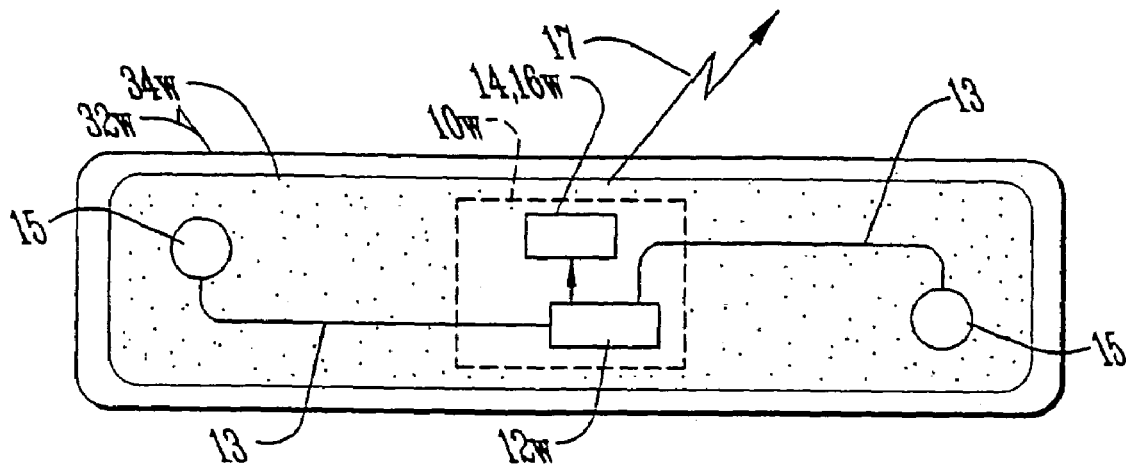
FIG. 2E shows one monitor device of the invention used to detect and/or track heart rate, in accord with the invention.

FIG. 2E shows one heart-rate monitor 10w constructed according to the invention. Like device 10, 10", device 10w preferably couples directly with an adhesive strip 32w with adhesive 34w. Monitor 10w includes a heart rate detector 12w that may for example detect EKG signals. By way of background, the following heart rate monitoring patents are incorporated herein by reference: U.S. Pat. No. 4,625,733; U.S. Pat. No. 5,243,993; U.S. Pat. No. 5,690,119; U.S. Pat. No. 5,738,104; U.S. Pat. No. 6,018,677; U.S. Pat. No. 3,807,388; U.S. Pat. No. 4,195,642; and U.S. Pat. No. 4,248,244. Two electrodes 15 electrically coupled to detector 12w with monitor 10w via conductive paths 13. Electrodes 5 couple with human skin when adhesive strip 32w is applied to the skin such that electro-magnetic pulses from the heart are detected by detector 12w. By way of example, detector 12w of one embodiment detects potential differences between electrodes 15 to determine heart rate. Once heart rate is detected, information is passed to other sections to process and/or retransmit the data as wireless data 17 to a remote receiver. For example, data from detector 12w may be transmitted to processor and/or communications port 14w, 16w; from there, data may be relayed off-board. In one embodiment, wireless data 17 is a signal indicative of the existence of heart rate—so that monitor 10w may be used in patient safety to warn of patient heart failure (i.e., the absence of a heart rate may mean that a patient went into cardiac arrest). In another embodiment, wireless data 17 is a signal indicative of actual heart rate, e.g., 100 beats per minute, such that monitor 10w may be used in fitness applications. Monitor 10w thus provides an alternative to "strap" heart rate monitors; users of the invention stick on monitor 10w via adhesive strip 32w to monitor heart rate in real time. Data 17 may be captured by a receiver such as a watch to display the data to the wearing user. Monitor 10w can also be used in patient monitoring applications, such as in hospitals, so that patient health is monitored remotely and efficiently. By way of example, a monitor 10w may be attached to each critical care patient so that a facility (e.g., a hospital) can monitor each patient at a single monitoring location (i.e., at the location receiving signals 17).

As an alternative heart rate monitor, device 10 of FIG. 1 has a detector in the form of a microphone. Processor 12 then processes microphone detector data to "listen" for breathing sounds to report breathing—or not breathing—as a health metric.

Figure 3:
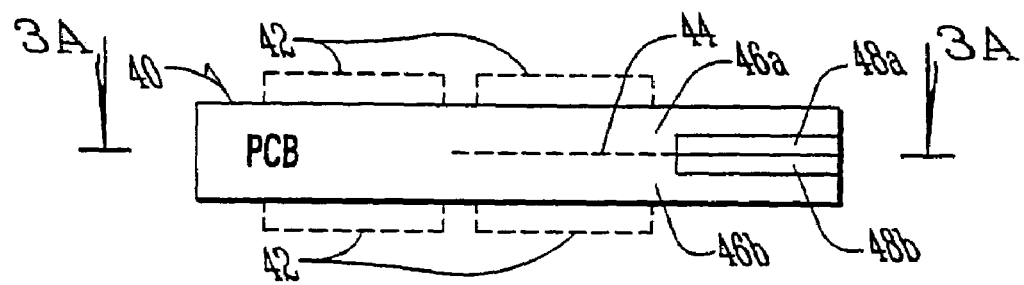
FIG. 3 shows a cross-sectional view (not to scale) of one monitor device of the invention for integrating a battery with a printed circuit board.
Figure 3A:
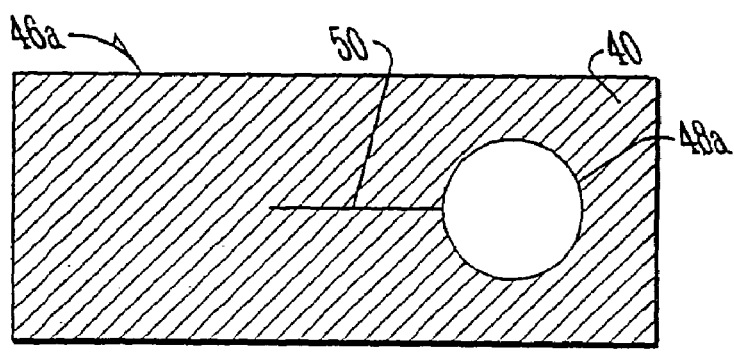
FIG. 3A is a cross-sectional top view of part of the monitor device of FIG. 3.
Figure 3B:
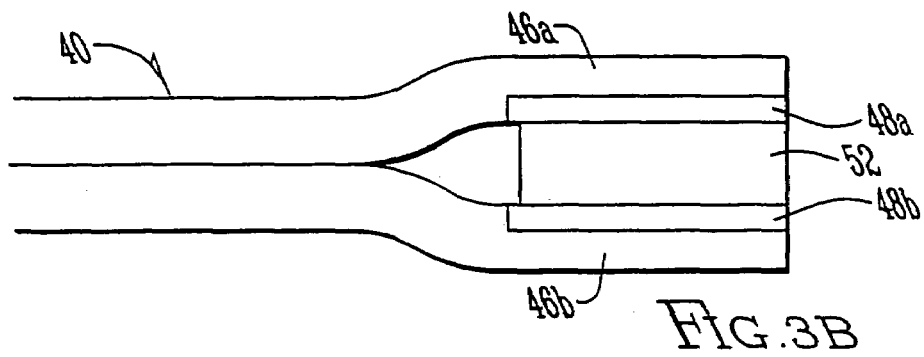
FIG. 3B shows an operational view of the monitor device of FIG. 3, with a battery inserted between layers of the printed circuit board.

The invention also provides for efficiently integrating battery 18 with a monitor device. FIG. 3 illustrates one technique, wherein the monitor device (e.g., device 10) includes a printed circuit board ("PCB") 40 that forms the back-plane forming the electrical interconnectivity with elements 42 (elements 42 can for example be any of items 12, 14, 16, 20, 22, FIG. 1). PCB 40 of FIG. 3 is a multi-layer board, as illustrated by layer line 44. Between two layers 46a, 46b, PCB 40 is manufactured with two opposing terminals 48a, 48b. Terminals 48a, 48b can for example be copper tracks in PCB 40, or copper with gold flash to facilitate good electrical connection. FIG. 3A shows a top view of one terminal 48a with layer 46a, illustrating that terminal 48a is typically larger than other tracks 50 within PCB 40. Accordingly, terminal 48a is large enough to form good electrical connection with a battery inserted between layers 46, such as shown in FIG. 3B. Specifically, FIG. 3B shows PCB 40 separated between layers 46, and a battery 52 inserted therebetween, to make powered connection to PCB 40 and its elements 42. For purposes of clarity, only part of PCB 40 is shown in FIG. 3B, and none of elements 42 are shown. Layers 46a, 46b may separated by prying layers 46 apart. Battery 52 can for example be a Li coin cell battery known in the art.

Figure 3C:
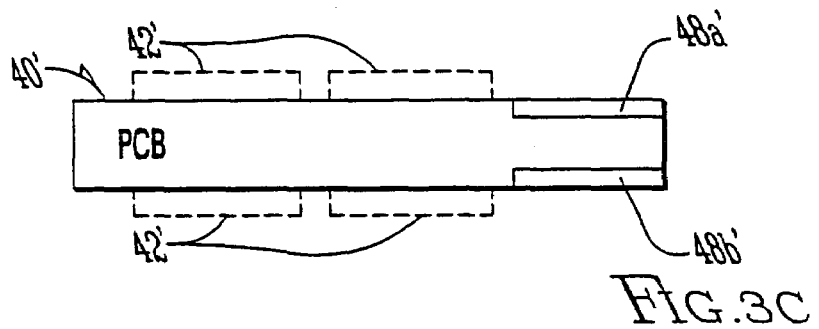
FIG. 3C shows a cross-sectional view (not to scale) of one monitor device of the invention for integrating a battery with a printed circuit board.
Figure 3D:
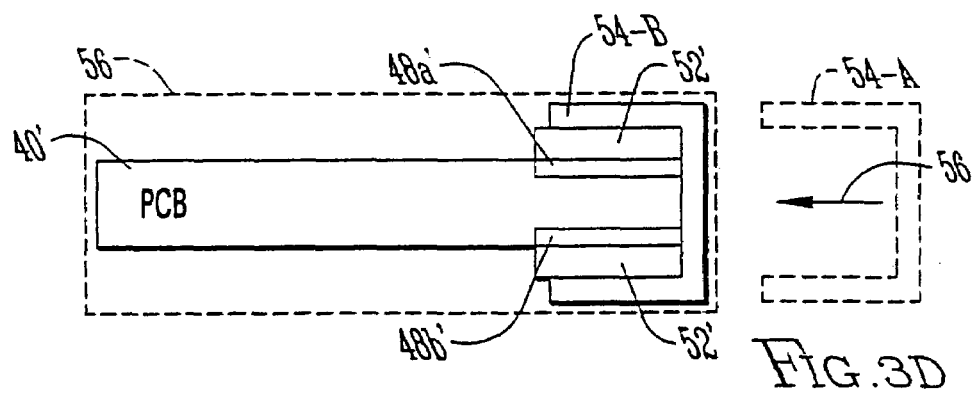
FIG. 3D shows an operational view of the monitor device of FIG. 3C, with a battery attached to sides of the underlying printed circuit board.

FIG. 3C shows another PCB 40' for use with a monitor device of the invention; except, in FIG. 3C, terminals 48a', 48b' are on opposing sides of PCB 40', as shown. PCB 40' can be a single layer board, or multi-layer board. Batteries 52' are coupled to PCB 40' as shown in FIG. 3D; and held to PCB 40' by end clip 54. FIG. 3D illustrates clip 54 as a stand-alone element 54-A; and alternatively as element 54-B holding batteries 52' in place to PCB 40'. End clip 54 slides over PCB 40' and batteries 52' as illustrated by arrow 56. End clip 54 is preferably conductive to complete the circuit to power PCB 40' (at a contact point with PCB 40') and its elements 42 for use as monitor device.

Figure 3E:
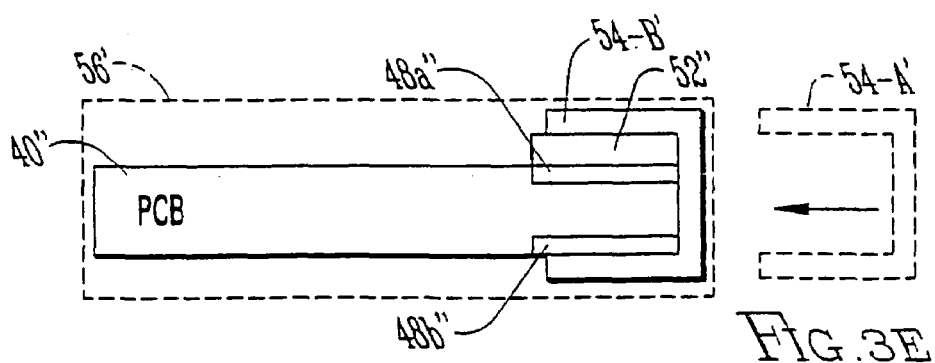
FIG. 3E shows an operational view of another monitor device of the invention, with a battery attached to one side of the underlying printed circuit board.

Battery attachment to PCB 40" can also be made as in FIG. 3E, where battery (or batteries) 52" is attached to one side of PCB 40". To make overall circuit connectivity, battery 52" connects to terminal 48a", and end clip 54' makes connection with terminal 48b", as shown. A contact point with PCB 40" can be made to complete desired circuit functions. End clip 54 is thus preferably conductive to complete the circuit to power PCB 40" and its elements 42 for use as a monitor device.

The battery integrations with PCBs of FIGS. 3D and 3E provide for simple and secure ways to mount batteries 52 within a package. Specifically, a housing 56 made to surround PCB 40 abuts end clip 54 and PCB 40, as shown, to secure the monitor device for use in varied environments, and as a small package. Housing configurations are shown and described in greater detail below.

FIG. 3F shows another PCB 60 for use with a monitor device of the invention. A battery 62 couples to PCB 60, as shown, and a connecting element 64 completes the circuit between battery 62 and PCB 60 to power the monitor device. Preferably, element 64 is tensioned to help secure battery 62 to PCB 60. FIG. 3G shows PCB 60 and element 64 coupled together and without battery 62. A terminal 66 (similar to terminals 48) is also shown in FIG. 3G to contact with one side of battery 62.

FIG. 4 illustrates a preferred embodiment of the invention, not to scale, where packaging associated with a monitor device "powers" the device upon removal of the packaging. Specifically, in FIG. 4, one monitor device 70, with adhesive strips 72, is shown with a protective wrapper 74 and non-stick strips 76. One non-stick strip 76a has an extension 77 that electrically separates device 70 and a battery 78 so as to prevent electrical contact therebetween. Non-stick strip 76a is preferably thin, such as paper coated with non-stick material. Once strip 76a is removed by a user, connecting element 80 forces battery 78 to contact monitor device 70, thereby powering the device. In this way, battery power is conserved until monitor device 70 is used operationally. Element 80 can for example take the form of element 64, FIG. 3G. FIG. 4A shows monitor device 70 with wrapper 74 and non-stick strips 76 removed; as such, element 80 forces battery 78 to device 70 to make electrical contact therewith, powering device 70. Those skilled in the art should appreciate that changes can be made within the above description without departing from the scope of the invention, including a monitor device with a single non-stick strip (instead of two) that has an extension to decouple the battery from device 70 until the strip is removed. Alternatively, the wrapper can couple with the extension to provide the same feature; so that when the wrapper is removed, the monitor device is powered.

Figure 5:
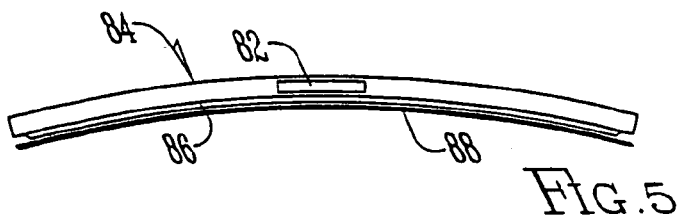
FIGS. 5 and 5A illustrate one monitor device integrated within a label, in accord with the invention.
Figure 5A:
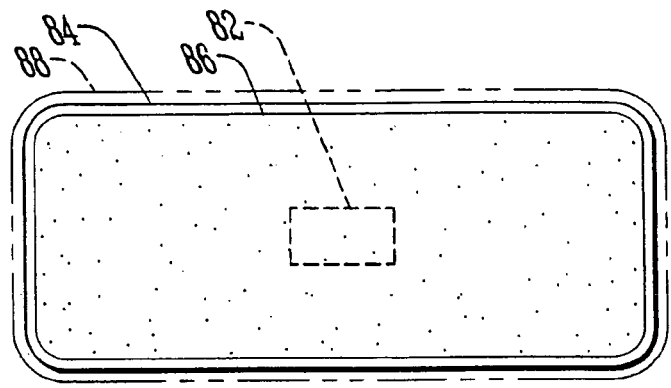

FIG. 5 shows a monitor device 82 formed within a label 84. Instead of adhesive strips, device 82 is disposed within label 84 for attachment, as above, to objects and persons. Label 84 has an adhesive 86 over one side, and preferably a non-stick strip 88 covering adhesive 86 until removed. For purposes of illustration, strip 88 is not shown in contact with adhesive 86, though in fact adhesive 86 is sandwiched in contact between strip 88 and label 84. Device 82 and label 84 provide an alternative to the monitor devices with adhesive strips described above, though with many of the advantages. FIG. 5A shows a front view of device 82, with adhesive 86 covering the one side of label 84, and with strip 88 shown transparently in covering adhesive 86 until removed.

Figure 6:
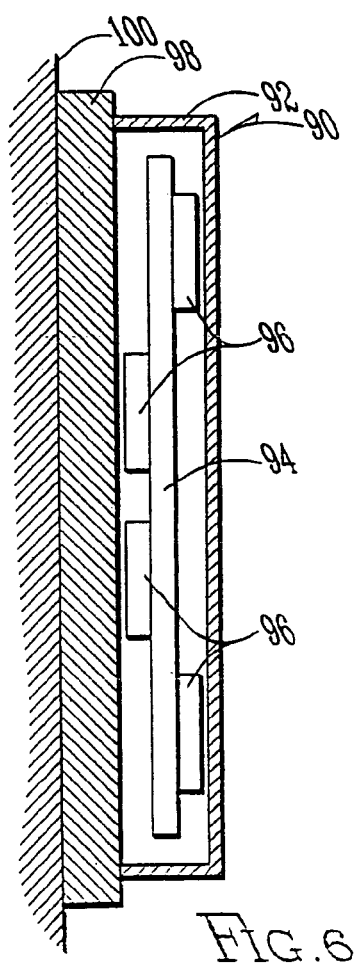
FIG. 6 shows a monolithic monitor device constructed according to the invention for attachment to an object by way of mechanical attachment.

FIG. 6 shows a monolithic monitor device 90 constructed according to the invention. A rigid outer housing 92 surrounds PCB 94 and internal elements 96 (e.g., elements 10-22, FIG. 1), which provide functionality for device 90. A magnetic element 98 couples with device 90 so that device 90 is easily attached to metal objects 100. Accordingly, device 90 is easily attached to, or removed from, object 100. Those skilled in the art should appreciate that alternative mechanical attachments are possible to couple device 90 to object 100, including a mechanical pin or clip.

The MMDs of the invention operates to detect movement "metrics." These metrics include, for example, airtime, speed, power, impact, drop distance, jarring and spin; typically one MMD detects one movement metric, though more than one metric can be simultaneously detected by a given MMD, if desired (potentially employing multiple detectors). The MMD detector is chosen to provide signals from which the processor can interpret and determine the desired metric. For example, to detect airtime, the detector is typically one of an accelerometer or piezoelectric strip that detects vibration of an object to which the MMD is attached. Furthermore, the MMD of the invention preferably monitors the desired metric until the metric passes some threshold, at which time that metric is tagged with time and date information, and stored or transmitted off-board. If the MMD operates within a single day, only time information is typically tagged to the metric.

By way of example, if the detector is an accelerometer and the MMD is designed to monitor "impact" (e.g., acceleration events that are less than about ½ second)—and yet impact data is not considered interesting unless the MMD experiences an impact exceeding 50 g's—the preferred MMD used to accomplish this task would continuously monitor impact and tag only those impact events that exceed 50 g's. The "event" in this example is thus a "50 g event." Such a MMD is for example useful when attached to furniture, or a package, in monitoring shipments for rough treatment. The MMD might for example record a 50 g event associated with furniture shipped on Oct. 1, 2000, from a manufacturer in California, and delivered on Oct. 10, 2000 to a store in Massachusetts. If an event stored in MMD memory indicates that on Oct. 5, 2000, at 2:30 pm, the furniture was clearly dropped, responsibility for any damages can be assessed to the party responsible for the furniture at that time. Accuracy of the time tag information can be days, hours, minutes and even seconds, depending on desired resolution and other practicalities.

Accordingly, data from such a MMD is preferably stored in internal memory (e.g., memory 20, FIG. 1) until the data are retrieved by receiver 24. In the example above, the interrogation to read MMD data occurs at the end of travel of the MMD from point A to point B. Multiple events may in fact occur for a MMD during travel; and multiple events are usually stored. Alternatively, a MMD may communicate the event at the time of occurrence so long as a receiver 24 is nearby to capture the data. By way of example, if each FEDEX truck contained a receiver integrated with the truck, then any MMD contained with parcels in the truck can transmit events to the receiver at the occurrence of the event.

In another application, one or more monitor devices are attached to patients in a hospital, and one or more receivers are integrated with existing electronics at the hospital (e.g., with closed circuit television, phone systems, etc.). In operation, these device are for example used to detect "events" that indicate useful information about the patients—information that should be known. If for example the monitor device has a Hall Effect detector that detects when the device is inverted, then a device attached to the collar bone (or clothing) of a patient would generate an "event" when the patient falls or lays down. An impact detector may also be used advantageously, to detect for example a 10 g event associated with a patient who may have fallen. Accordingly, monitor devices applied to patients in hospitals typically transmit event data at occurrence, so that in real time a receiver relays important medical information to appropriate personnel.

Movement devices of the invention can also transmit movement or other metrics at select intervals. If for example "impact" data is monitored by a MMD, then the MMD can transmit the maximum impact data for a selected interval—e.g., once per minute or once per five minutes, or other time interval. In this way, a MMD applied to a patient monitors movement; and any change in movement patterns are detected in the appropriate time interval and relayed to the receiver. A MMD may thus be used to inform a hospital when a patient is awake or asleep: when asleep, the MMD transmits very low impact events; when awake, the MMD transmits relatively high impact events (e.g., indicating that the patient is walking around).

Figure 7:
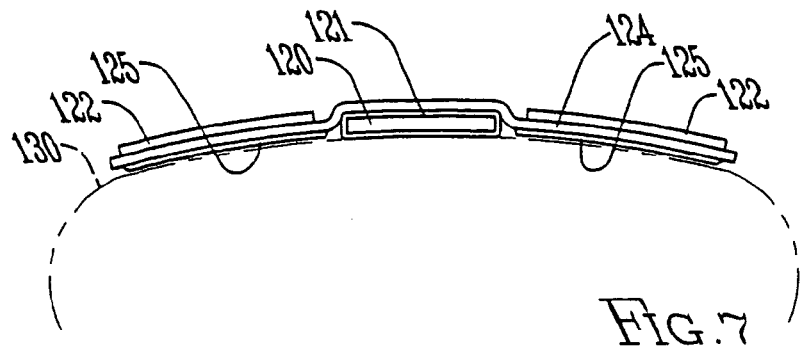
FIG. 7 shows one monitor device of the invention used to monitor patient health characteristics.

FIG. 7 shows one monitor device 120 constructed according to the invention. Similar to device 10" of FIG. 2 with regard to the adhesive bandage features of the device, device 120 has a detector in the form of a piezoelectric strip 122 disposed with the adhesive strip 124 (and, preferably, padding 121). Strip 124 has adhesive 125 such as described above so that device 120 is easily attached to a human, e.g., to human arm 130. In operation, as shown by schematic 130 of FIG. 7A, bending of strip 124 also bends piezoelectric strip 122, generating voltage spikes 123 detected by device processor 126. Device 120 may thus operate to detect the heart pulse of a person: the tiny physical perturbation of piezoelectric strip 122 caused by arterial pressure changes is detected and processed by device 120 as movement metric 127, which is then transmitted by port 129 to remote receiver(s) 132 as wireless data 133. The pulse data 127, over time, is usefully reconstructed for analytical purposes, e.g., as data 134 on display 136, and may indicate stress or other patient condition that should be known immediately. By way of example, an "event" determined by device 120 based on movement metric 127 can be the absence or variation of a pulse, perhaps indicating that the patient died or went into cardiac arrest. It is clear that if arm 130 moves, the voltage signal generated by piezoelectric detector 122 may swamp any signal from the patient's pulse; however, since pulse data is detected at approximately 50 to 250 times per second, the underlying signal can be recovered, particularly after arm 130 ceases movement. Device 120 can include an A/D converter and/or voltage-limiting device 121 to facilitate measurement of voltage signals 123 from piezoelectric strip detector 122. A battery 138 such as a Lithium coin cell can be used to power device 120.

Device 120 may alternatively detect patient movement to provide real time detection of movement of a person or of part of that person. For example, such a device 120 may be used to monitor movement of an infant (instead of arm 150) or other patient.

Figure 7A:
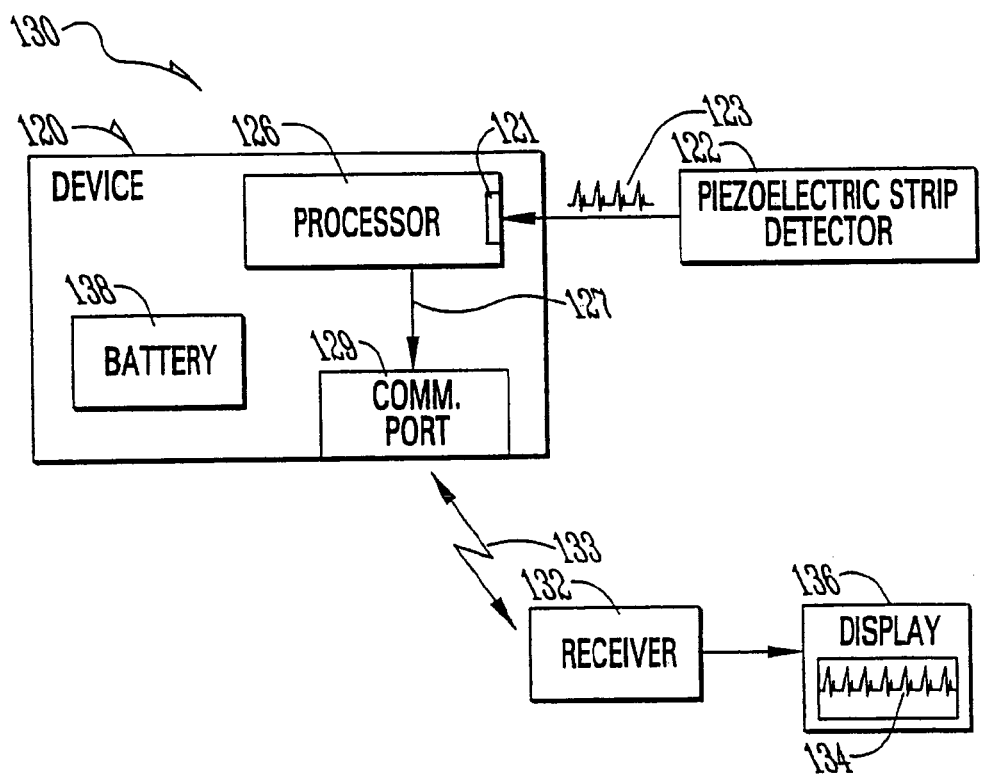
FIG. 7A shows a system of the invention used to monitor pulse characteristics for patient health, with the device of FIG. 7.
Figure 7B:
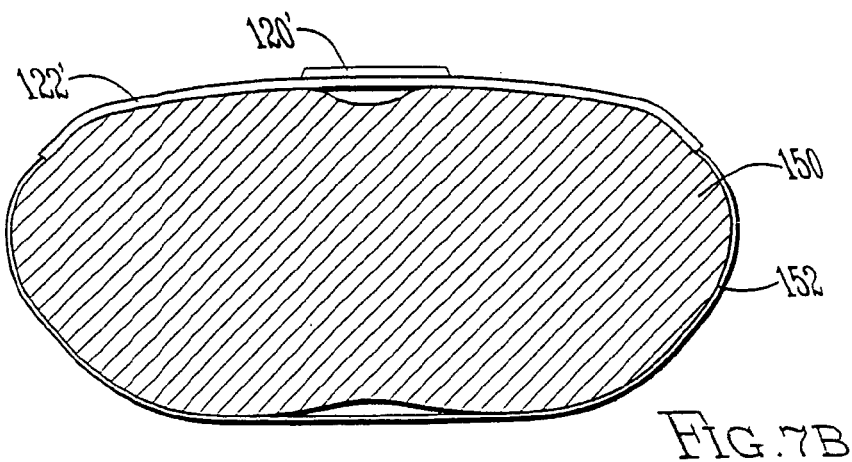
FIG. 7B shows an alternative monitor device of the invention used to monitor respiratory behavior such as with the system of FIG. 7A.

Note that the application of a monitor device 120 as described in FIG. 7 and FIG. 7A can be expanded to detect respiratory behavior of a patient. FIG. 7B shows a simplified schematic of one device 120' with a longer piezoelectric strip detector 122'. Detector 122' circumferentially extends, at least part way, around the chest 150 of a patent; and movement of chest 150 during breathing generates voltage variations (e.g., similar to variations 133, FIG. 7) in response to physical perturbations of detector 122'. Similar to pulse rate and pulse strength, therefore, device 120' detects respiratory rate and/or strength. Pulse rate is determined by signal frequencies associated with movement metric 127; and pulse strength is determined by magnitudes associated with movement metric 127. Note that strip detector 122' may be attached about chest 150 by one of several techniques, including by an adhesive strip (not shown) such as described above. A strap or elastic member 152 may be used to surround chest 150 to closely couple detector 122' to chest 150.

Devices such as device 120 or 120' have additional application such as for infant monitoring. Attaching such a device to the chest (instead of arm 150) of an infant to monitor respiration, pulse and/or movement provides a remote monitoring tool and may prevent death by warning the infant's parents. A monitor device 10w, FIG. 2E, may alternatively be used in such an application. Specifically, if for example a monitor device of the invention is attached to chest 150 of a child, processor 126 searches for "events" in the form of the absence of pulse, respiration and/or movement data. The device may thus track pulse or respiratory rate to synch up to the approximate frequency of the rate. When the device detects an absence in the repetitive signals of the pulse or respiratory rate, the device sends a warning message to an alarm for the parents. A system suitable for application with such an application is discussed in more detail in FIGS. 55 and 56.

Data transmissions from a monitor device of the invention, to a receiver, typically occur in one of three forms: continuous transmissions, "event" transmissions, timed sequence transmissions, and interrogated transmissions. In continuous transmissions, a monitor device transmits detector signals (or possibly processed detector signals) in substantially real time from the monitor device to the receiver. Data reconstruction at the receiver, or at a computer arranged in network with, or in communication with, the receiver, then proceeds to analyze the data for desired characteristics. By way of example, by attaching multiple monitor devices to a person, all transmitting real-time data signals to the receiver, a reconstruction of that person's activity is determined.

Figure 8:
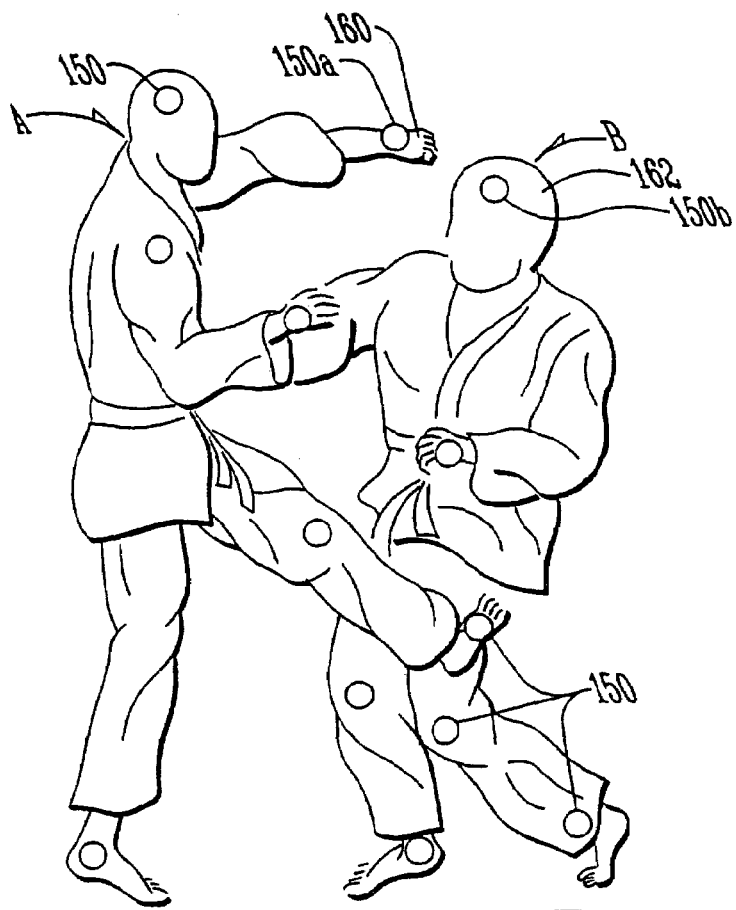
FIG. 8 illustrates application of a plurality of MMDs, of the invention, to athletes to facilitate training and/or to provide excitement in broadcast media.
Figure 8A:
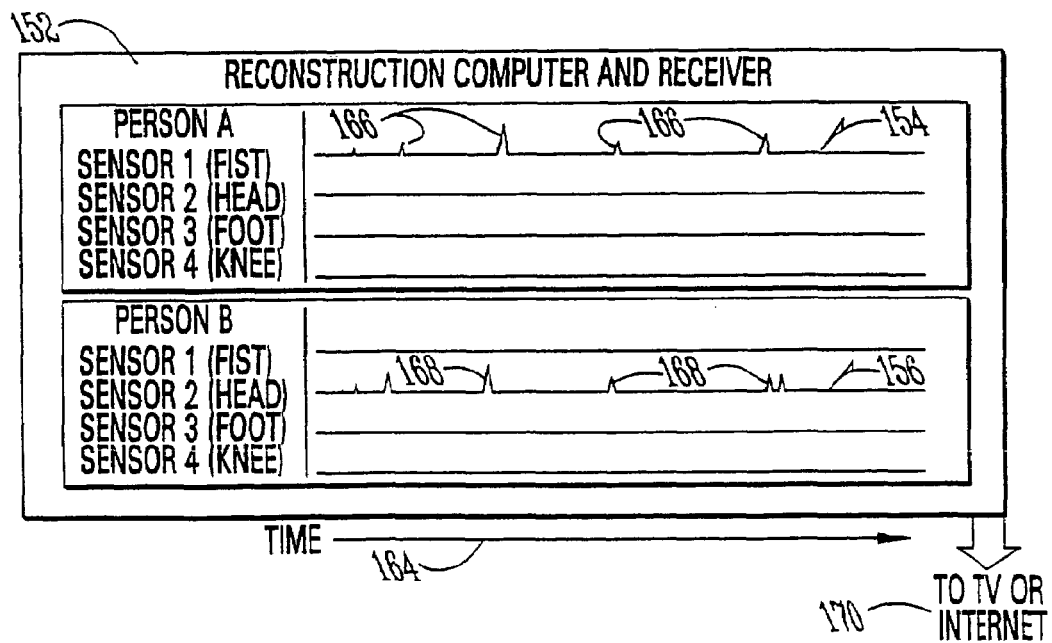
FIG. 8A illustrates real time data acquisition, reconstruction and display for data wirelessly transmitted from the MMDs of FIG. 8.

Consider for example FIG. 8. In FIG. 8, a plurality of MMDs 150 are attached to person "A" and person "B". As shown, person A is engaged in karate training with person B. Data from MMDs 150 "stream" to a remote receiver, such as to the reconstruction computer and receiver 152 of FIG. 8A. Each MMD 150 preferably has a unique identifier so that receiver 152 can decode data from any given MMD 150. MMDs are placed on persons A, B at appropriate locations, e.g., on each foot and hand, head, knee, and chest; and receiver 152 associates data from each MMD 150 with the particular location. As data streams from MMD 150 to receiver 152, data is reconstructed such as shown in plots 154 and 156. Data plot 154 shows exemplary data from MMD 150a on the fist 160 of person A, and data plot 156 shows exemplary data from MMD 150b on the head 162 of person B. Each plot 154, 156 are shown in FIG. 8A as a function of time 164. Other data plots for other sensors 150 (e.g., for illustrative sensors 2, 3, 4) are not shown, for purposes of clarity.

Data plots 154, 156 have obvious advantages realized by use of the MMDs of the invention. For example, plot 154 illustrates several fist "strikes" 166 generated by person A on person B, and data plot 156 illustrates corresponding blows 168 to the head of person B. Data 154, 156 may for example be used in training, where person B learns to anticipate person A more effectively to soften or eliminate blows 168.

Data plots 154, 156 have further advantages for broadcast media; specifically, data 154, 156 may be simultaneously relayed to the Internet or television 170 to display impact speed and intensity for blows given or received by persons A, B, and in real time, to enhance the pleasure and understanding of the viewing audience (i.e., viewers of television, and users of the Internet). Moreover, MMDs of the invention remove some or all of the subjectivity of impact events: a blow to an opponent is no longer qualitative but quantitative. By way of example, the magnitude of strikes 166 and blows 168 are preferably provided in the data streamed from MMDs 150, indicating magnitude or force of the blow or strike. Data 154, 156 thus represents real time movement metric data, such as acceleration associated with body parts of persons A, B. Data 154, 156 may thereafter be analyzed, at receiver 152, to determine "events", such as when data 154, 156 indicates an impact exceeding 50 g's (or other appropriate or desired measure).

Figure 8B:
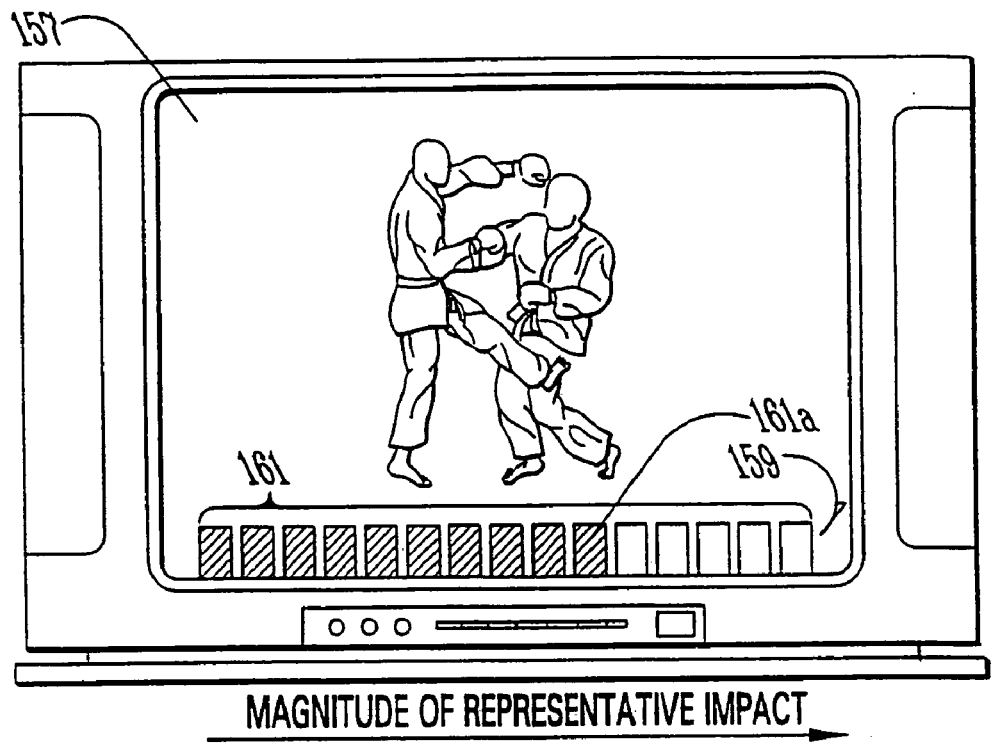
FIG. 8B illustrates a television display showing data generated in accord with the teachings of the invention.

FIG. 8B illustrates a representative display on television 157, including appropriate event "data" 159 generated by a MMD system of the invention. Data 159 can for example derive from receiver 152, which communicates the appropriate event data 159 to the broadcaster for TV 157. Such event data 159 can include magnitude or power spectral density of acceleration data generated by MMDs 150. Data 159 is preferably displayed in an easy to understand format, such as through bar graphs 161, each impact detected by one or more MMDs 150 (in certain instances, combining one or more MMDs as data 159 can be useful). Bar graphs 161 preferably indicate magnitude of the impact shown by data 159 by peak bar graph element 161*a* on TV 157.

Figure 8C:
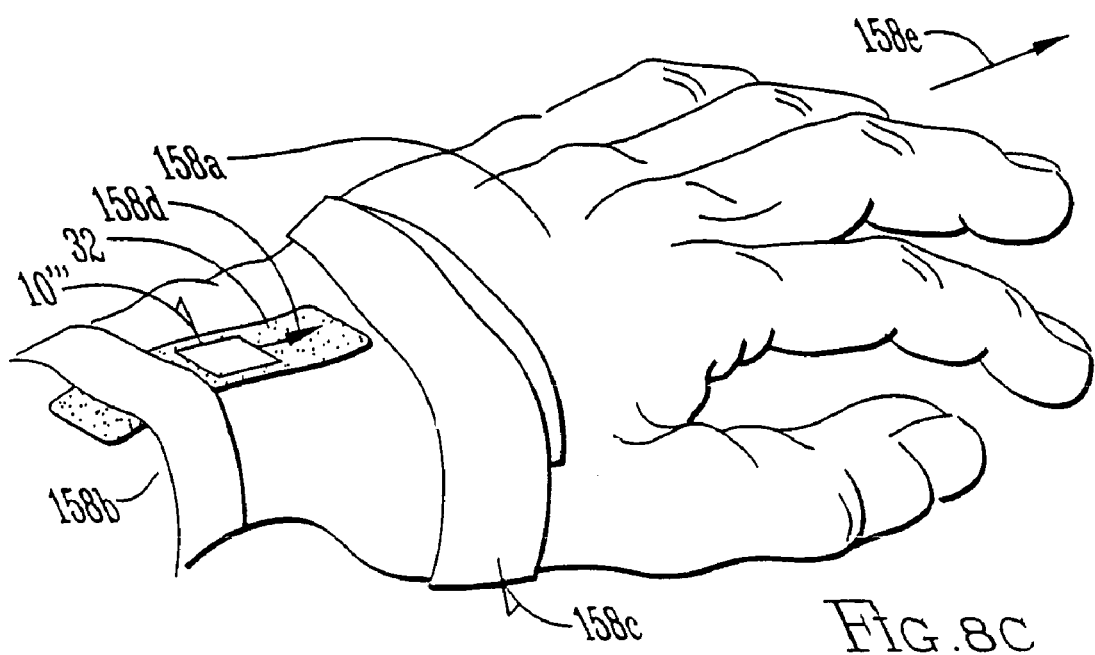
FIG. 8C shows a one MMD applied to a human fist in accord with the invention.

Those skilled in the art should appreciate that any number of MMDs 150 may be used for applications such as shown in FIG. 8. In boxing, for example, it may be appropriate to attach one MMD 150 per fist. One useful MMD in this application is for example monitor device 10 of FIGS. 2, 2D. That is, such a device is easily attached to the boxer's fist 158*a* or wrist 158*b* and, if desired, prior to applying gloves and wrapping 158*c*, as shown in FIG. 8C. The device can alternatively be placed with wrapping 158*c*—making the device practically unnoticeable to the boxer. Preferably, MMD 10''' of FIG. 8C includes an accelerometer (as the MMD detector) oriented with a sensitivity axis 158*d* as shown: axis 158*d* being substantially aligned with the strike axis 158*e* of fist 158*a*. Data from the MMD wirelessly transmits through the gloves and wrapping to receiver 152. Alternatives are also suitable, for example applying the MMDs to the boxer's wrapping or glove. A MMD can also be integrated within the boxing glove, if desired. In the event that the detector of the MMD is an accelerometer, then the sensitive axis of the accelerometer is preferably arranged along a strike axis of the boxer.

Data acquired from MMDs in sports like boxing and karate are also preferably collated and analyzed for statistical purposes. Data 154, 156 can be analyzed for statistical detail such as: impacts per minute; average strike force per boxer; average punch power received to the head; average body blow power; and peak striking impact. Rotational information may also be derived with the appropriate detector, including typical wrist rotation at impact, a movement metric that may be determined with a spin sensor.

Figure 9:
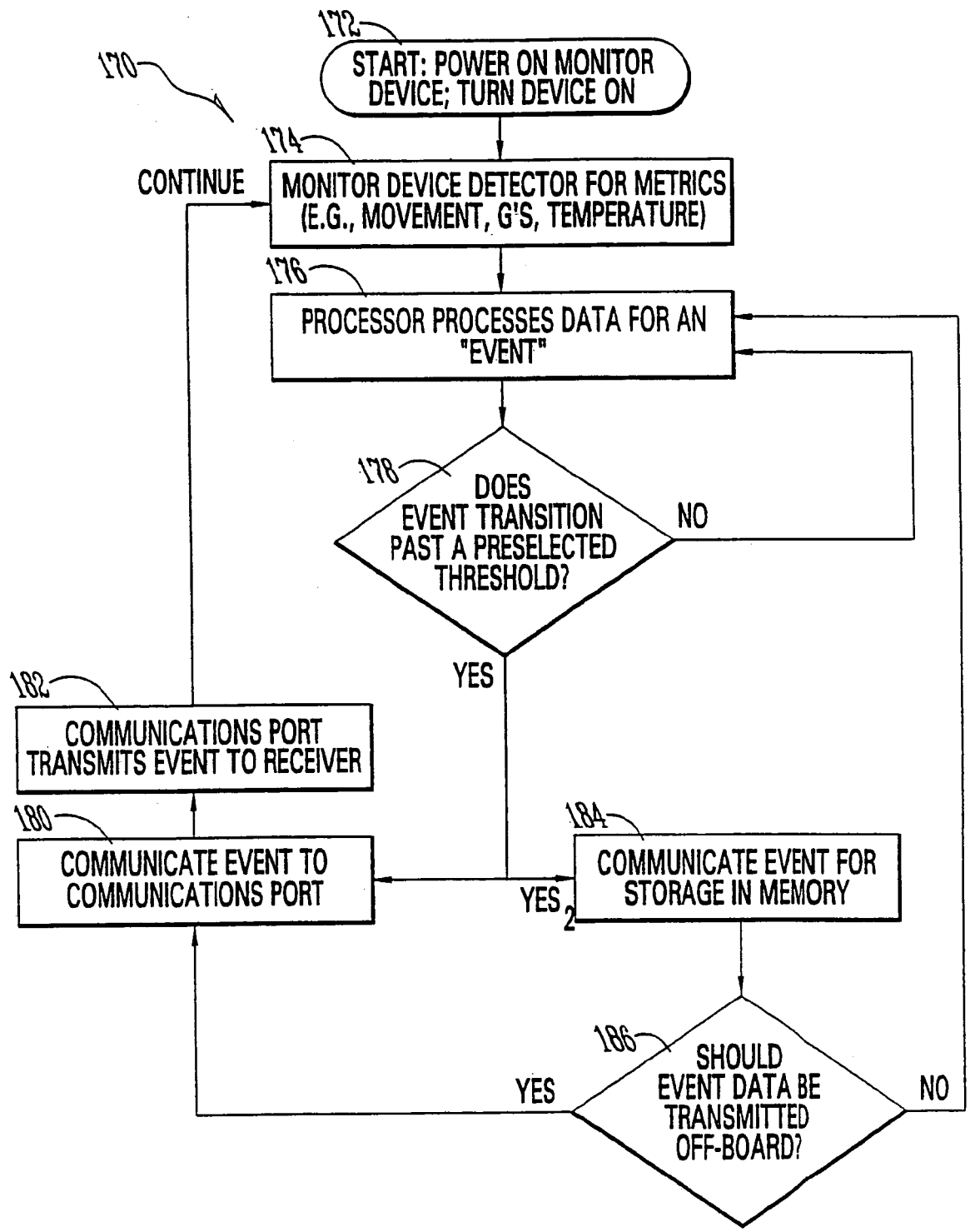
FIG. 9 shows a flow-chart illustrating "event" based and timed sequence data transmissions between a monitor device and a receiver, in accord with the invention.

Other than continuous transmissions, such as illustrated in FIG. 8, data from monitor devices of the invention also occur via one of "event" transmissions, timed sequence transmissions, and/or interrogated transmissions. FIG. 1 illustrates how interrogated transmissions preferably function: e.g., receiver 24 interrogates device 10 to obtain metrics. Event transmissions according to preferred embodiments are illustrated as a flow chart 170 of FIG. 9. Timed sequence transmissions according to preferred embodiments are also illustrated within flow chart 170 of FIG. 9. In FIG. 9, flow chart 170 begins in step 172 by powering the monitor device—either by inserting the battery, turning the device on, or removing a wrapper (or by similar mechanism) to power the device at the appropriate time. Once powered, the monitor device monitors detector signals, in step 174, for metrics such as movement, temperature and/or g's. By way of example, to measure airtime or impact, the device processor monitors an accelerometer for the movement metric of acceleration. Step 176 assesses the metric for "events" such as airtime or "impact" (or, for example, for an event such as when temperature exceeds a certain threshold, or an event such as when humidity decreases below a certain threshold). Typically, though not required, all events are not reported, stored or transmitted. Rather, as shown in step 178, events that meet or pass a preselected threshold are reported. By way of example, is an airtime event greater than ½ second—a magnitude deemed interesting by snowboarders? If so, such an event may be reported. If not, an airtime event of less than ½ second is not reported, and decision "No" from 178 is taken. If the event exceeds some threshold, decision tree "Yes" from 178 sends the event data to the communications port (e.g., communications port 26, FIG. 1) in step 180. The communications port then transmits the event to a receiver (e.g., receiver 24, FIG. 1) in step 182. As an alternative, decision tree Yes$_2$ sends the event data to memory such that it is stored for later transmission, in step 184. The Yes$_2$ decision tree is used for example when a receiver is not presently available (e.g., when no receiving device is available to listen to and capture data transmitted from the monitor device). Eventually, however, event data is transmitted off-board, in step 186, such as when memory is full (a receiver should be available to capture the event data before memory becomes full) or when the monitor device is scheduled to transmit the data at a preselected time interval (i.e., a timed sequence transmission). For example, event data stored in memory may be transmitted off board every five minutes or every hour; data captured within that time interval is preferably stored in memory until transmission at steps 180 and 182.

Note that timed sequence transmission of event data approaches "continuous" transmission of movement metric data for smaller and smaller timed sequence transmissions. For example, if data from the monitor device is communicated off-board each second (or less, such as each one tenth of a second), then that data becomes more and more similar to continuously transmitted data from the detector. Indeed, if sampling of the detector occurs at X Hz, and timed transmissions also occur at X Hz, then "continuous" or "timed sequence" data may be substantially identical. Timed sequence or event data, therefore, provides for the opportunity to process the detector signals, between transmissions, to derive useful events or to weed out noise or useless information.

Figure 10:
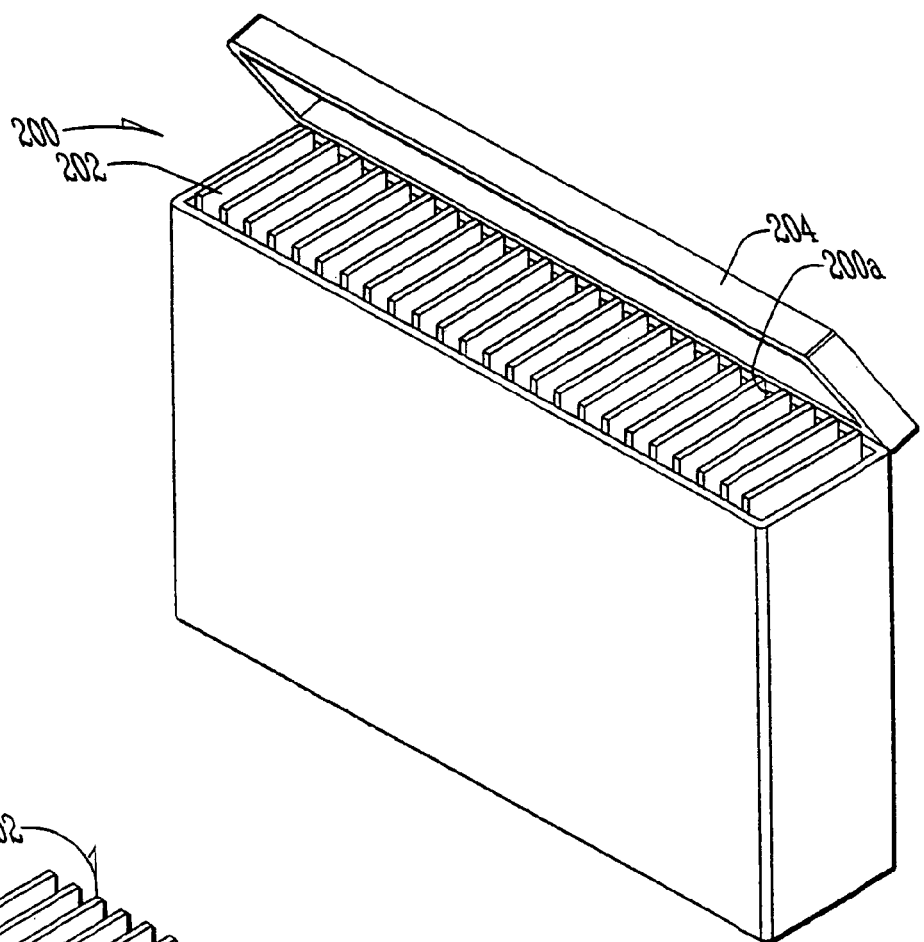
FIG. 10 shows a sensor dispensing canister constructed according to the invention.

FIG. 10 shows a sensor-dispensing canister 200 constructed according to the invention. Canister 200 is shown containing a plurality of sensor 202. A lid 204 may be coupled with canister 200 to enclose sensors 202 within canister 200, as desired. Each of sensors 202 can for example be a monitor device such as described above; however canister 200 can be used for other battery-powered sensors. Although canister 200 is shown with two-dozen sensors 202, a larger or smaller number of sensors may be contained within its cavity 200*a*. As described in more detail below, canister 200 preferably contains one or both of (a) canister electronics and (b) a base assembly. Lid 204 preferably functions as a switch, to power the canister electronics when lid 204 is open, and to cause canister electronics to sleep when lid 204 is closed.

Figure 10A:
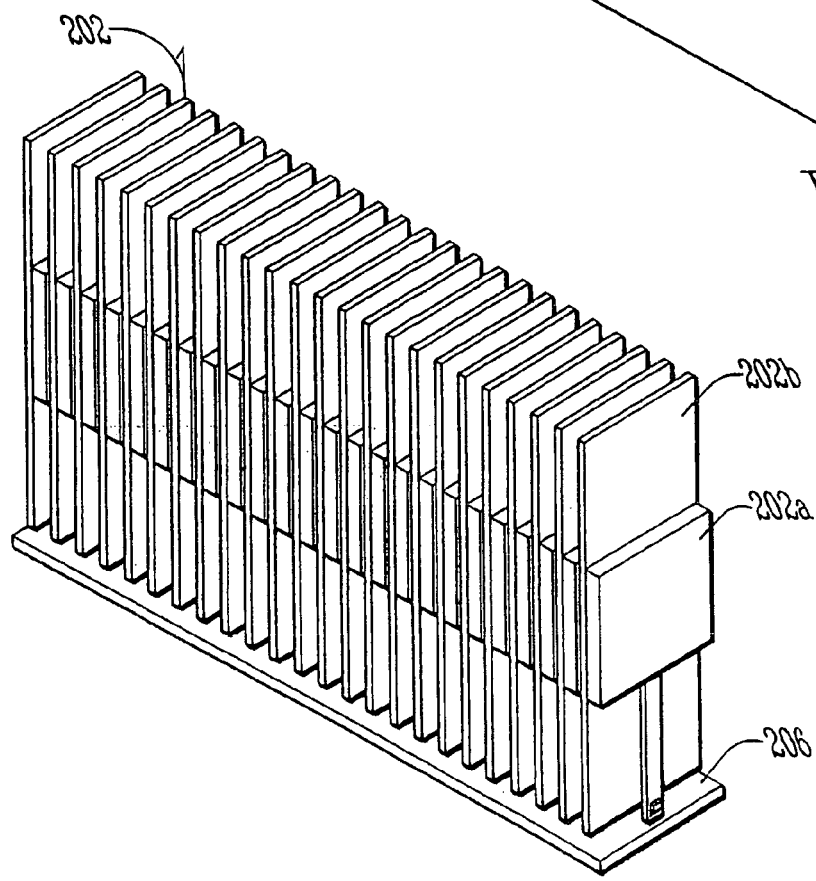
FIG. 10A shows an array of sensors arranged for mounting within the canister of FIG. 10.
Figure 10B:
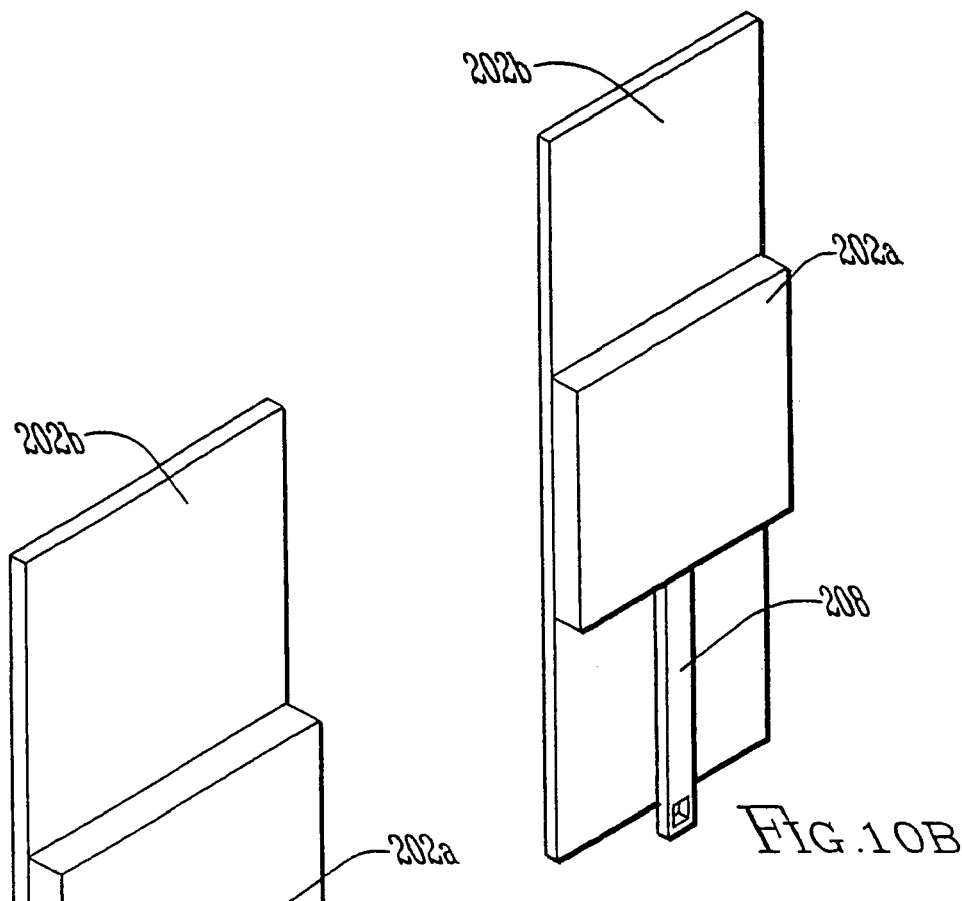
FIG. 10B shows one sensor of the array of sensors of FIG. 10A.
Figure 10C:
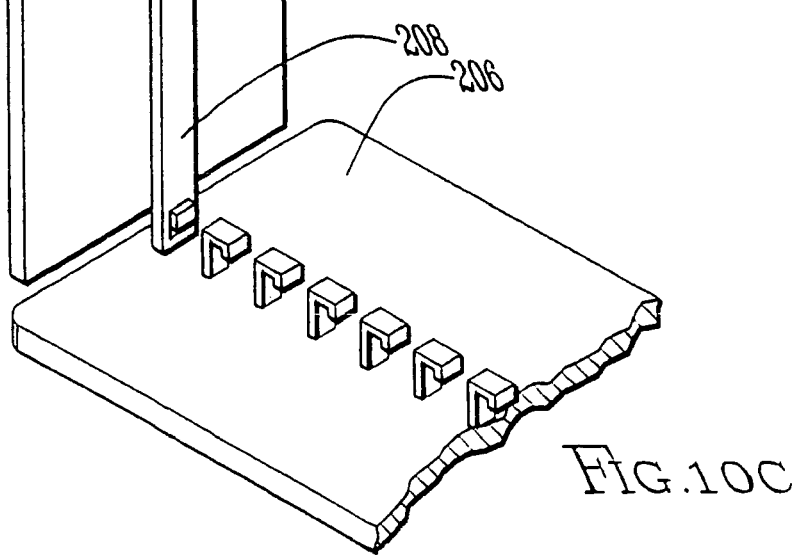
FIG. 10C shows an interface between one sensor and a base assembly in the canister of FIG. 10.

FIG. 10A shows sensors 202 with base assembly 206, and, for purposes of clarity, without the rest of canister 200. Each of sensors 202 is shown with a monitor device 202*a* and an adhesive strip 202*b*; however, canister 200 may be used with other sensors (i.e., sensors that are not MMDs or EMDs) without departing from the scope of the invention. FIG. 10B illustrates one sensor 202 in the preferred embodiment, and also illustrates a Mylar battery insulator strip 208 that keeps the sensor battery from touching its contact or terminal (not shown) within monitor device 202*a*. Strip 208 can for example serve as the "non-stick" strip or extension 77 discussed above in connection with FIG. 4. Strip 208 preferably couples to base assembly 206 such as shown in FIG. 10C.

Figure 10D:
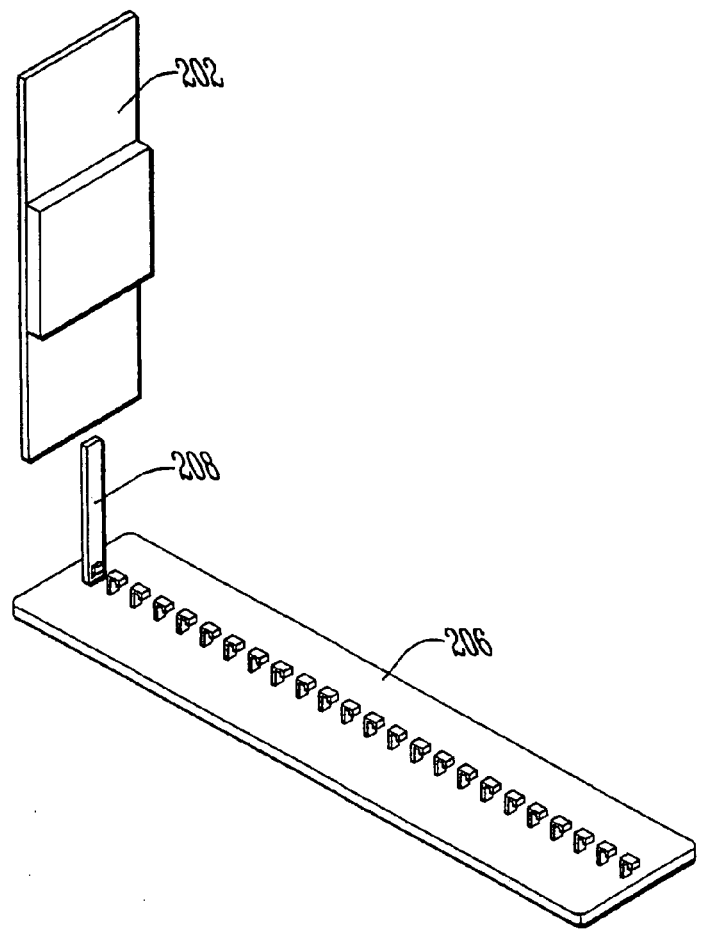
FIG. 10D shows an operational disconnect of one sensor from the base assembly in FIG. 10C.

Accordingly, when a user removes a sensor 202 from canister 200, strip 208 remains with base assembly 206—and is no longer in contact with sensor 202—and the monitor device's internal battery powers the device for use with its intended application, as shown in FIG. 10D.

Figure 10E:
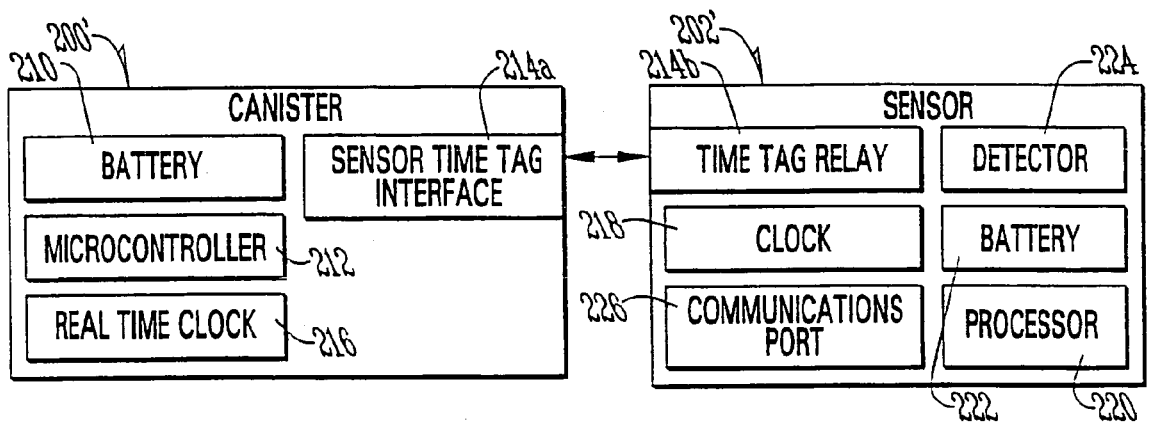
FIG. 10E schematically illustrates canister electronics and a sensor as part of the canister of FIG. 10.

In one preferred embodiment of the invention, a canister 200' (e.g., similar to canister 200 but with internal electronics) has its own battery 210, micro-controller 212, sensor time tag interface 214*a*, and real time clock 216 (collectively the "canister electronics"), as shown in FIG. 10E. With such an embodiment, a sensor 202' for use with canister 200' has a mating time tab interface 214*b*. In addition to time tag interface 214*b*, sensor 202' has a clock 218, processor 220, battery 222, detector 224 and communications port 226. In operation, sensor 202' is generally not powered by battery 222 until removed from canister 200', as described above. Accordingly, real time clock information (e.g., the exact date and time) cannot be maintained within sensor 202' while un-powered (i.e., so long as insulator strip 208' prevents battery 222 from powering sensor 202') since clock 218 and other electronics require power to operate. However, in FIG. 10E, the advantage provided by the canister electronics is that time tag information from real time clock 216 is imported to sensor 202' through interfaces 214*a*, 214*b* after battery 222 powers device 202*a*' but before interfaces 214*a*, 214*b* disconnect so that sensor 202' can be used operationally. As such, in the preferred embodiment shown in FIG. 10F, interface 214*a* takes the form of flex cable 230 that remains attached between canister electronics and device 202*a*' until flex cable 230 extends to its full length, whereinafter sensor 202' disconnects from cable 230. Time tag relay 214*b* of device 202*a*', FIG. 10F, thus takes the form of a plug (not shown) to connect and alternatively disconnect with flex cable 230. In FIG. 10F, canister electronics (e.g., elements 210, 212, 216) are disposed within base assembly 206' and therefore flex cable 230 appears to extend only to base assembly 206' when in fact cable 230 extends to canister electronics disposed therein. When a user removes sensor 202' from canister 200', device 202*a*' is powered when strip 208', held with base assembly 206' (or electronics therein) disconnects from sensor 202'; and at that time clock 218 is enabled to track real time. Before flex cable 230 disconnects from sensor 202', time and/or data information is communicated between interfaces 214*a*, 214*b* to provide the "real" time to sensor 202' as provided by clock 216. Once real time is provided to sensor 202', clock 218 maintains and tracks advancing time so that sensor 202' can tag events with time and/or date information, as described herein.

One advantage of sensor canister 200' is that once used, it may be reused by installing additional sensors within the cavity. In addition, one canister can carry multiple monitor devices, such as 100 MMDs that each respond to an event of "10 g's." In another example, another canister carries 200 MMDs that respond to an event of "100 g's." A canister of MMDs can be in any suitable number that meets a given application; typically however sensors within the canister of the invention are packaged together in groups of 50, 100, 150, 200, 250, 500 or 1000. A variety pack of MMDs can also be packaged within a canister, such as a canister containing ten 5 g MMDs, ten 10 g MMDs, ten 15 g MMDs, ten 20 g MMDs, ten 25 g MMDs, ten 30 g MMDs, ten 35 g MMDs, ten 40 g MMDs, ten 45 g MMDs, and ten 50 g MMDs. Another variety package can for example include groups of MMDs spaced at 10 g intervals. EMDs can also be packaged in variety configurations within canisters 200, 200'.

Canisters 200, 200' can also function to dispense one or a plurality of receivers. Specifically, each of elements 202 of FIG. 10 may alternatively be a receiver such as receiver 24 of FIG. 1. In this way, a plurality of receivers may be dispensed and powered as described above. FIG. 10G shows one receiver 231 constructed according to the invention. Receiver 231 has a communications port 232, battery 233 and indicator 234. Receiver 231 can further include processor 235, memory 236 and clock 237, as a matter of design choice and convenience such as to implement functionality described in connection with FIGS. 10G, 10H. Receiver 231 can for example be dispensed as one of a plurality of receivers—as an element 202, 202' dispensed from canisters 200, 200' above. In operation, battery 233 powers receiver 231 and receiver 231 receives inputs in the form of wireless communications (e.g., in accord with the teachings herein, wireless communications can include known transmission protocols such as radio-frequency communication, infrared communication and inductive magnetic communication) from a sensor such as a MMD. Communications port 232 serves to capture the wireless communications data such that indicator 234 re-communicates appropriate "event" data to a person or machine external to receiver 231. Specifically, in one embodiment, receiver 231 operates to relay very simple information regarding event data from a movement device. If for example a MMD sends event data to receiver 231 that reported the MMD experienced an airtime event of five seconds, and it was important that this information was known immediately, then receiver 231 is programmed (e.g., through processor 235) to indicate the occurrence of that five-second airtime event through indicator 234. Such data may also be stored in memory 236, if desired, until a person or machine requiring the data acquires it through indicator 234. By way of another example, receiver 231 can take the form of a ski lift ticket 238 shown in FIG. 10H. Lift ticket 238 is thus a receiver with an indicator 239 in the form of a LED. Lift ticket 238 is preferably made like other lift tickets, and may for example include bar code 240, indicating that a person purchased the ticket for a particular day, and ticket connecting wire 241 to couple ticket 238 to clothing. Lift ticket 238 may beneficially be used with a MMD having a speed sensor detector; and that MMD reports (by wireless communication) speed "events" that exceed a certain threshold, e.g., 40 mph. Lift ticket receiver 238 captures that event data and reports it though indicator 239. A person wearing lift ticket receiver 238 with a speed sensing MMD will thus be immediately known by the ski lift area that the person skis recklessly, as a lift operator can view the speeding violation indicator LED 239. Alternatively, indicator 239 is itself a wireless relay that communicates with a third receiver such as a ski ticket reader currently used to review bar code 240. Lift ticket receiver 238 can further include circuitry as in monitor device 10 of FIG. 1 so that it responds to wireless requests for appropriate "event data," such as speed violation data. As such, indicator 239 may take the form of a transmitter relaying requested event data to the third receiver, for example. Event data may be stored in memory 236 until requested by the third receiver interrogating lift ticket receiver 238.

Preferably, canisters 200' imparts a unique ID to the dispensed electronics—e.g., to each sensor or receiver taken from canister 200'—for security reasons. More particularly, in addition to communicating a current date and time to the dispensed electronics, canister 200' also preferably imparts a unique ID code which is used in subsequent interrogations of the dispensed electronics to obtain data therein. Therefore, data within a monitor device, for example, cannot be tampered with without the appropriate access code; and that code is only known by the party controlling canister 200' and dispensing the electronics.

FIG. 10G and FIG. 10H illustrate certain advantages of the invention. First, receivers in the form of lift tickets 238 may be packaged and dispensed to power the lift ticket upon use. Lift tickets are dispensed by the thousands and are sometimes stored for months prior to use. Accordingly, battery power may be conserved until dispensed so that internal electronics function when used by a skier for the day. Further, tickets 238 monitor a user's performance behavior during the day to look for offending events: e.g., exceeding the ski resort speed limit of 35 mph; exceeding the jump limit of two seconds; or performing an overhead flip on the premises. Whatever the monitor device is set to measure and transmit as "events" may be visually displayed (e.g., a LED or LCD) at indicator 234 or re-transmitted to read the offending information. Receiver 231 may incorporate transponders as discussed above to facilitate the indicator functionality, i.e., to relay data as appropriate.

Batteries used in the above MMDs and devices like the lift ticket can benefit by using paper-like batteries such as set forth in U.S. Pat. No. 5,897,522, incorporated herein by reference. Such batteries provide flexibility in several of the monitor devices described herein. Powering such batteries when dispensing a sensor or receiver still provides advantages to conserve battery power until the sensor or receiver is used. A device battery 18 of FIG. 1 can for example be a paper-like battery or coin cell.

FIG. 10I shows yet another sensor 231' constructed according to the invention. Like receiver 231, sensor 231' preferably conforms to a shape of a license ticket, e.g., a ski lift ticket. However sensor 231' does not couple to a separate monitor device; rather, sensor 231' is a stand-alone device that serves to monitor and gauge speeding activity. Like other sensors of the invention, an "event" is generated and communicated off-board (i.e., to a person or external electronics) when sensor 231' exceeds a pre-assigned value. Typically, that value is a speed limit associated with the authority issuing sensor 231' (e.g., a resort that issues a ski lift ticket). Sensor 231' is preferably dispensed through one of the "power on" techniques described herein, such as by dispensing sensor 231' from a canister 200, 200'. Typically, when sensor 231' detects a speeding event, (a) data is communicated off-board (e.g., sensor 231' generates a wireless signal of the speed violation), and/or (b) a visual indicator is generated to inform the authority (e.g., via a ski lift operator of the ski lift area) of the violation. In case (a), indicator 234' may for example be a communications port such as port 16, FIG. 1; in the case (b), indicator 234' may for example be an LED or other visual indicator that one can visually detect to learn of the speeding violation. Indicator 234' of one embodiment is a simple LED that turns black (ON), or alternatively white (OFF), after the occurrence of a speeding event. A quick visual review of sensor 231' thus informs the resort of the speeding violation.

Sensor 231' also has a battery 233' that is preferably powered when sensor 231' is dispensed to a user (e.g., to a snowboarder at a resort). Optionally, position locator 243 is included with sensor 231' to track earth location of sensor 23'; processor 235' thereafter determines speed based upon movement between locations over a time period (e.g., distance between a first location and a second location, divided by the time differential defined by arriving at the second location after leaving the first location, provides speed). Clock 237' provides timing to sensor 231'. Optionally, memory 236' serves one of several functions as a matter of design choice. Data gathered by sensor 231' may be stored in memory 236'; such data may be communicated off-board during subsequent interrogations. As discussed above, data may also be communicated off-board at the occurrence of a speeding "event." As an alternative, indicator 234' may be a transponder RFID tag to be read by a ticket card reader. In one embodiment, on slope transmitters irradiate sensor 231' with a signal that reflects to determine Doppler speed; that speed is imparted to sensor memory 236' and reported to the resort.

Preferably, sensor 231' operates in "low power" mode. Position locator 243 in one preferred embodiment is a GPS receiver. GPS receiver and processor 243, 235' for example collectively operate to make timed measurements of earth location so as to coarsely measure speed. For example, by measuring earth location each five seconds, and by dividing the distance traveled in those five seconds by five seconds, a coarse measure of speed is determined. Other timed measurements could be made as a matter of design choice, e.g., ½, 1, 15, 20, 25, 30 or 60 seconds. By taking fewer measurements, and by reducing processing, battery power is conserved over the course of a day, as it is preferable that the ticket determines speeding violations for at least a full day, in Winter. Finely determining speed at about one-second intervals is useful in the preferred embodiment of the invention.

Memory 236' may further define location information relative to one or more "zones" at a resort, such that speed may be assigned to each zone. In this manner, for example, a resort can specify that ski run "X" (of zone "A") has a speed limit of 35 mph, while ski run "Y" (of zone "B") has a speed limit of 30 mph. Speeding violations within any of zones A or B are then communicated to the resort. The advantage of this feature of the invention is that certain slopes or mountain areas permit higher speeds, and yet other slopes (e.g., a tree skiing area) do not support higher speeds. The resort may for example specify speed limits according to terrain. GPS receiver 243 determines earth position—which processor 235' determines is within a particular zone—and speed violations are then determined relative to the speed limit within the particular zone, providing a more flexible system for the ski resort.

Position locator 243 of another embodiment is an altimeter, preferably including a solid-state pressure sensor. Altimeter 243 of one embodiment provides gross position information such as the maximum and minimum altitude on a ski mountain. For a particular resort, maximum and minimum altitude approximately correspond to a distance of "Z" meters, the distance needed to traverse between the minimum and maximum altitude. Processor 235' then determines speed based upon dividing Z by the time between determining the minimum and maximum altitudes. Fractional speeds may also be determined. If for example a particular skier traverses between a maximum altitude and half-way between the minimum and maximum altitudes, then processor 235' determines speed based upon dividing Z/2 by the time between determining (a) the maximum altitude and (b) the midpoint between the minimum and maximum altitudes.

Figure 11:
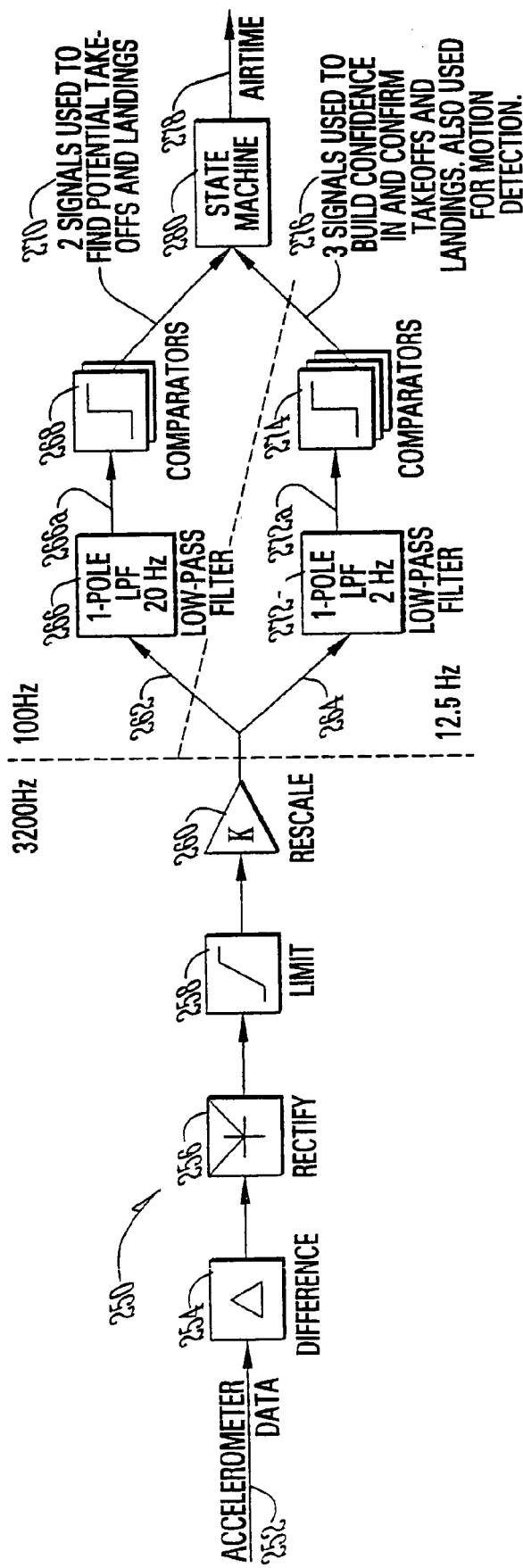
FIG. 11 schematically shows an electrical logic and process flow chart for use with determining "airtime" in accord with the invention.
Figure 12:
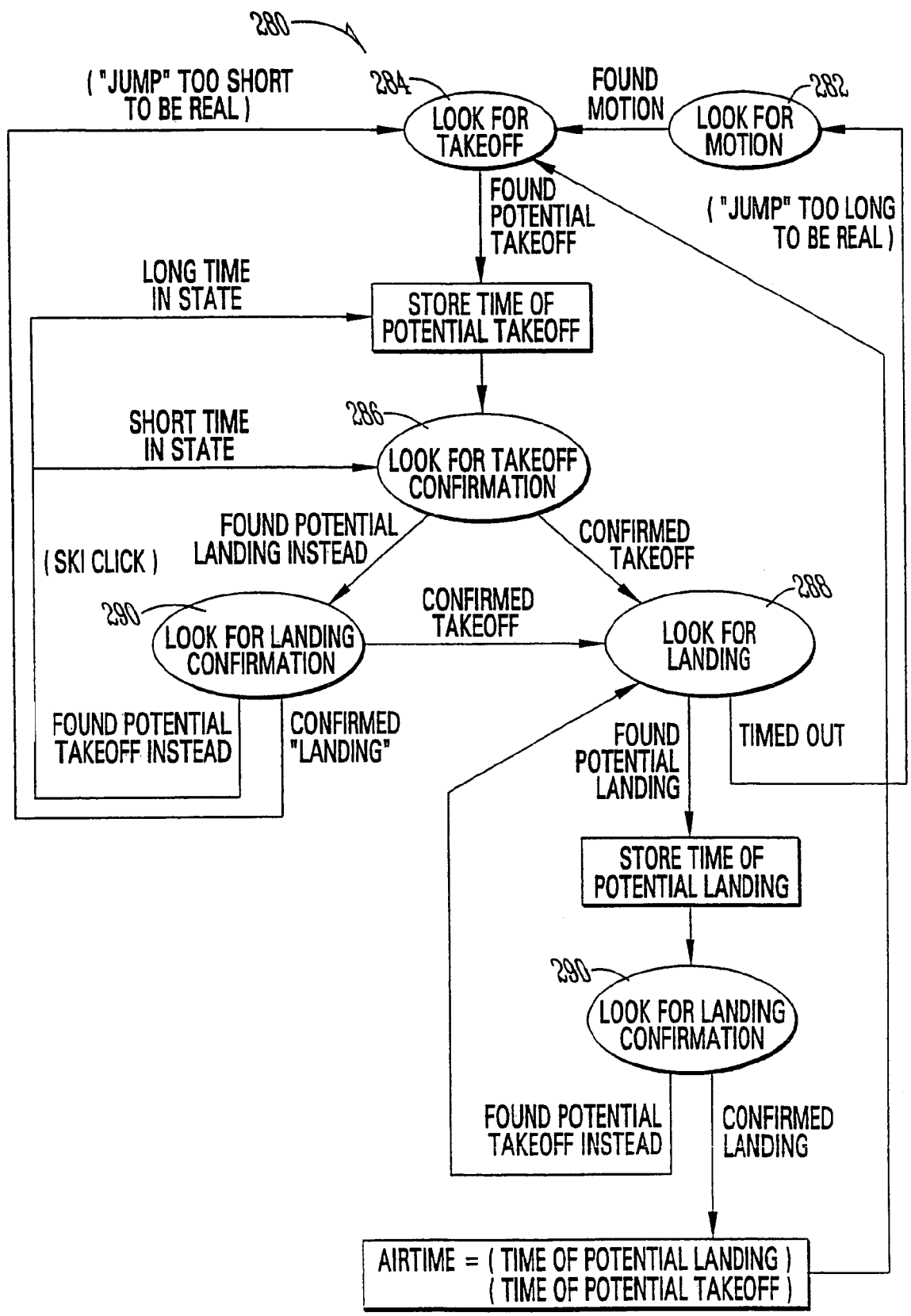
FIG. 12 schematically shows a state machine used in association with determining airtime in association with an algorithm such as in FIG. 11.

As discussed above, one MMD of the invention includes an airtime sensor. FIG. 11 and FIG. 12 collectively illustrate the preferred embodiment for determining and detecting airtime in accord with the invention. A MMD configured to measure airtime preferably uses an accelerometer as the detector; and FIG. 11 depicts electrical and process steps 250 for processing acceleration signals to determine an "airtime" event. FIG. 12 illustrates state machine logic 280 used in reporting this airtime. By way of example, FIG. 12 shows that motion is preferably determined prior to determining airtime, as airtime is meaningful in certain applications (e.g., wakeboarding) when the vehicle (e.g., the wakeboard) is moving and non-stationary.

More particularly, FIG. 11 depicts discrete-time signal processing steps of an airtime detection algorithm. Acceleration data 252 derive from a detector in the form of an accelerometer. Two pseudo-power level signals 266a, 272a are produced from data 252 by differentiating (step 254), rectifying (step 256), and then filtering through respective low-pass filters at steps 266 or 272. More particularly, a difference signal of data 252 is taken at step 254. The difference signal for example operates to efficiently filter data 252. The difference signal is next rectified, preferably, at step 256. Optionally, a limit filter serves to limit rectified data at step 258. Rectified, limited data may be rescaled, if desired, at step 260. The limiting and rescaling steps 258, 260 help reduce quantization effects on the resolution of power signals 266a, 272a. Filtering at steps 266, 272 incorporate different associated time constants, and feed binary hysteresis functions with different trigger levels, to produce "power" signals 266a, 272a.

More particularly, data from step 260 is bifurcated along fast-signal path 262 and slow-signal path 264, as shown. In path 262, a low pass filter operation (here shown as a one pole, 20 Hz low pass filter) first occurs at step 266 to produce power signal 266a. Two comparators compare power signal 266a to thresholds, at step 268, to generate two signals 270 used to identify possible takeoffs and landings for an airtime event. In path 264, a low pass filter operation (here shown as a one pole 2 Hz low pass filter) first occurs at step 272 to produce power signal 272a. Three comparators compare power signal 272a to thresholds, at step 274, to generate three "confidence" signals 276 used to assess confidence of takeoffs and landings for an airtime event. Finally, a state machine 280, described in more detail in FIG. 12, evaluates signals 270, 276 to generate airtime events 278.

Those skilled in the art should appreciate that the airtime detection scheme of FIG. 11 also may be used for other detectors, such as those in the form of piezoelectric strips and microphones, without departing from the scope of the invention.

FIG. 12 schematically shows state machine logic 280 used to report and identify airtime events, in accord with the invention. State machine 280 includes several processes, including determining motion 282, determining potential takeoffs 284 (e.g., of the type determined along path 262, FIG. 11), determining takeoff confirmations 286 (e.g., of the type determined along path 264, FIG. 11), determining potential landings 288 (e.g., of the type determined along path 262, FIG. 11), and determining landing confirmations 290 (e.g., of the type determined along path 264, FIG. 11). Logic flow between processes 282, 284, 286, 288, 290 occurs as illustrated and annotated according to the preferred embodiment of the invention.

In summary, the relative fast signal from fast-signal path 262, FIG. 11, isolates potential takeoffs and potential landings from data 252 with timing accuracy (defined by filter 266) that meets airtime accuracy specifications, e.g., $1/100^{th}$ of a second. The drawback of detections along path 262 is that it may react to accelerometer signal fluctuations that do not represent real events, which may occur with a ski click in the middle of an airtime jump by a skier. This problem is solved by confirming potential takeoffs and landings with confirmation takeoffs and landings triggered by a slower signal, i.e., along path 264. The slower signal 272a is thus used to confirm landings and takeoffs, but is not used for timing because it does not have sufficient time resolution.

An accelerometer signal described in FIG. 11 and FIG. 12 is preferably sensitive to the vertical axis (i.e., the axis perpendicular to the direction of motion, e.g., typically the direction of forward velocity, such as the direction down a hill for a snowboarder) to produce a raw acceleration signal (i.e., data 252, FIG. 11) for processing. Other accelerometer orientations can also be used effectively. The raw acceleration signal may for example be sampled at high frequencies (e.g., 4800 Hz) and then acted upon by the algorithm of FIG. 11. With a stream of accelerometer data, the algorithm produces an output stream of time-tagged airtime events.

Figure 13:
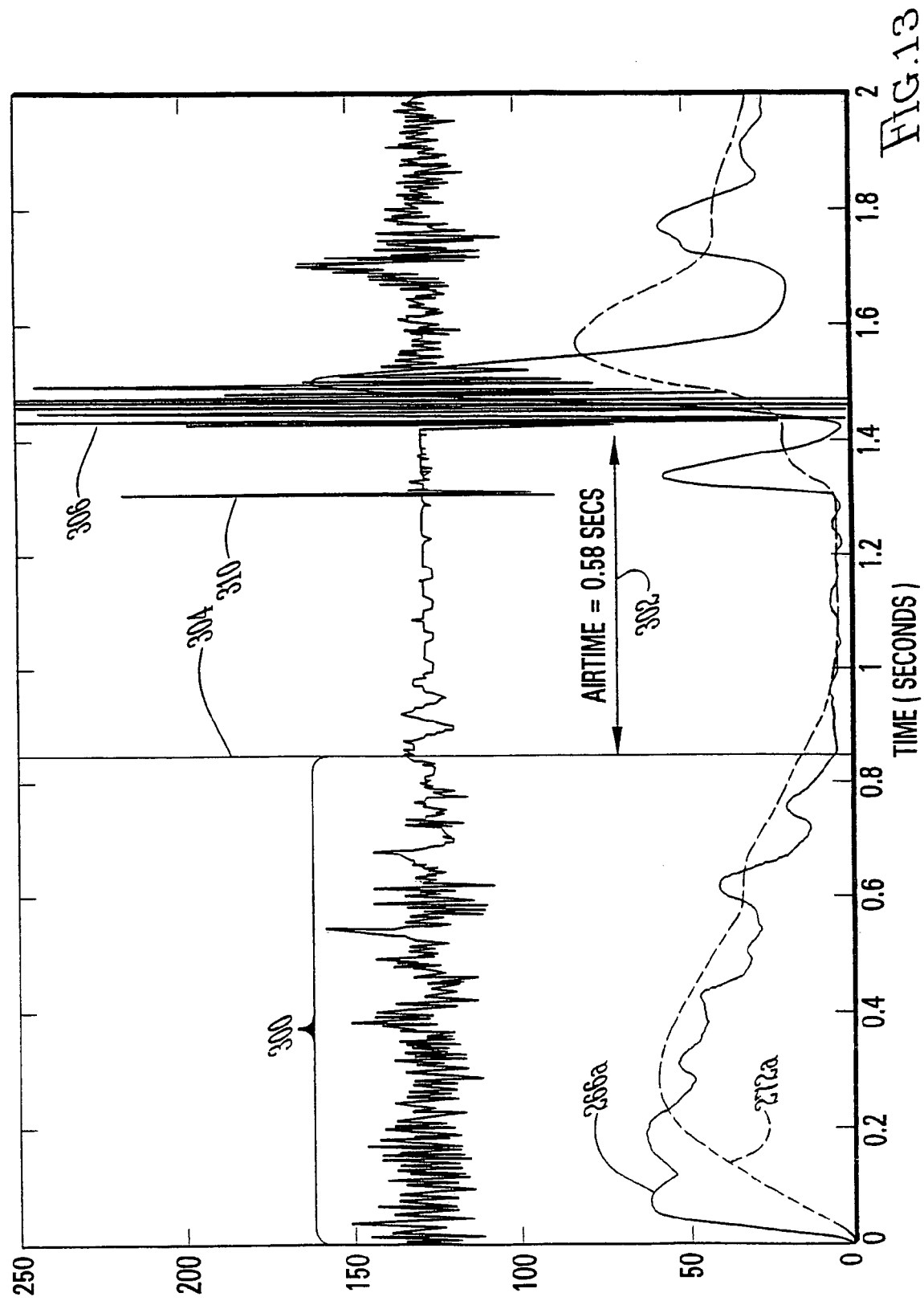
FIG. 13 graphically shows accelerometer data and corresponding process signals used to determine airtime in accord with preferred embodiments of the invention.

FIG. 13 graphically shows representative accelerometer data 300 captured by a device of the invention and covering an airtime event 302. Event 302 occurs between takeoff 304 and landing 306, both determined through the algorithm of FIG. 11. Data representing power signals 266a and 272a are also shown. A ski click 310 illustrating the importance of signals 266a, 272a shows how the invention prevents identification of ski click 310 as a landing or second takeoff.

Data transmission from a sensor (e.g., a MMD) to a display unit (e.g., a receiver) is generally at least 99.9% reliable. In the case of one-way communication, a redundant transmission protocol is preferably used to cover for lost data transmissions. Communications are also preferably optimized so as to reduce battery consumption. One way to reduce battery consumption is to synchronize transmission with reception. The "transmission period" (the period between one transmission and the next), the size of the storage buffer in sensor memory, and the number of times data is repeated (defining a maximum age of an event) are adjustable to achieve battery consumption goals.

Figure 14:
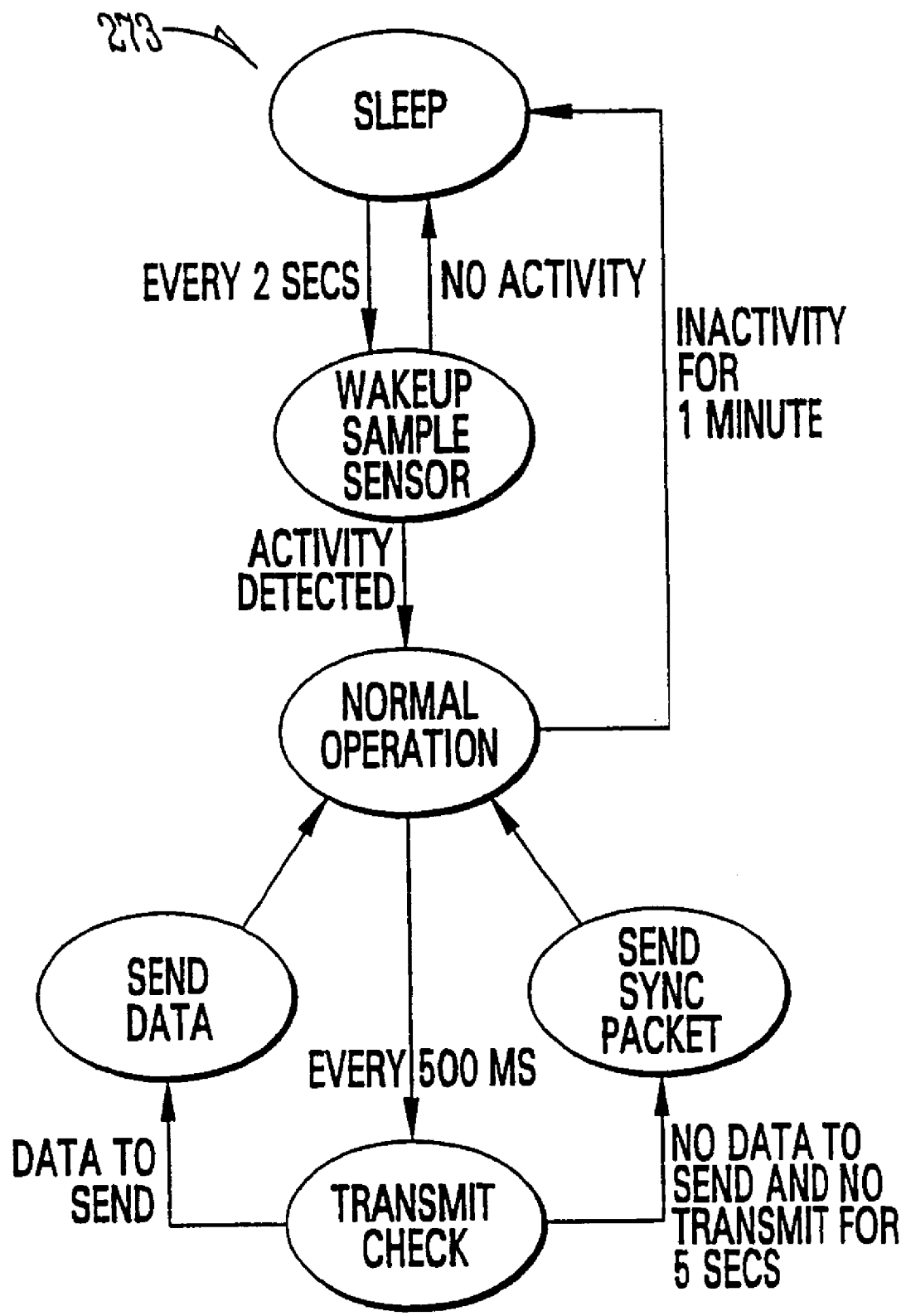
FIG. 14 and FIG. 14A shows a state diagram illustrating one-way transmission protocols according to one embodiment of the invention.
Figure 14A:
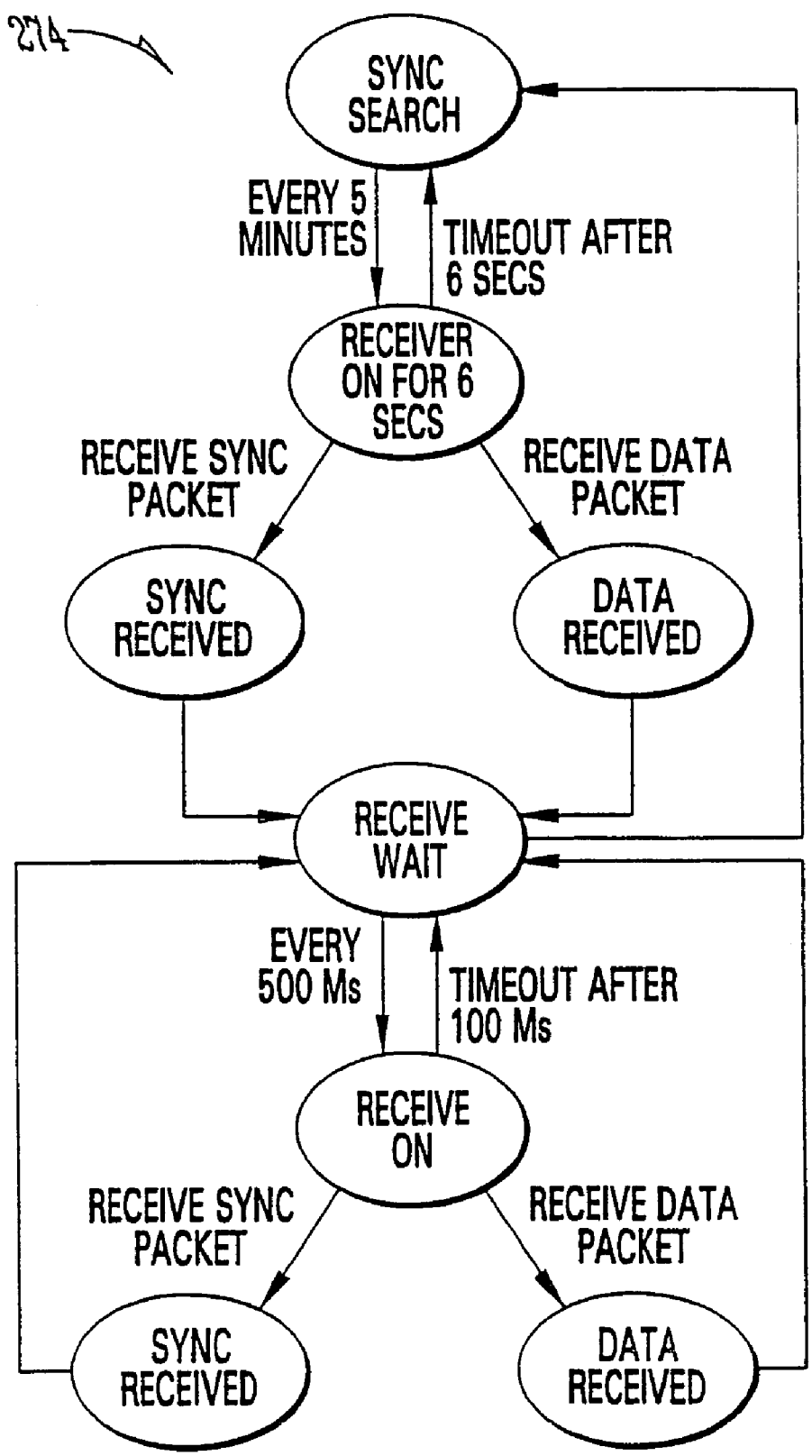

A state diagram for transmission protocols between one sensor and display unit, utilizing one-way transmission, is shown in FIG. 14 and FIG. 14A. FIG. 14 and FIG. 14A specifically show the operational state transitions for the sensor (chart 273) and display unit (chart 274) with respect to transmission protocols, in one embodiment of the invention. The numerical times provided in FIG. 14 are illustrative, without limitation, and may be adjusted to optimize performance. As those skilled in the art should appreciate, alternative protocols may be used in accord with the invention between sensors and receivers. With reference to FIG. 14 and FIG. 14A, the display unit is generally in a low power mode unless receiving data, to conserve power in the display unit. To accomplish this, transmissions between the sensor and display unit are synchronized such that the display unit knows when the sensor can next transmit. When the sensor has no data to transmit, there preferably is no transmission; however, synchronization is still maintained by short transmissions. Synchronization need not be performed at each transmission period, but preferably at a suitably spaced multiple of the transmission period. The period between synchronization-only transmissions is then determined by the amount of clock drift between the display unit and the sensor unit. The sync-only transmission may include the power up sequence and the sync byte, such that the display unit maintains sync with sensor transmissions. The transmission period is preferably selectable by software for both the sensor and the display unit.

By way of example, one sensor unit is monitor device 10 of FIG. 1, and one display unit is receiver 24 of FIG. 1. When the sensor and receiver function as a pair, the sensor unit preferably has an identification (ID) number communicated to the display unit in transmission so that the display unit only decodes data from one particular sensor.

Preferably, the display unit determines the sync pattern for sensor transmissions by active listening until receipt of a synchronization or data transmission with the matching sensor ID. Once a valid transmission from the matching sensor is received, the display unit calculates the time of the next possible transmission and controls the display unit accordingly. When the sensor is a MMD used to determine airtime, and the sensor does not necessarily have a real time clock;

data sent to the display unit includes airtime values with time information as to when the airtime occurred. As this sensor does not necessarily maintain a real time clock, the time information sent from the sensor is relative to the packet transmission time. Preferably, the display unit, which has a real time clock, will convert the relative time into an absolute time such that airtime as an event is tagged with appropriate time and/or date information.

The amount of data communicated between the sensor and display unit varies. By way of example, for typical skier and snowboarder operation, an airtime event covering the 0-5 second range with a resolution of $\frac{1}{100}^{th}$ second is generally adequate. The coding of such airtime events can use nine data bits. Ten bits allow for measurement of up to approximately ten seconds, if desired. For an age, where the resolution of age is one second (i.e., a time stamp resolution) and the maximum age of a repeat transmission is fifteen seconds, four bits are used. Data transmission also typically has overhead, such as startup time, synchronization byte, sensor ID used to verify correct sensor reception, a product identifier to allow backwards compatibility in future receivers, a count of the number of data items in the packet, and, following the actual data, a checksum to gain confidence in the received data. This overhead is approximately six bytes in length. To reduce the effect of overhead, stored data in the sensor is preferably sent in one message. An airtime event for example can be stored in the sensor until transmitted with the desired redundancy, after which it is typically discarded. Thus, the number of airtime events included in a transmission depends upon the number of items still in the sensor's buffer (e.g., in memory 20, FIG. 1). When the buffer is empty, there is, generally, no data transmission.

A typical data transmission can for example include: <P/up> <Sync><Sensor ID> <Product ID> <Count> [<Age> <Airtime>] <Checksum>. <P/up> is the power-up time for the transmitter. A character may be transmitted during power up to aid the transmitter startup, and help the receiver start to synchronize on the signal. The <Sync> character is sent so that the receiver can recognize the start of a new message. <Sensor ID> defines each sensor with a unique ID number such that the display unit can selectively use data from a matching sensor. <Product ID> defines each sensor with a product ID to allow for backward compatibility in future receivers. <Count> defines how many age/airtime values are included in a message. The <Age> field provides the age of an associated airtime value, which may be used by the display unit to identify when an airtime is retransmitted. <Airtime> is the actual airtime value. <Checksum> provides verification that the data was received correctly.

A sensor's buffer length should accommodate the maximum number of airtime jumps for the duration of retransmissions. By way of example, transmissions can be restricted so that no more than one jump every three seconds is recognized; and retransmissions should generally finish within a selected time interval (e.g., six seconds). Therefore, this exemplary sensor need only store two airtime events at any one time. The buffer length is preferably configurable, and can for example be set to hold four or more airtime events.

Transmission electronics within the sensor and display units may use a UART, meaning that data is defined in byte-sized quantities. As those skilled in the art understand, alternative transmission protocols can utilize bit level resolution to further reduce transmission length.

By way of example, consider an airtime event of 1.72 seconds, occurring 2.1 seconds before start of transmission. In accord with FIG. 14 and FIG. 14A, the transmitted data would be as follows:

<P/up> <Sync> <Sensor ID> <Product ID> <Count> [<Age> <Airtime>]<Checksum> <0xAA> <0xAD> <0x12><0x01><0x01><0x02><0x 158><0x21>

Assuming that the age and airtime data are combined into two bytes, and that <P/up> is one byte in length, the entire packet is eight bytes in length. At a transmission speed of 1200 baud, a typical transmission speed between a sensor and receiver, the eight bytes takes 67 ms to transmit. Assuming sequential transmission periods of 500 ms, the transmission duty cycle is 13.4% for a single jump.

Those skilled in the art should appreciate that alternatives from the above-described protocols may be made without departing from the scope of the invention. In one alternative, pseudo random transmissions are used between a sensor and receiver. If for example two sensors are together, and transmitting, the transmissions may interfere with one another if both transmissions synchronously overlap. Therefore, in situations like this, a pseudo random transmission interval may be used, and preferably randomized by the unique sensor identification number <Sensor ID>. If both the display unit and the sensor follow the same sequence, they can remain in complete sync. Accordingly, a collision of one transmission (by two adjacent sensors) will likely not occur on the next transmission. In another alternative, it may also be beneficial for the receiver to define a bit pattern for the <Sync> byte that does not occur anywhere else in the transmitted data, such as used, for example, with the HDLC bit stuffing protocol. In another alternative, it may be beneficial to use an error correction protocol, instead of retransmissions, to reduce overall data throughput. In still another alternative, a more elaborate checksum is used to reduce the risk of processing invalid data.

In still another alternative, a "Hamming Code" may be used in the transmission protocol. Hamming codes are typically used with continuous streams of data, such as for a CD player, or for the system described in connection with FIG. 8; however they are not generally used with event or timed sequence transmissions described in connection with FIG. 14. Nevertheless, Hamming codes may make the data paths more robust. The wireless receiver in the display unit may take a finite time in start-up before it can receive each message. Since a further goal of the transmission protocol is generally to reduce the overall number of transmissions from the sensor, it may be beneficial to add additional data to the transmission and send it fewer times rather than to retransmit data several times. For example, rather than sending all buffered airtime values with each transmission, two data items can be sent, together with a count of airtimes in the sensor buffer, and a sum of the airtimes. If the display unit misses one airtime (e.g., determined by the count value), it can use the sum value received and the summation of the airtimes it has previously received to determine the missing airtime. A similar scheme can be used for age values so as to determine the time of the missing airtime.

The display unit receiver is typically in the physical form of a watch, pager, cell phone or PDA; and, further, receivers also typically have corresponding functionality. By way of example, one receiver is a cell phone that additionally functions as a receiver to read and interpret data from a MMD. Furthermore, a display unit is preferably capable of receiving and displaying more than one movement metric. As such, data packets described above preferably include the additional metric data, e.g., containing both impact and airtime event data. Display units of the invention preferably have versatile attachment options, such as to facilitate attachment to a wrist (e.g., via a watch or Velcro strap for over clothing), a neck (e.g., via a necklace), or body (e.g., by a strap or belt).

Sensors such as the monitor devices described above, and corresponding display unit receivers, preferably have certain characteristics, and such as to accommodate extreme temperature, vibration and shock environments. One representative sensor and receiver used to determine airtime in action sports can for example have the following non-limiting characteristics: sensor attaches to a flat surface (e.g., to snowboard, ski, wakeboard); sensor stays attached during normal aggressive use; display unit attachable to outside of clothing or gear; waterproof; display unit battery life three months or more; sensor battery life one week or more of continuous use; on/off functionality by switch or automatic operation; characters displayed at data unit visible from a minimum of eighteen inches; minimum data comprehension time for data minimum of 0.5 second; last airtime data accessible with no physical interaction; one second maximum time delay for display of airtime data after jump; displayed data readable in sunlight; displayed data includes time and/or date information of airtime; user selection of accumulated airtime; display unit provides real time information; display unit operable with a maximum of two buttons; physical survivability for five foot drop onto concrete; scratch and stomp resistant; no sharp edges; minimum data precision $1/30^{th}$ second; minimum data accuracy $1/5^{th}$ second; minimum data resolution $1/100^{th}$ second; minimum data reliability 999/1000 messages received; algorithm performance less than one percent false positive and less then two percent false negative indications per day; and temperature range minimum of −10 C-60 C.

Those skilled in the art should appreciate that the above description of communication protocols of "airtime" between sensor and receiver can be applied to monitor devices sensing other metrics, e.g., temperature, without departing from the scope of the invention.

Figure 15:
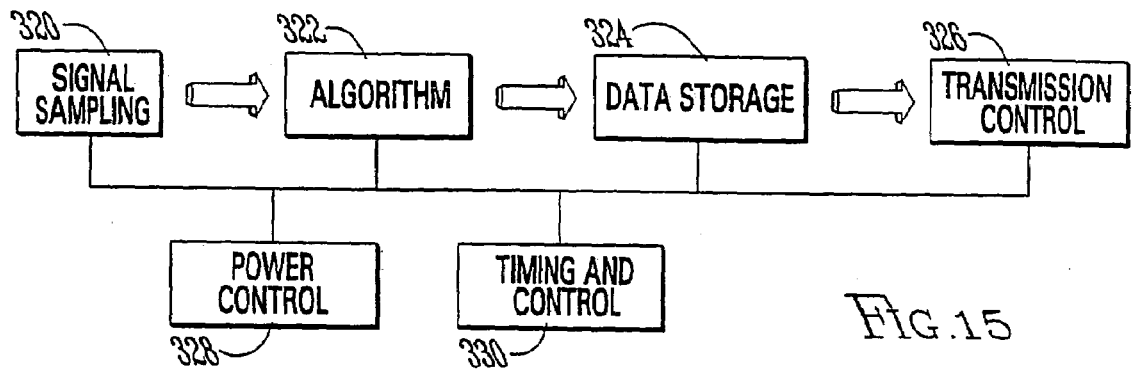
FIG. 15 schematically illustrates functional blocks for one sensor of the invention.
Figure 16:
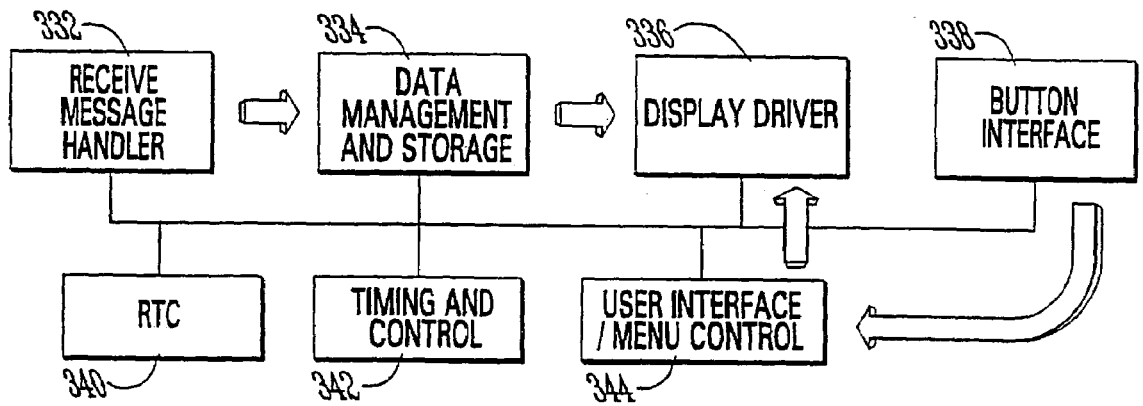
FIG. 16 schematically illustrates functional blocks for one display unit of the invention.

By way of example, FIG. 15 shows functional blocks 320, 322, 324, 326, 328, 330 of one sensor of the invention. The sensor's algorithm analyses signals from an internal detector and determines an event such as airtime. This event information is stored and made ready for transmission to the display unit. FIG. 16 shows functional blocks 332, 334, 336, 338, 340, 342, 344 of one display unit of the invention. Transmission protocols between functional blocks 326, 332 ensure that data is received reliably. The internal detector of the sensor of FIG. 15 for example is an accelerometer oriented to measure acceleration in the Z direction (i.e., perpendicular to the X, Y plane of motion). Signals generated from the detector are sampled at a suitable frequency, at block 320, and then processed by an event algorithm, at block 322. The algorithm applies filters and control logic to determine event, e.g., the takeoff and landing times for airtime events. Event data such as airtime is passed to the data storage at block 324. Data is stored to meet transmission protocol requirements; preferably, data is stored in a cyclic buffer, and once all data transmissions are performed, the data is discarded. Transmission can be performed by a UART, at block 326, where data content is arranged to provide sufficient robustness. Power control at block 328 monitors signal activity level to determine if the sensor should be in 'operating' mode, or in 'sleep' mode. Sleep mode preserves the battery to obtain a greater operative life. While in sleep mode, the processor wakes periodically to check for activity. Timing and control at block 330 maintains timing and scheduling of software components.

With regard to FIG. 16, receiver message handler at block 332 performs data reconstruction and duplication removal from transmission protocols. Resulting data items are sent to data management and storage at block 334. Stored data ensures that the user can select desired information for display, at block 336. The display driver preferably performs additional data processing, such as in displaying Total Lists (e.g., values representing cumulative of a metric), Best lists (e.g., values representing the best or highest or lowest metric), and Current Lists (e.g., values representing latest metric). These lists are filled automatically, but may be cleared or reset by the user. Buttons typically control the display unit, at block 338. Button inputs by users are scanned for user input, with corresponding information passed to the user interface/menu control block 344. The display driver of block 336 selects and formats data for display, and sends it to the receiver's display device (e.g., an LCD). This information may also include menu items to allow the user select, or perform functions on, stored data, or to select different operation modes. A real time clock of block 340 maintains the current time and date even when the display is inactive. The time and date is used to time stamp event data (e.g., an airtime event). Timing and control at block 342 maintains timing and scheduling of various software components. User interface at block 344 accepts input from the button interface, to select data items for display. A user preferably can scroll through menu items, or data lists, as desired.

FIG. 17 shows one housing suitable for use with a monitor device (e.g., a MMD) of the invention. The housing is shown with three pieces: a top element 362, a bottom element 364, and an o-ring 366. As shown in FIG. 18, elements 362, 364 form a watertight seal with o-ring 366 to form an internal cavity that contains and protects sensor electronics 368 (e.g., detector 12, processor 14, communications port 16 of FIG. 1) disposed within the cavity. Batteries 370 power sensor electronics 368, such as described in connection with FIGS. 3F, 3G. In combination, the housing is preferably small, with volume dimensions less than about 35 mm×15 mm×15 mm. Generally, one dimension of the housing is longer than the other dimensions, as illustrated; though this is not required.

Figure 20:
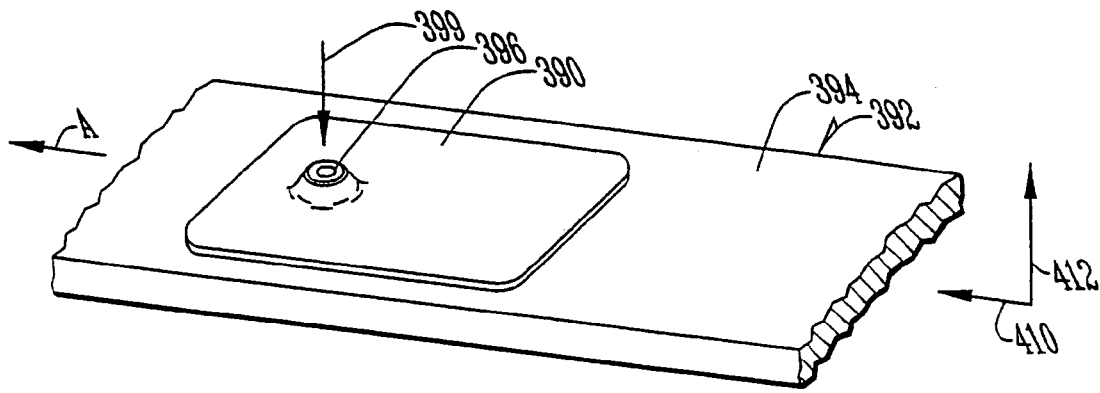
FIG. 20 shows one vehicle and vehicle attachment bracket to which the housing of FIG. 19 attaches.
Figure 21:
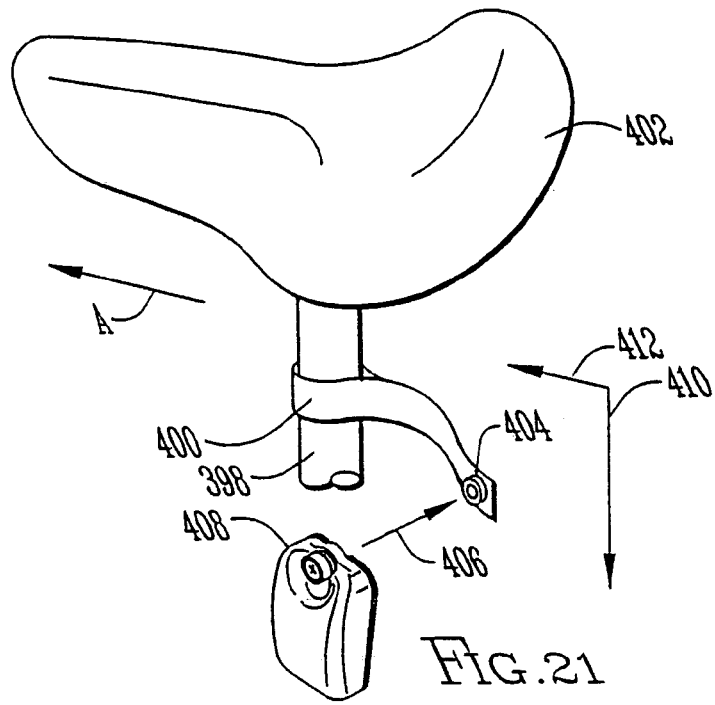
FIG. 21 shows another vehicle and vehicle attachment bracket to which the housing of FIG. 19 attaches.

FIG. 19 shows an alternative housing 372 suitable for use with a sensor (e.g., a MMD) of the invention. Housing 372 is shown with three pieces: a top element 374, a bottom element 376, and an o-ring 378. As above, elements 374, 376 form a watertight seal with o-ring 378 to form an internal cavity that contains and protects sensor electronics disposed therein. FIG. 19 also shows housing 372 coupled to sensor bracket 380. A mating screw 382 passes through housing 372, as shown, and through sensor bracket 380 for attachment to a vehicle attachment bracket. FIG. 20 illustrates one vehicle attachment bracket 390; FIG. 21 illustrates another vehicle attachment bracket 400. Mating screw 382 preferably has a large head 382a so that human fingers can efficiently manipulate screw 382, thereby attaching and detaching housing 372 from the vehicle attachment bracket, and, thereby, from the underlying vehicle. Screw 382 also preferably clamps together elements 374, 376, 378 at a single location to seal sensor electronics within housing 372.

Bracket 390 of FIG. 20 attaches directly to vehicle 392. Vehicle 392 is for example a sport vehicle such as a snowboard, ski, wakeboard, or skateboard. Vehicle 392 may also be part of a car or motorcycle. A surface 394 of vehicle 392 may be flat; and thus bracket 390 preferably has a corresponding flat surface so that bracket 390 is efficiently bonded, glued, screwed, or otherwise attached to surface 394. Bracket 390 also has screw hole 396 into which mating screw 382 threads to, along direction 399.

FIG. 21 shows one alternative vehicle attachment bracket 400. Bracket 400 has an L-shape to facilitate attachment to bicycle frame 398. Frame 398 is for example part of a bicycle or mountain biking sports vehicle. A seat 402 is shown for purposes of illustration. Bracket 400 has a screw hole 404 into which mating screw 382 threads to, along direction 406. Sensor outline 408 illustrates how housing 372 may attach to bracket 400.

Brackets 380, 390, 400 illustrate how sensors of the invention may beneficially attach to sporting vehicles of practically any shape, and with low profile once attached thereto. The brackets of the invention preferably conform to the desired vehicle and provide desired orientations for the sensor within its housing. By way of example, L-shaped bracket 400 may be used to effectively orient a sensor to bike 398. If for example the sensor includes a two-axis accelerometer as the detector, with sensitive axes 410, 412 arranged as shown, then vehicle vibration substantially perpendicular to ground (i.e., ground being the plane of movement for the vehicle, illustrated by vector A) may be detected in sensor orientations illustrated by attachment of housing 372 to attachments 390, 400 of FIGS. 20 and 21, respectively. In addition, such an arrangement provides for mounting the sensor to a vehicle with a low profile extending from the vehicle.

Vehicle attachment brackets (and sensor brackets) are preferably made with sturdy material, e.g., Aluminum, such that, once attached to a vehicle (e.g., vehicle 390 or 398), the vibration characteristics of the underlying vehicle transmit through to the housing attached thereto; the sensor within the housing may then monitor movement signals (e.g., vibration of the vehicle, generally generated perpendicular to "A" in FIG. 20 and FIG. 21) directly and with little signal loss or degradation.

Figure 22:
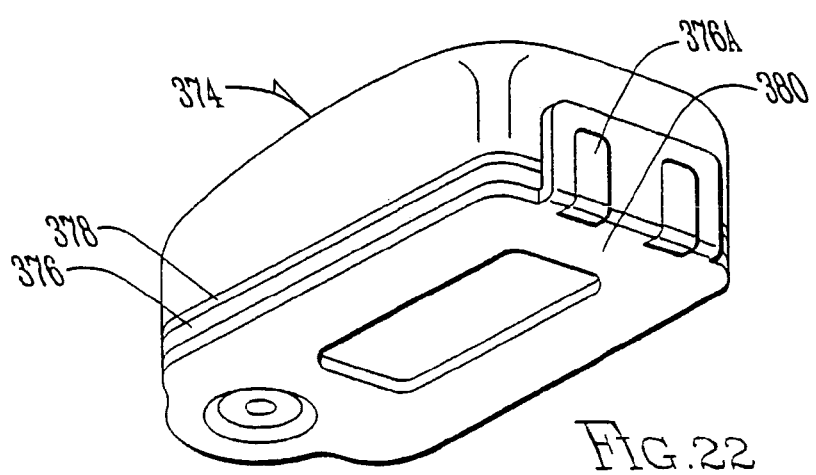
FIG. 22 shows a bottom perspective view of the housing of FIG. 19.
Figure 23:
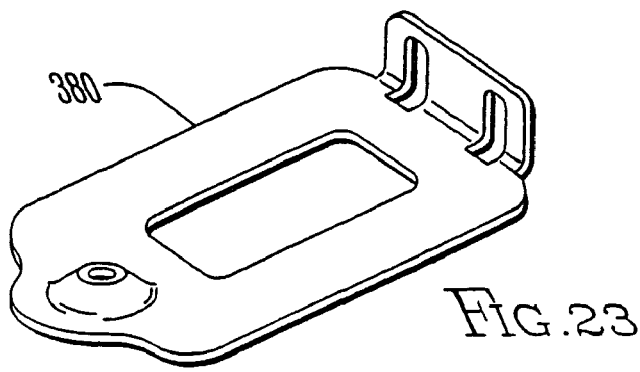
FIG. 23 shows a bracket constructed according to the invention and made for attachment between the housing of FIG. 19 and a vehicle attachment bracket.
Figure 24:
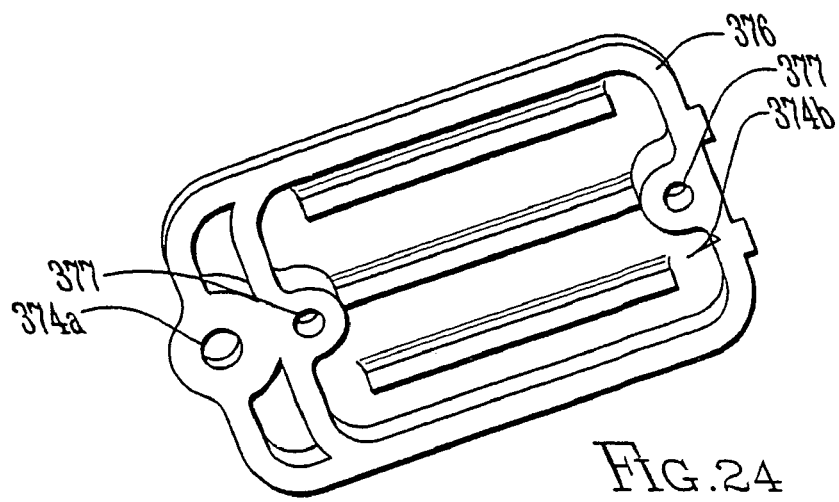
FIG. 24 shows a top element of the housing of FIG. 19.
Figure 25:
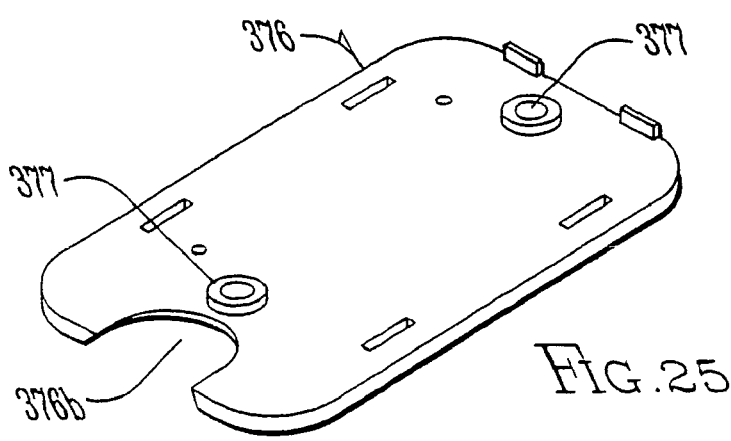
FIG. 25 shows a bottom element of the housing of FIG. 19.

FIG. 22 shows housing 374 from a lower perspective view, and specifically shows sensor bracket 380 configured with back connecting elements 376a of housing element 376. FIG. 23 further illustrates bracket 380. FIG. 24 further illustrates element 374, including screw hole 374a for mating screw 382, and in forming part of the cavity 374b for sensor electronics. FIG. 25 further illustrates element 376, including screw aperture 376b for mating screw 382. Elements 376, 374 may optionally be joined together via attachment channels 377, with screws or alignment pins.

Figure 26:
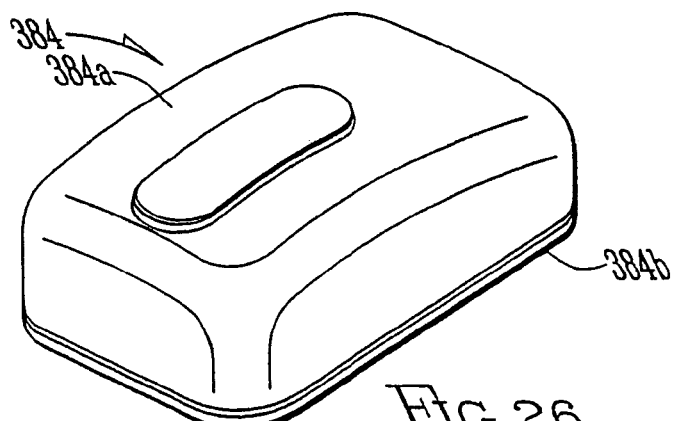
FIG. 26 shows a perspective view of one housing constructed according to the invention.
Figure 27:
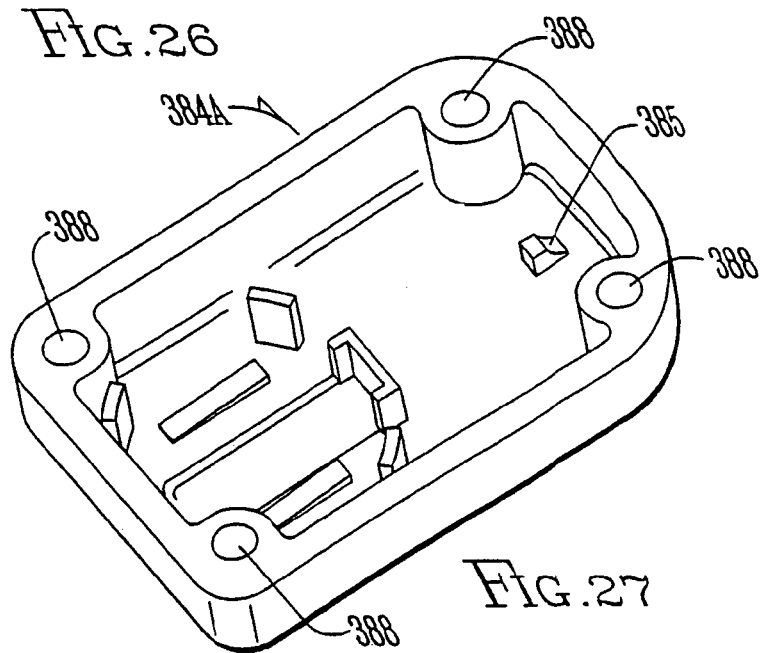
FIG. 27 shows a perspective view of a top portion of the housing of FIG. 26.
Figure 28:
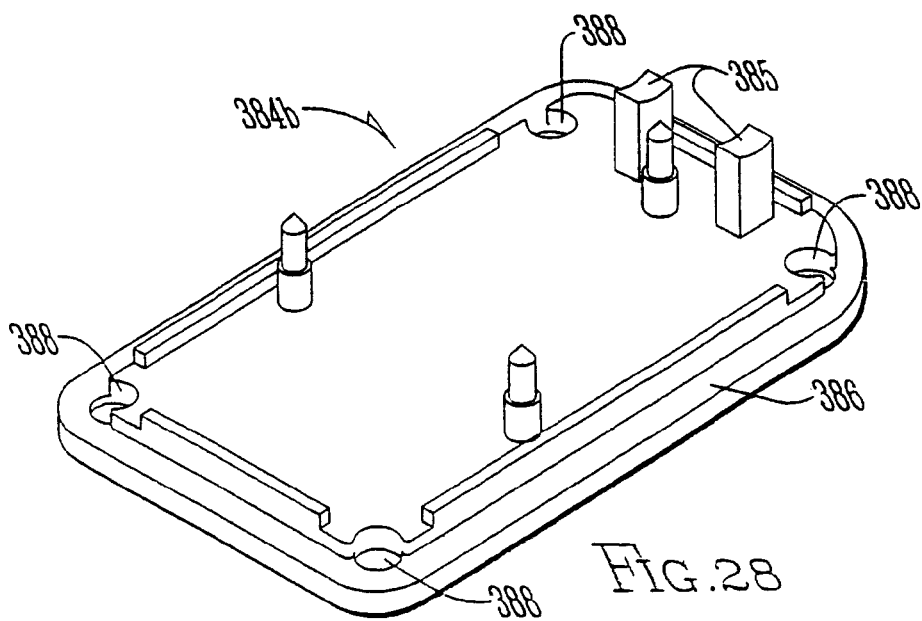
FIG. 28 shows a perspective view of a bottom portion of the housing of FIG. 27.
Figure 29:
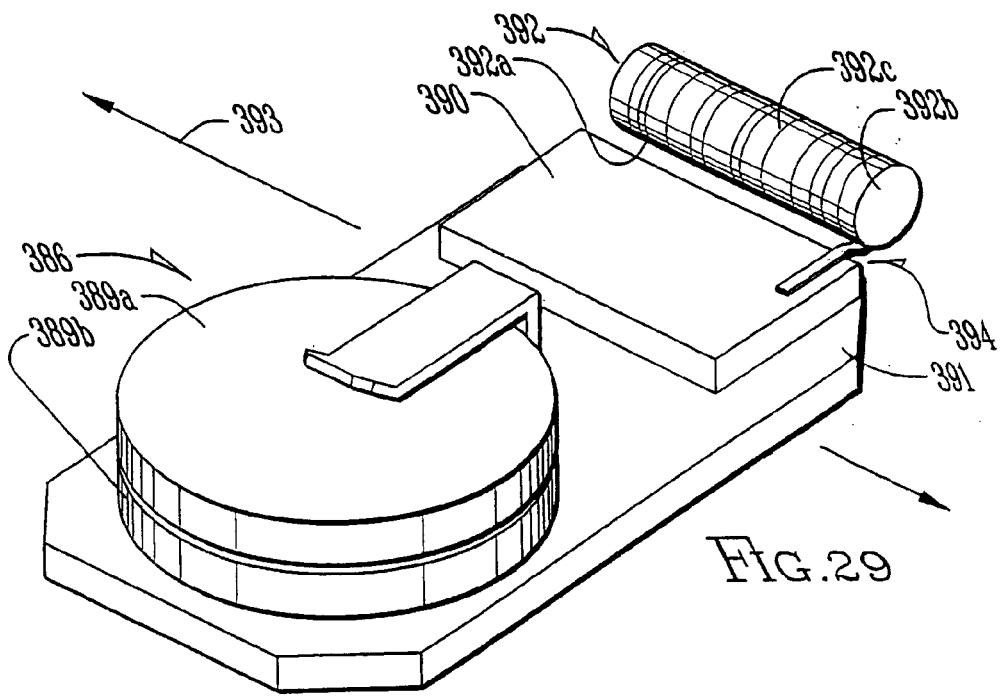
FIG. 29 shows a perspective view of one monitor device constructed according to the invention for operational placement within the housing of FIG. 26.

FIG. 26 shows one housing 384 for a monitor device of the invention. Housing 384 is preferably made from mold urethane and includes a top portion 384a and bottom portion 384b. An o-ring (not shown) between portions 384a, 384b serves to keep electronics within housing 384 dry and free from environmental forces external to housing 384. FIG. 27 shows the inside of top portion 384a; FIG. 28 shows the inside of bottom portion 384b; and FIG. 29 shows one monitor device 386, constructed according to the invention, for operational placement within housing 384. Portions 384a, 384b are clamped together by screw attachment channels 388. In FIG. 29, device 386 includes batteries 389a, 389b used to power a radio-frequency transmitter 390 and other electronics coupled with PCB 391. Data from device 386 is communicated to remote receivers through antenna 392. When transmitter 390 is a 433 MHz transmitter, for example, antenna 392 is preferably coil-shaped, as shown, running parallel to the short axis 393 of PCB 391 and about 4.5 mm above the non-battery edge 394 of PCB 391. Coil antenna 392 is preferably about 15 mm long along length 392a and about 5.5 mm in diameter along width 392b; and coil antenna 392 is preferably made from about 20 turns 392c of enameled copper wire. Antenna 392 may be coupled to housing 384 via protrusions 385. The o-ring between portions 384a, 384b may be placed on track 386.

Figure 30:
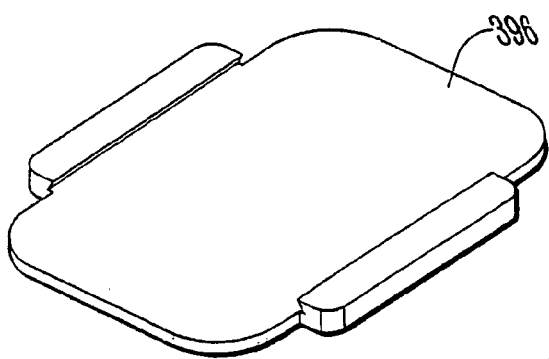
FIG. 30 shows a mounting plate for attaching monitor devices to flat surfaces in accord with one embodiment of the invention.
Figure 31:
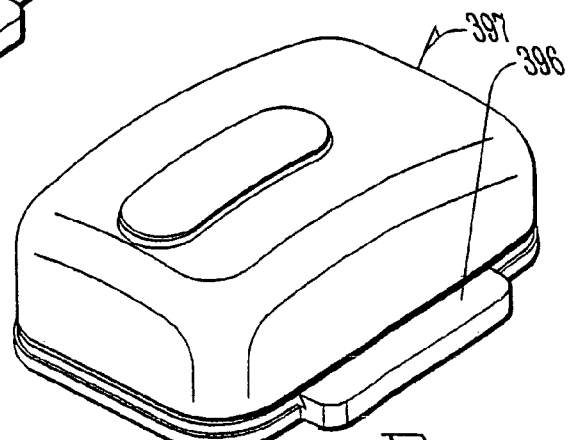
FIG. 31 shows a perspective view of the plate of FIG. 30 with a monitor device coupled thereto.
Figure 32:
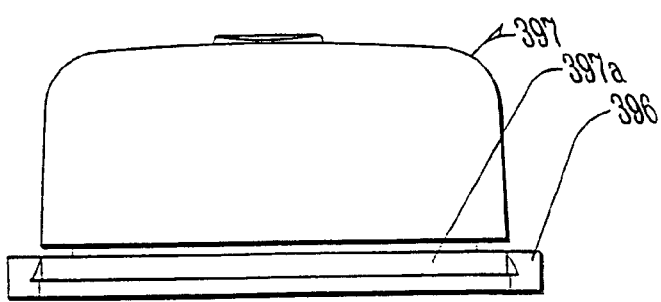
FIG. 32 shows an end view of the plate and device of FIG. 31.

FIG. 30, FIG. 31 and FIG. 32 collectively illustrate one mounting system for attaching monitor devices of the invention to objects with flat surfaces. FIG. 30 shows a plate 396 that is preferably injection molded using a tough metal replacement material such as the Verton™. Plate 396 is preferably permanently secured to the flat surface (e.g., to a ski or snowboard) with 3M VHB tape or other glue or screw. Skis, bicycles, and other vehicles use a corresponding shaped plate that accepts the same sensor. FIG. 31 shows plate 396 in perspective view with a monitor device 397 of the invention. FIG. 32 shows an end view illustrating how plate 396 couples with device 397, and particularly with a lower portion 397a of device 397.

Figure 33:
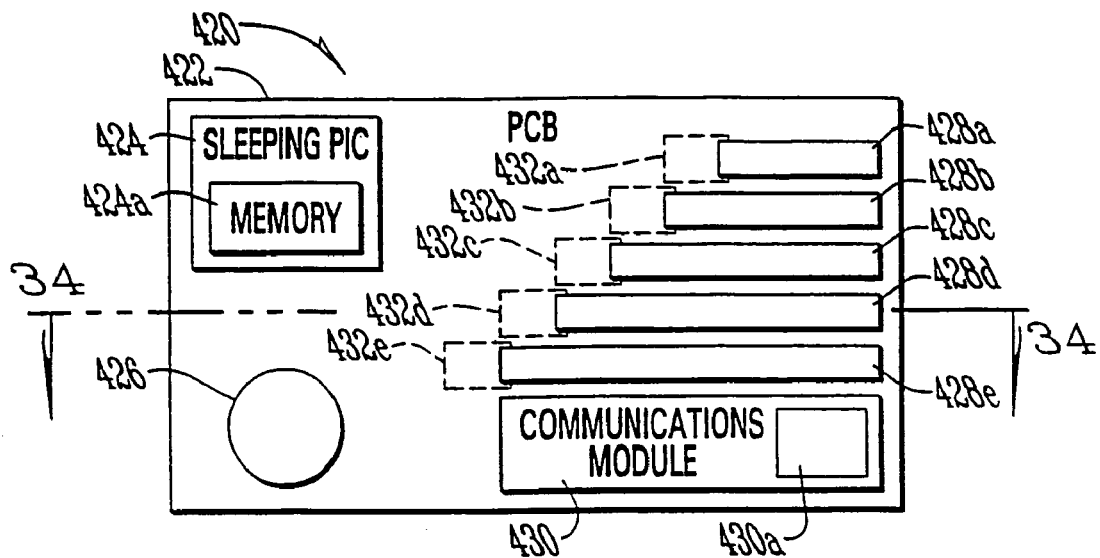
FIG. 33 shows, in a top view, a low-power, long life accelerometer sensor constructed according to the invention.

FIG. 33 shows a top view of a long-life accelerometer sensor 420 constructed according to the invention. Sensor 420 can for example be a MMD. Accelerometer sensor 420 includes a PCB 422, a processor 424 (preferably with internal memory 424a; memory 424a may be FLASH), a coin cell battery 426, a plurality of g-quantifying moment arms 428a-e, and communications module 430. PCB 422 has a matching plurality of contacts 432a-e, which sometimes connect in circuit with corresponding moment arms 428a-e. In one embodiment, module 430 is a transponder or RFID tag with internal FLASH memory 430a. The five moment arms 428a-e and contacts 432a-e are shown for illustrative purposes; fewer arm and contacts can be provided with accelerometer sensor, as few as one to four or more than five.

Battery 426 serves to power sensor 420. PCB 422 and processor 424 serve to collect data from accelerometer(s) 428a-e when one or more contact with contacts 432a-e. Communications module 430 serves to transmit data from sensor 422 to a receiver, such as in communications ports 16, 26. Operation of accelerometer sensor 420 is described with discussion of FIG. 34.

In illustrative example of operation of sensor 420, moment arm 428d moves in direction 434a when force moves arm 428d in the other direction 434b. Once arm 428d moves far enough (corresponding to space 436), then arm 428d contacts contact 432d. At that point, a circuit is completed between arm 428d, processor 424 and battery 426, such as through track lines 438a, 438b connecting, respectively, contact 432d and arm 428d to other components with PCB 422. A certain amount of force is required to move arm 428d to contact 432d; arm 428d is preferably constructed in such a way that that force is known. For example, arm 428d can be made to touch contact 432d in response to 10 g of force in direction 434a. Other arms 428a-c, 428e have different lengths (or at least different masses) so that they respond to different forces 434 to make contact with respective contacts 432. In this way, the array of moment arms 428 quantize several g's for accelerometer 100.

In the preferred embodiment, processor 424 includes A/D functionality and has a "sleep" mode, such as the "pic" 16F873 by MICROCHIP. Accordingly, accelerometer sensor 422 draws very little current during sleep mode and only wakes up to record contacts between arms 428 and contacts 432. The corresponding battery life of accelerometer sensor 422 is then very long since the only "active" component is processor 424—which is only active for very short period outside of sleep mode. Communications module is also active for just a period required to transmit data from sensor 420.

Figure 34:
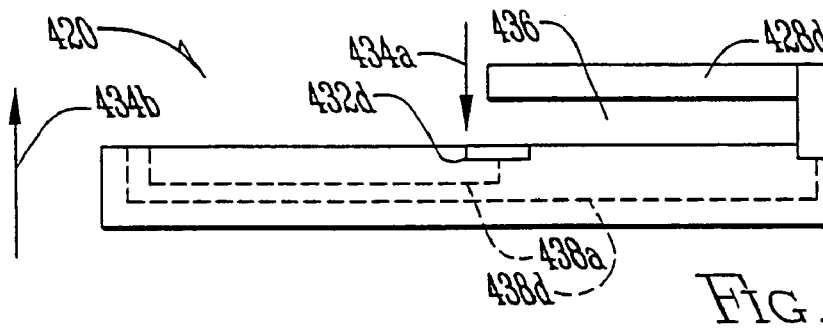
FIG. 34 shows a cross-sectional view of one portion of the accelerometer sensor of FIG. 33, illustrating operation of the moment arm quantifying g's in accord with the invention.

Processor 424 thus stores data events for the plurality of moment arms 428. By way of example, moment arms 428a-e can be made to complete the circuit with contacts 432 at 25 g (arm 428e), 20 g (arm 428d), 15 g (arm 428c), 10 g (arm 428b) and 5 g (arm 428a), and processor 424 stores results from the highest g measured by any one arm 428. For example, if the accelerometer sensor experiences a force 434b of 20 g, then each of arms 428e, 428d, 428c and 428b touch respective contacts 432; however only the largest result (20g for arm 428b) needs to be recorded since the other arms (428e-c)

cannot measure above their respective g ratings. Longer length arms 428 generally measure less force due to their increased responsiveness to force. Those skilled in the art should appreciate that arms 428 can be made with different masses, and even with the same length, to provide the same function as shown in FIGS. 33 and 34.

Data events from arms 428 may be recorded in memory 424*a* or 430*a*. If for example communications module 430 is a transponder or RFID tag, with internal FLASH memory 430*a*, then data is preferably stored in memory 430*a* when accelerometer sensor 420 wakes up; data is then off-loaded to a receiver interrogating transponder from memory 430*a*. Alternatively, processor 424 has memory 424*a* and event data is stored there. Module 430 might also be an RF transmitter that wirelessly transmits data off-board at predetermined intervals.

Figure 35:
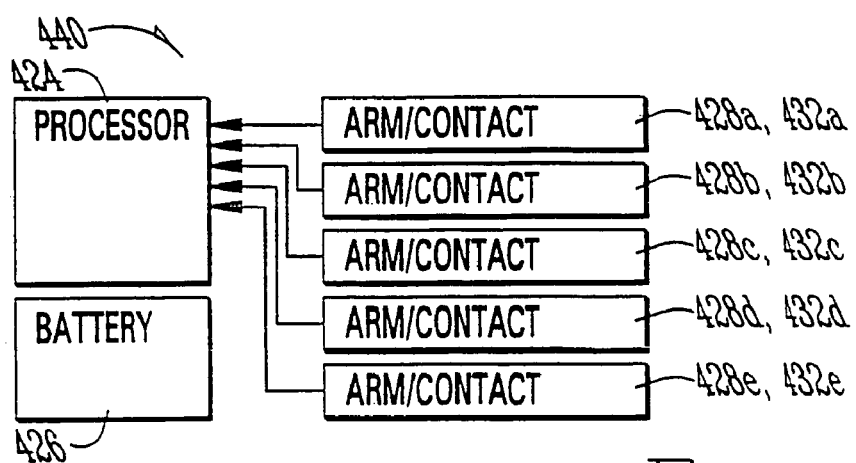
FIG. 35 shows a circuit illustrating operation of the accelerometer sensor of FIG. 33.

FIG. 35 shows a circuit 440 illustrating operation of accelerometer sensor 420. Processor 424 is minimally powered by battery 426 through PCB 422, and is generally in sleep mode until a signal is generated by one or more moment arms 428 with corresponding contacts 432. Each arm and contact combination 428, 432 serve to sense quantized g loads, as described above, and to initiate an "event" recording at processor 424, the event being generated when the g loads are met. Processor 424 then stores or causes data transmission of the time tagged g load events similar to the monitor device and receiver of FIG. 1.

Figure 36:
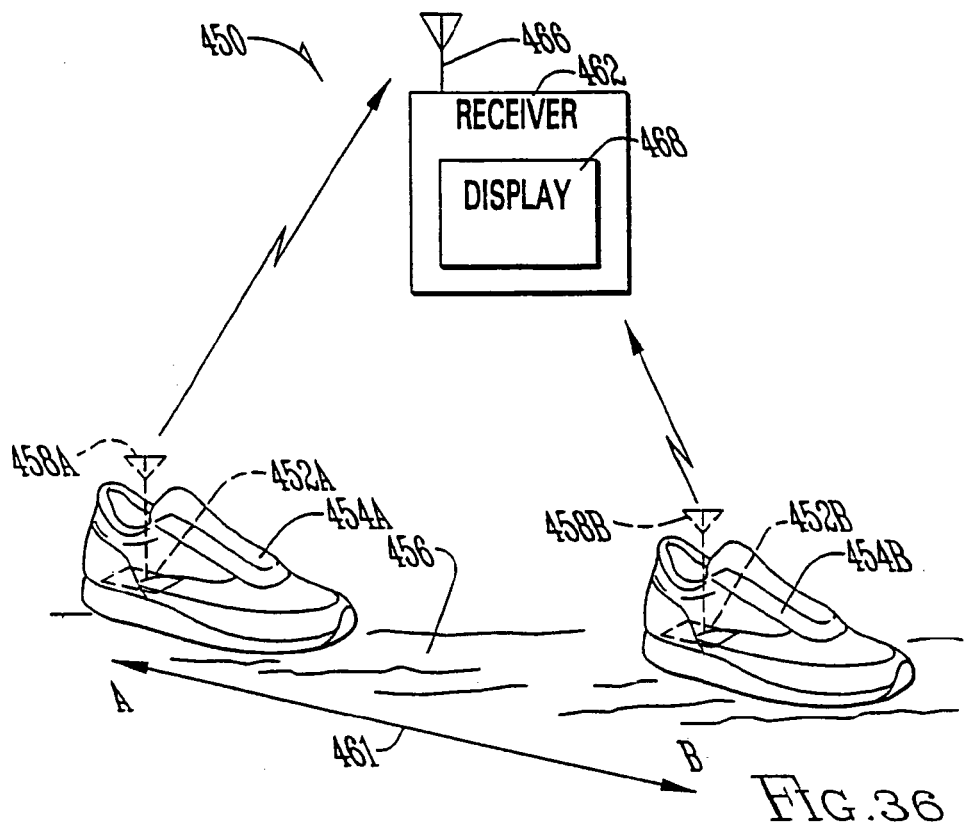
FIG. 36 illustrates a runner speedometer system constructed according to the invention.

FIG. 36 shows a runner speedometer system 450 constructed according to the invention. A sensor 452 is located with each running shoe 454. For purpose of illustration, shoes 454A, 454B are shown at static locations "A" and "B", corresponding to sequential landing locations of shoes 454. In reality, however, shoes 454 are not stationary while running, and typically they do not simultaneously land on ground 456 as they appear in FIG. 36. Sensor 452A is located with shoe 454A; sensor 452B is located with shoe 454B. Sensors 452 may be within each shoe 454 or attached thereto. Sensors 452A, 452B cooperatively function as a proximity sensor configured to determine stride distance 461 between sensors 452, while running. One or both of sensors 452 have an antenna 458 and internal transmitter (not shown). A sensor 452 can for example be a monitor device such as shown in FIG. 1, where detector 12 is the proximity sensor and the transmitter is the communications port 16. Receiver 462 is preferably in the form of a runner's watch with an antenna 466 and a communications port (e.g., port 26, FIG. 1) to receive signals from sensor(s) 452. Receiver 462 also preferably includes a processor and driver to drive a display 468. Receiver 462 can for example have elements 14, 18, 20, 22, 16 of device 10 of FIG. 1. Receiver 462 preferably provides real time clock information in addition to other functions such as displaying speed and distance data described herein.

In the preferred embodiment, sensors 452 internally process proximity data to calculate velocity and/or distance as "event" data, and then wirelessly communicate the event data to receiver 462. Alternatively, proximity data is relayed to receiver 462 without further calculation at sensors 452. Calculations to determine distance or velocity performed by a runner using shoes 454 can be accomplished in sensor(s) 452 or in receiver 462, or in combination between the two. Distance is determined by a maximum separation between sensors 452 for a stride; preferably, that maximum distance is scaled by a preselected value determined by empirical methods, since the maximum distance between sensors 452A, 452B determined while running is not generally equal to the actual separation 461 between successive foot landings (i.e., while running, only one of shoes 454 is on the ground at any one time typically, and so the maximum running separation is less than actual footprint separation 461—the scaling value accounts for this difference and calibrates system 450).

Velocity is then determined by the maximum stride distance (and preferably scaled to the preselected value) divided by the time associated with shoe 454 impacting ground 456. An accelerometer may be included with sensor 452 to assist in determining impacts corresponding to striking ground 456, and hence the time between adjacent impacts for shoe positions A and B. Events may be queued and transmitted in bursts to receiver 462; however events are typically communicated at each occurrence. Events are preferably time tagged, as described above, to provide additional timing detail at receiver 462.

Figure 37:
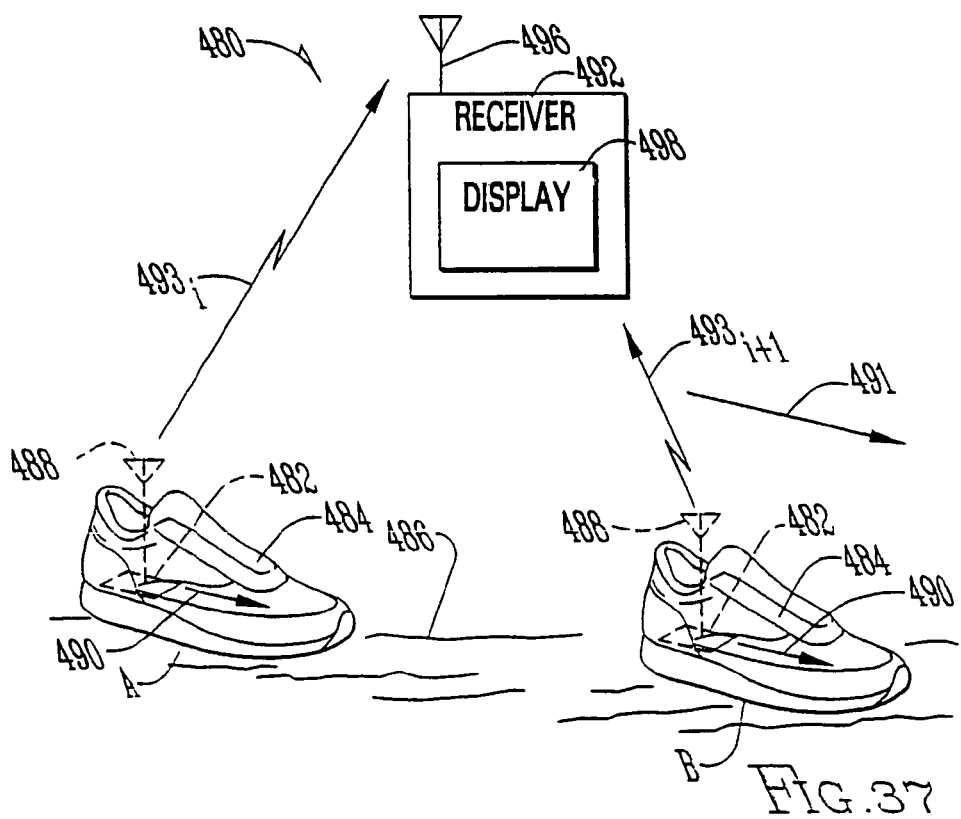
FIG. 37 illustrates an alternative runner speedometer system constructed according to the invention.

FIG. 37 shows an alternative runner speedometer system 480 constructed according to the invention. A sensor 482 is located with one running shoe 484. For purpose of illustration, shoe 484 is shown at two distinct but separate static locations "A" and "B", corresponding to successive landing locations of shoe 484. In reality, shoe 484 is not stationary while running, and also does not simultaneously land at two separate locations A, B on ground 486 as it appears in FIG. 37. Shoe 484 can correspond to the left or right foot of a runner using system 480. Sensor 482 is located with shoe 484; it may be within shoe 484 or attached thereto. Sensor 482 has an accelerometer oriented along axis 490, direction 490 being generally oriented towards the runner's direction of motion 491. Sensor 482 has an antenna 488 and internal transmitter (not shown). Sensor 482 can for example be a monitor device such as shown in FIG. 1, where detector 12 is the accelerometer oriented with sensitivity along direction 490, and the transmitter is the communications port 16. Sensor 482 transmits travel or acceleration data to receiver 492. Receiver 492 is preferably in the form of a runner's watch with an antenna 496 and a communications port (e.g., port 26, FIG. 1) to receive signals from sensor 482. Receiver 492 also preferably includes a processor and driver to drive a display 498. Receiver 492 can for example have elements 14, 18, 20, 22, 16 of device 10 of FIG. 1. Receiver 492 preferably provides real time clock information in addition to other functions such as displaying speed and distance data described herein.

In one embodiment, sensor 482 transmits continuous acceleration data to receiver 492; and receiver 492 calculates velocity and/or distance based upon the data, as described in more detail below. Sensor 492 thus operates much like a MMD 150 described in FIG. 8, and receiver 492 processes real time feeds of acceleration data to determine speed and/or distance. In the preferred embodiment, however, sensor 482 internally processes acceleration data from its accelerometer(s) to calculate velocity and/or distance as "event" data; it then wirelessly communicates the event data to receiver 492 as wireless data 493. Events are preferably queued and transmitted in bursts to receiver 492; however events are typically communicated at each occurrence (i.e., after each set of successive steps from A to B). Events are preferably time tagged, as described above, to provide additional timing detail at receiver 492.

Figure 38:
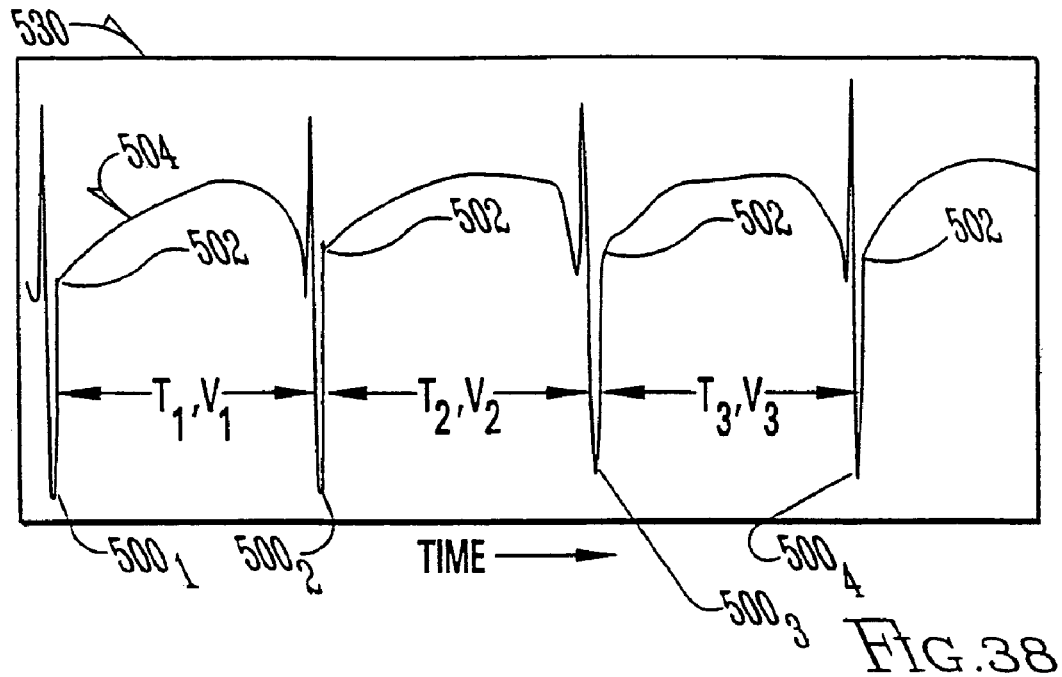
FIG. 38 illustrates data capture and analysis principles for determining speed with the system of FIG. 37.

Generally, sensor 482 calculates a velocity and/or distance event after sensing two "impacts." Impacts 500 are shown in FIG. 38. Each impact is detected by the sensor's accelerometer; when shoe 484 strikes ground 486 during running, a shock is transmitted through shoe 484 and sensor 482; and sensor 482 detects that impact 500. An additional accelerometer in sensor 482, oriented with sensitivity perpendicular to motion direction 491, may also be included to assist in detecting the impact; however even one accelerometer oriented along motion direction 490 receives jarring motion typically sufficient to determine impact 500.

Alternatively, sensor 482 calculates velocity and/or distance between successive low motion regions 502. Regions 502 correspond to when shoe is relatively stationary (at least along direction 491) after landing on ground 486 and prior to launching into the air.

Once impact 500 or low motion region 502 is determined within sensor 482, sensor 482 integrates acceleration data generated by its internal accelerometer until the next impact or low motion region to determine velocity; a double integration of the acceleration data may also be processed to determine distance. Preferably, data from the sensor accelerometer is processed through a low pass filter. Preferably, that filter is an analog filter with a pole of about 50 Hz (those skilled in the art should appreciate that other filters can be used). However, generally only velocity is calculated within sensor 482; and distance is calculated in receiver 492 based on the velocity information and time T between impacts 500 (or low motion regions 502) of sensor 482. Preferably, velocity is only calculated over the time interval $T_i$ between each impact 500. Velocity may alternatively be calculated over an interval that is shorter than T, such that runner velocity is scaled to velocity over the lesser interval. The shorter interval is useful in that acceleration data is sometimes more consistent over the shorter interval, and thus much more appropriate as a scalable gauge for velocity. Given the short time of T, very little drift of accelerometer data occurs, and velocity may be determined sufficiently. $T_i$ is typically less than about one second, and is typically about ½ second or less.

Briefly, the processor within sensor 482 samples accelerometer data within each "T" period, or portion of the T period, and integrates that data to determine velocity. The initial velocity starting from each impact 500 (or low motion region 502) is approximately zero. If $A_i$ represents one sample of accelerometer data, and the sampling rate of the processor is 200 Hz (i.e., preferably a rate higher than the low pass filter), then $A_i/200$ represents the velocity for one sample period (1/200 second) of the processor. Data 504 illustrates data $A_i$ over time t. Since T (in seconds)*200 samples=x samples are taken for each period T, then the sum of all of the $A_i/200$ for each of the x samples, divided by the number x, determines average velocity over period T. For integrations over a period that is less than T, fewer samples (less than x) are used to calculate velocity.

Sensor 482 calculates and transmits its velocity data to receiver 492. Velocity data $V_1$ corresponds to period $T_1$, velocity data $V_2$ corresponds to period $T_2$, and so on. Generally, because of processing time, sensor 482 in this example transmits $V_1$ in period $T_2$, transmits $V_2$ during period $T_3$, and so on. Receiver 492 averages $V_i$, over time, and communicates the average to the runner in useful units, e.g., 10 mph or 15 kmph.

Note that if only one accelerometer is provided with each shoe 484, then calibration of velocity Vi may be made for sensor 452 by calibration against a known reference, e.g., by running after a car or running on a treadmill. More particularly, since the accelerometer is oriented in various ways during a period T, other than along direction 491, then errors are induced due to the acceleration of gravity and other forces. However, since $V_i$ is reported sequentially to receiver 492, a correction factor may be applied to these velocities prior to display on display 498. By way of example, if one runner substantially maintains his shoes 484 level, such that accelerometers in sensors 492 maintain a constant orientation along direction 491 during period T, then the reported $V_i$ reasonably approximates actual velocity over that period.

However if the runner points his shoes with toe towards ground 486, during period T, then only a component of the detected acceleration vector is oriented along direction 491. However, by calibrating system 480 against a known reference, a substantially true velocity for each period T may be obtained. Moreover, shoe sensor 482 can have a different adjustment factor applied for different gaits (e.g., jogging or running, as shoe orientations during period T may vary for different gaits).

Generally, a calibration for velocity is made at least once for each shoe using the invention, to account for variations in electronic components and other effects. Calibration also adjusts for the gait of the runner in orienting the accelerometer relative to ground 486. Preferably, like several of the MMDs described herein, a battery powers sensor 482; and that battery can be replaced once depleted. Implanting the MMD within shoe 484 is beneficial in that a fixed orientation, relative to direction 491, is made at each landing.

Figure 39:
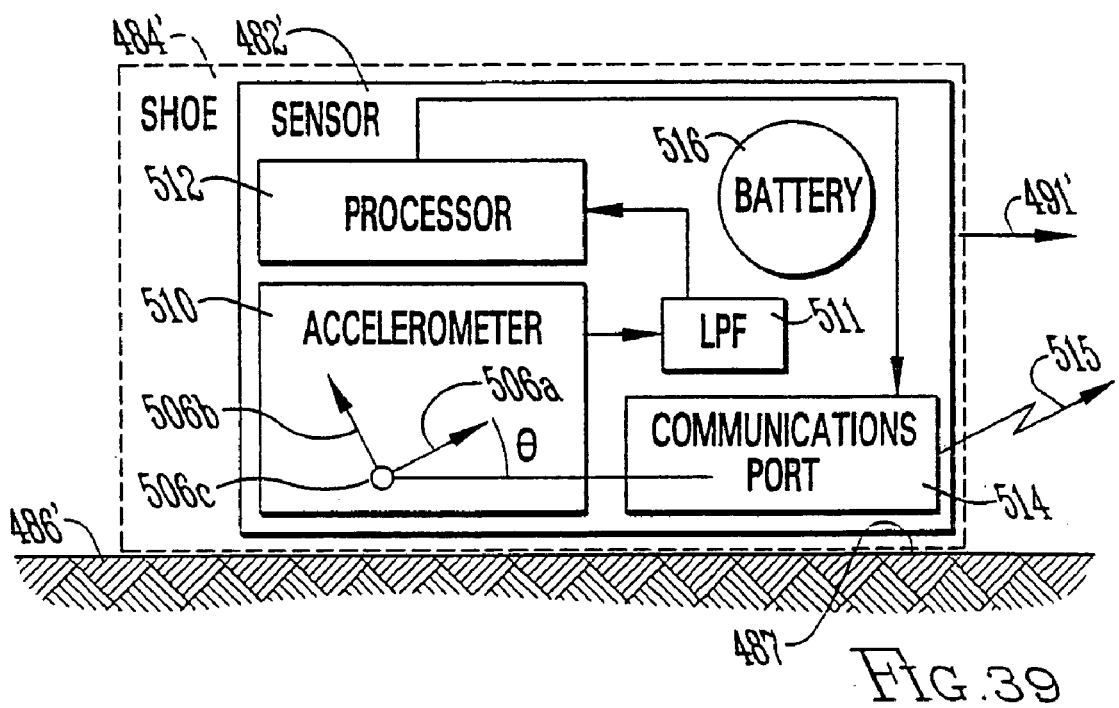
FIG. 39 illustrates one sensor for operation with a shoe in a speedometer system such as described in FIG. 37.

To alleviate the problems associated with acceleration errors, one preferred sensor 482' for a shoe 484' is shown in FIG. 39. Sensor 482' is shown in a side cross sectional view (not to scale); and motion direction 491' of the runner is shown in relation to accelerometer orientation axes 506a, 506b and ground 486'. Shoe 484' is shown flat on (ground 486' and generally having a sole orientation 487 also at angle θ relative to accelerometer axis 506a. Sensor 482' has at least a two-axis accelerometer 510 (or, alternatively, a three axis accelerometer, with the third axis oriented in direction 506c) as the sensor detector, with one axis 506a oriented at angle θ relative to ground 486' (and hence relative to shoe sole 487 on ground 486'). Angle θ is chosen, preferably, such that accelerometer axis 506a maximally orients along axis 491' while the runner runs. Specifically, since during a period T the toe of shoe 484' tips towards ground 486' while running, then angle θ approximately orients that accelerometer such that its sensitive axis 506a is parallel with axis 491' for at least part of period $T_i$. Angle θ can be approximately forty-five degrees. Other angles are also suitable; for example an angle θ of zero degrees is described in connection with FIG. 37, and other angles up to about seventy-five degrees may also function sufficiently. Axis 506b is preferably oriented with sensitivity perpendicular to orientation 506a. Data from accelerometer 510 is communicated to low pass filter 511 and then to processor 512 where it is sampled as data $A_{i,\ a,\ b,\ c}$ (a, b, c representing the two or three separate axes 506a-c of sensitivity for accelerometer 510). Data $A_{i,\ a,\ b,\ c}$ is then used to (a) determine impacts 500 (and/or low motion regions 502), as above, and (b) determine $V_i$ based upon $A_{i,\ a,\ b,\ c}$ for any given period $T_i$ (or for any part of a period T). Errors in $V_i$ are corrected by processing the several components $A_{i,\ a,\ b,\ c}$ of the acceleration data. If for example data $A_{i,\ a}$ is "zero" for part of period T, then either the shoe is at constant velocity, or stopped; or if $A_{i,\ a}$ is "one" then it is substantially oriented with the toe greatly tipped towards ground 486', such that that accelerometer reads the acceleration due to gravity only. Data $A_{i,\ b}$ may be used to determine which physical case it is, and to augment the whole $A_i$ data stream in determining $V_i$.

Once processor 512 determines $V_i$ for period $T_i$, then communications port 514 transmits $V_i$ to the user's watch receiver (e.g., receiver 492, FIG. 37) as wireless data 515. The watch receiver calculates a useful runner speed, e.g., 15 km/hour, and displays that to the user. Battery 516 powers sensor 482'.

Note that the systems of FIG. 36, 37, 39 provide other benefits associated with upward or downward movement and work functions. Such upward or downward movement, when determined, defines a change of potential energy that may be reported as work or caloric burn. For example, accelerometer 510 can include multiple axes, such that angle θ may be determined. By knowing vertical climb, even over short distances, a work function is created. An inclinometer or angle measurement may also be integrated into such systems, and work functions may also be determined on a hill. Certain MMDs of the invention include for example speed detectors (e.g., accelerometers or Doppler radar devices) to determine speed. By using the hill angle for the upward or downward movement, with speed, another work function is created associated with the climb or descent. Such a work function can add to caloric consumption calculations in fitness or biking applications. Such inventions are also useful in determining whether the climb occurred on a hill or on stairs, also assisting the work function calculation.

There are several advantages of the invention of FIGS. 36-39. The prior art such as shown in U.S. Pat. No. 6,052,654, incorporated by reference, describes a calculating pedometer; but the system does not automatically calculate speed and distance as the invention does. Another patent, U.S. Pat. No. 5,955,667, also incorporated herein by reference, requires the use of a tilt sensor or other mechanism that determines the angular orientation of accelerometers relative to a datum plane. The invention does not require tilt sensors or the continual determination of the angle of the accelerometers relative to a fresh datum plane.

Figure 40:
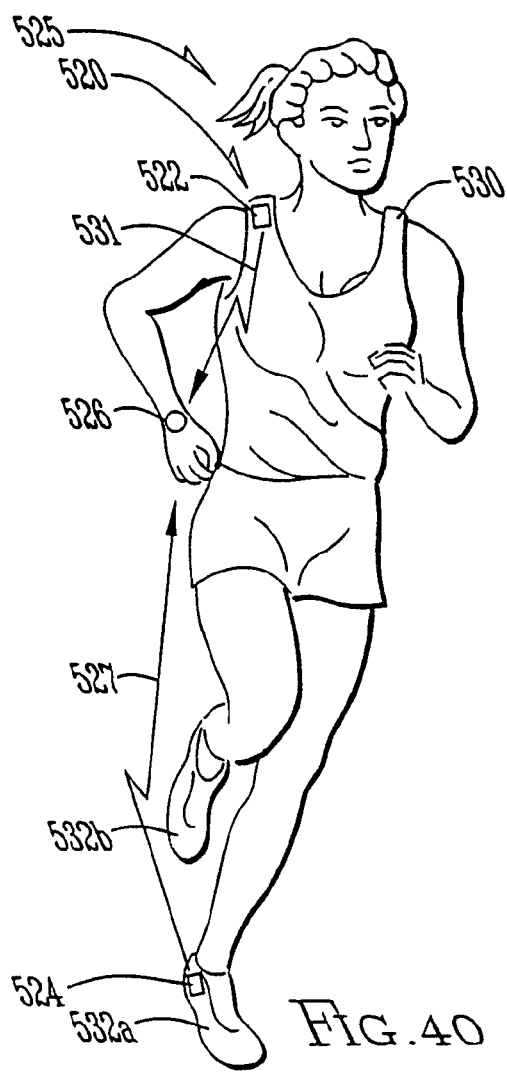
FIG. 40 shows another runner speedometer system of the invention, including a GPS sensor.

FIG. 40 shows one runner speedometer system 520 constructed according to the invention. System 520 includes a GPS monitor device 522, accelerometer-based monitor device 524, and wrist instrument 526. Device 522 is similar to device 10 of FIG. 1 except detector 12 is a GPS chipset receiving and decoding GPS signals. Device 522 has a processor (e.g., processor 12, FIG. 1) that communicates with the chipset detector to determine speed and/or distance. Speed and/or distance can be accurately determined without knowing absolute location, as in the GPS sensors of the prior art. Speed and/or distance information is then wirelessly communicated, via its communications port, to wrist instrument 526 as wireless data 531. Instrument 526 is preferably a digital watch with functionality such as receiver 24, FIG. 1. Preferably, device 522 clips into clothing pocket of the runner's shirt 530. As described above, system 520 includes one or two accelerometer-based devices 524 in runner shoes 532. Device(s) 524 in shoe(s) 532 augment GPS device 522 to improve speed and/or distance accuracy of system 520; however either device 522, 524 may be used without the other. Together, however, system 520 preferably provides approximately 99% or better accuracy (for speed and/or distance) under non-obscured sky conditions. Wrist instrument 526 collates data from GPS device 522 and accelerometer device(s) 524 to provide overall speed and distance traveled information, as well as desired timing and fitness data metrics.

System 520 thus preferably has at least one MMD 524 attached to, or within, runner shoe 532; MMD 524 of the preferred embodiment includes at least one accelerometer arranged to detect forward acceleration of runner 525. A processor within MMD 524 processes the forward acceleration to determine runner speed. Additional accelerometers in MMD 524 may be used, as described herein, to assist in determining speed with improved accuracy. In the preferred embodiment, MMD 524 wirelessly transmits speed as wireless data 527 to wrist instrument 526, where speed is displayed for runner 525. System 520 providing speed from a single MMD 524 can provide speed accuracy of about 97%. To improve accuracy, a second MMD 524 (not shown) is attached to, or placed within, a second shoe 532; the second MMD 524 also determining runner speed. Speed information from a second shoe 532b is thus combined with speed information from shoe 532a to provide improved speed accuracy to runner 525; for example, the two speeds from shoes 532a, 532b are averaged. System 520 providing speed from a pair of MMDs 524 can provide speed accuracy of better than 97%.

System 520 works as a runner speedometer with MMD 524 (or multiple MMDs 524, one in each shoe 532). However, to improve accuracy of speed delivered to runner 525, a GPS chip device 522 is attached to clothing 530 of runner 525. Device 522 may for example be placed within a pocket of clothing 530, the pocket being in the shoulder region so that device 522 has a good view of the sky. Device 522 processes successive GPS signals to determine a speed based upon successive positions. System 520 utilizing device 522 thus provides enhanced speed to runner 525 when using device 522. Speed from device 522 is communicated to wrist instrument 526 where it is displayed for runner 525. Preferably, instrument 526 uses speed from device 522 when speed data is consistent and approximately similar to speed data from MMD 524. Instrument 526 alternatively combines speed data from device 522 and device 524 to provide a composite speed. If device 522 is obscured, so GPS signals are not available, then system 520 provides speed to runner 525 solely from MMD 524 (or multiple MMDs 524, one in each shoe). As an alternative, device 522 can be integrated within a pocket in a hat worn by runner 525, such that device 522 again has an un-obscured view of the sky.

Figure 41:
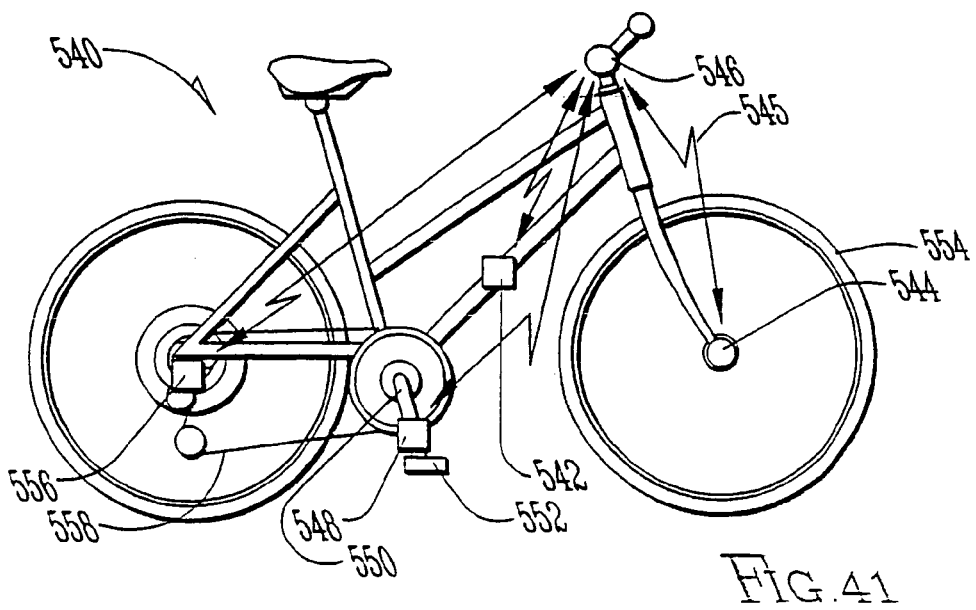
FIG. 41 shows a biking work function system constructed according to the invention.

FIG. 41 shows a computerized bicycle system 540 constructed according to the invention. In use, system 540 determines caloric burn or "work" energy expended, among other functions described herein. System 540 includes fore/aft tilt sensor 542 and speed sensor 544; sensors 542, 544 determine then wirelessly transmit bicycle tilt information and speed information, respectively, and as wireless data 545, to receiver and display 546. A processor (not shown) in receiver and display 546 combines data from sensors 542, 544 to determine elevation change, and, hence, work energy (e.g., change of potential energy); receiver and display 546 then displays work energy to a user of bicycle system 540. Work energy may be converted to caloric burn, in one embodiment of the invention. Sensor 542 may include a small gyroscope or an electrolytic type tilt device, known in the art, as the detector for measuring bicycle tilt. Speed sensor 544 is readily known in the art; however the combination of speed sensor 544 with other sensors of FIG. 41 provides new and useful data accord with the invention.

System 540 can additionally include crank torque measurement sensor 548. Sensor 548 preferably includes a strain gauge connected with bicycle crank 550 to measure force applied to pedals 552 and wheels 554. Preferably, a sensor 548 is applied to each pedal so that system 540 determines the full effort applied by the cyclist on any terrain. Sensor(s) 548 accumulate, process and transmit tension data to receiver and display 546. System 540 can additionally include tension measurement sensor 556 used to measure tension of chain 558. Sensor 556 similarly accumulates, processes and transmits tension data to receiver and display 546. Device 546 preferably includes processing and memory elements (e.g., similar to receiver 231, FIG. 10G) to accumulate and process data from one or more of sensors 542, 544, 548, 556 in the desired way for a user of system 540.

As alternatives to system 540, without departing from the scope of the invention, those skilled in the art should appreciate that (1) sensor 542 may be combined with either of sensor 544 or receiver 546; (2) sensors 542 and 544 may communicate through electrical wiring instead of through wireless communications; (3) a GPS sensor providing earth location and altitude may instead provide the data of sensors 542, 544 for system 540; and (4) receiver and display 546 may instead be a watch mounted to a user's wrist. Preferably, system 540 includes memory, e.g., within receiver and display 546, that stores gradient information associated with a certain ride on terrain, and then provides a "trail difficulty" assessment for the stored data. Maximum and minimum gradients are also preferably stored and annotated in memory for later review by a user of system 540.

FIG. 42 shows a system 600 constructed according to the invention. System 600 is particularly useful for application to spectator sports like NASCAR. System 600 in one application thus includes an array of data capture devices 602 coupled to racecars 604. A data capture device 602 may for example be a monitor device as described herein, with one or a plurality of detectors to monitor movement metrics. As described below, data capture devices 602 preferably have wireless transmitters connected with antennas to transmit wireless data 606 to listening receivers 608. Receivers 608 can take the form of a computer relay 608*a* and/or a crowd data device 608*b*, each of which is described below. In the preferred embodiment, data capture devices 602 communicate wireless data 606 to computer relay 608*a*; and computer relay 608*a* relays select wireless data 610 to a plurality of crowd data devices 608*b*. However, data capture devices 602 can directly relay wireless data 606 to crowd data devices 608*b*, if desired, and as a matter of design choice. Crowd data devices 608*b* are provided to spectators 612 during a sporting event, such as a NASCAR race of racecars 604 on racetrack 605. Devices 608*b* may be rented, sold or otherwise provided to spectators 612, such as in connection with ticketing to access racetrack 605, and to sit in spectator stands 616. Data devices 608*b* may also be modified personal data devices or cell phones enabled to interpret wireless data 606 and/or 610 for display of relevant information to its owner-spectator. Access to data 606, 610 in this manner is preferably accomplished contractually such that the cell phones or data devices have encoded information necessary to decode wireless data 606 and/or 610.

Wireless data 606 can for example be at 2.4 GHz since data capture device 602 may be sufficiently powered from racecars 604. Wireless data 610 can for example be unlicensed frequencies such as 433 MHz or 900-928 MHz, so that each crowd data device 608*b* may be powered by small batteries such as described herein in connection with receivers for monitor devices. Wireless data 610 can further derive from cellular networks, if desired, to communicate directly with a crowd data device. Wireless link 606 and 610 can encompass two way communications, if desired, such as through wireless transceivers.

Computer relay 608*a* may further provide data directly to a display scoreboard 614 so that spectators 612 may view scoreboard 614 for information derived by system 600. Scoreboard 614 may for example be near to spectator stand 616.

FIG. 43 shows one data capture device 602' constructed according to the invention. Device 602' may be attached to car 604' or integrated with car 604'. For purposes of illustration, car 604' is only partially shown, with wheels 605 and body 607. Preferably, device 602' is integrated with existing car electronics 618. For example, car electronics 618 typically include a speedometer and tachometer, and other gauges for fuel and overheating. Device 602' thus preferably integrates and communicates with car electronics 618, as illustrated by overlapping dotted lines between items 602' and 618. Device 602' also communicates desired metric information to spectators 612 (either directly or through computer relay 608*a*). Device 602' thus includes a wireless transmitter 620 and antenna 622 to generate wireless data 606'.

Data relayed to spectators 612 can be of varied format. Device 602' can for example be a MMD with a detector providing acceleration information. Acceleration data in the form of "g's" and impact is one preferred data communicated to spectators 612 through wireless data 606'. Car 604' may in addition have accelerometers as part of car electronics; and device 602' preferably communicates on-board acceleration data as wireless data 606'. Device 602' and car electronics 618 can for example include a speedometer, accelerometer, tachometer, gas gauge, spin sensor, temperature gauge, and driver heart rate sensor. An on-board computer can further provide position information about car 604' position within the current race (e.g., 4$^{th}$ out of fifteen racecars). Accordingly, device 602' collects data from these sensors and electronic sources and communicates one or more of the following information as wireless data 606': racecar speed, engine revolutions per minute, engine temperature, driver heart rate, gas level, impact, g's, race track position, and spin information. As described in connection with the monitor devices above, data 606' may be continually transmitted or transmitted at timed sequence intervals, e.g., every minute. Data 606' may also be transmitted when an event occurs, e.g., when a major impact is reported by a device 602' (e.g., in the form of a MMD) such as when car 604' experiences a crash. A spin sensor also preferably quantifies rollover rate, acceleration and total rotations (e.g., four flips of the car is 1440 degrees).

FIG. 44 shows one crowd data device 608*b*' constructed according to the invention. Device 608*b*' in one embodiment is a cell phone constructed and adapted to interpret information from wireless data 606' (or data 610). Device 608*b*' can also be a receiver such as receiver 24 of FIG. 1. Device 608*b*' preferably includes a display 621 to display metrics acquired from information within wireless data 606' (and/or data 610). Communications port 623 and antenna 624 capture data 606' and/or 610. An internal processor decodes and drives display 621. On-Off button 628 turns device 608*b*' on and off. Car selector button 630 provides for selecting which car 604' to review data from. Data mode button 632 provides for selecting which data to view from selected car 604'.

Data captured by device 608*b*' may be from one car or from multiple cars 604. Car selection button 630 can be pressed to capture all data 606' from all cars, or only certain data from one car, or variants thereof. In one embodiment, the update rate transferred as wireless data 606' from any car 604' to any crowd data device is about one second; and so each device generally acquires data from one car at any one time and "immediately" (i.e., within about one second) acquires data from another car if selected by button 630. Alternatively, all data 606' from all cars 604 are communicated and captured to each device 608*b*'. This alternative mode however uses more data bandwidth to devices 608*b*'.

Accordingly, users of crowd data device 608*b*' may view performance and data metrics from any car of choice during a race. Currently, spectators only have a vague feel for what is actually happening to a car at a race between multiple cars 604. With the invention, a spectator can monitor her car of choice and review data personally desired. One spectator might for example be interested in the driver heart rate of one car; one other spectator might for example be interested in the speed of the lead car; yet another spectator might for example be interested in the temperature of the top four cars; most spectators are concerned about which car is the lead car. In accord with the invention, each spectator may acquire personal desired data in near real time and display it on individual crowd data devices in accord with the invention. Data captured from system 600 can further be relayed to the Internet or to broadcast media through computer relay 608a, if desired, so that performance metrics may be obtained at remote locations and, again, in near real time.

The invention also provides for displaying certain data at display scoreboard 614. Computer relay 608a may in addition connect to race officials with computers that quantify or collate car order and other details like car speed. Such data can be relayed to individuals through crowd data devices 608b or through scoreboard 614, or both.

Figure 45:
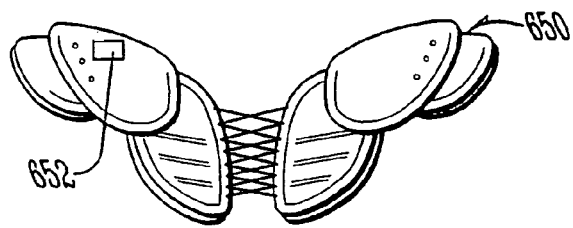
FIG. 45 shows one body-armor incorporating a monitor device in accord with the invention.

System 600 may be applied to many competitive sports. For example, when the data capture device is like a MMD, system 600 can be applied to sports like hockey, basketball, football, soccer, volleyball and rodeos. A MMD in the form of an adhesive bandage, described above, is particularly useful. Such a MMD can for example be applied with football body armor or padding, as illustrated in FIG. 45. FIG. 45 shows a football player's padding 650 with a MMD 652. MMD 652 can be applied external to padding 650, though it is preferably constructed internally to padding 650. MMD 652 operates like a data capture device 602 of system 600 (FIG. 42). MMD 652 can for example capture and relay impact information to spectators of a football game, where each of the players wears body armor or padding such as padding 650, to provide performance metrics for all players and to individual spectators. Impacts from blows between players may then be obtained for any player for relay to any spectator or user of the Internet according to the teachings of the invention. Device 652 can alternatively include other detectors, e.g., heart-rate detectors, to monitor fitness and tiredness levels of athletes in real time; preferably, in this aspect, MMD 652 attaches directly to the skin of the player.

Figure 46:
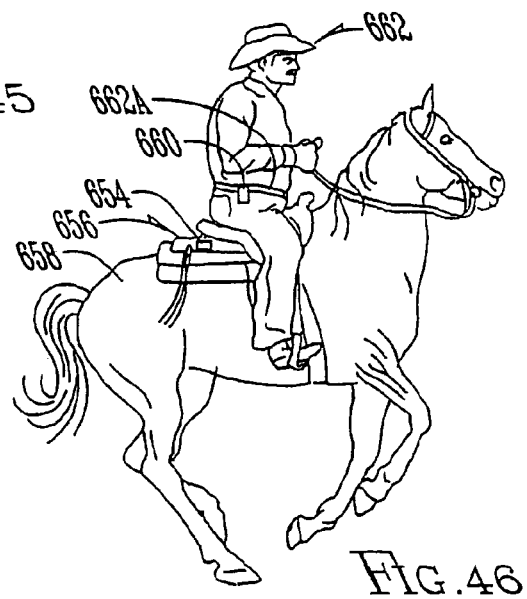
FIG. 46 shows one system for measuring rodeo and/or bull riders in accord with other embodiments of the invention.

Likewise, a MMD of the invention is effectively used in rodeo, as shown in FIG. 46. Preferably one MMD 654 attaches to the saddle 656 of the animal 658 ridden in the rodeo (or to the horn of a bull, or to a rope attached to the animal), and one MMD 660 attaches to the rider 662 on animal 658. Each MMD generates a signal, similar to signals 154, 156 of FIG. 8A. As such, data from each MMD 654, 660 can be compared to the other to assess how well rider 662 rides in saddle 656. This comparison may be beneficially used in judging, removing subjectivity from the sport. For example, by attaching MMD 660 with the pant-belt 662A of rider 662, if signals from MMDs 654, 660 collate appropriately, then rider 662 is efficiently riding animal 658. Of course, one MMD 654 or 660 can also be used beneficially to report metrics such as impact to the audience.

Figure 47:
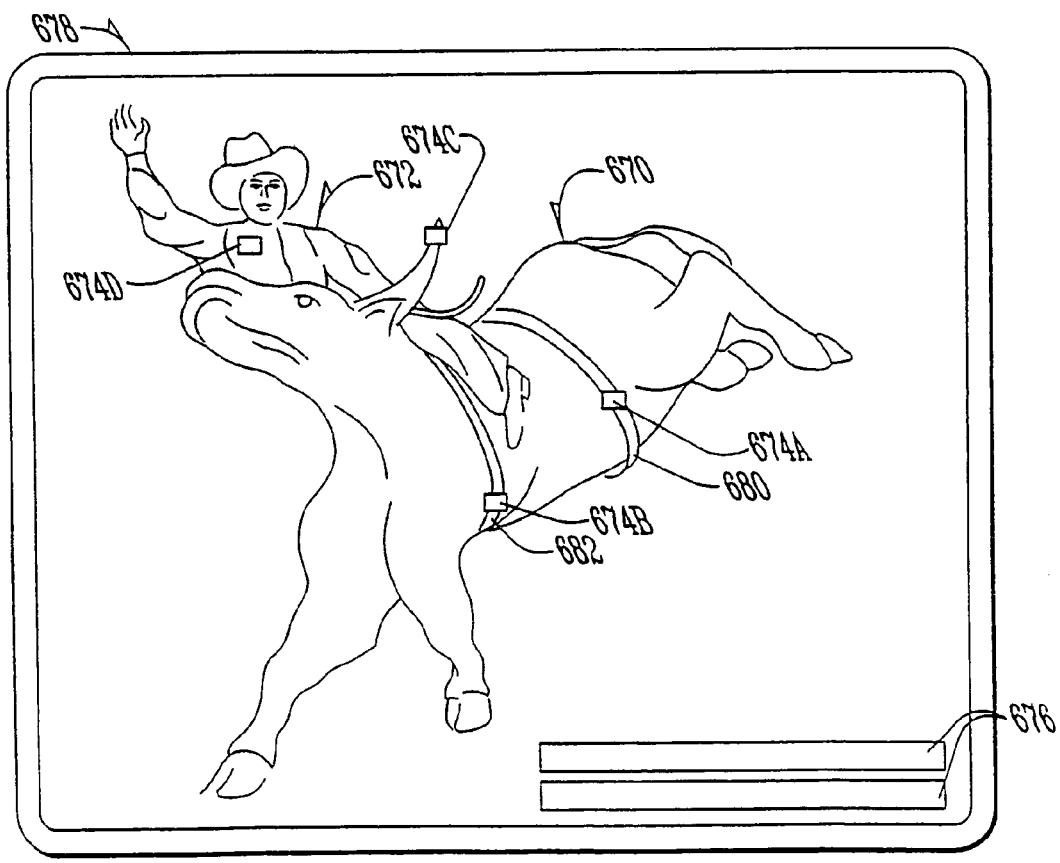
FIG. 47 shows a representative television display of a bull and rider configured with a system monitoring characteristics of the bull and/or rider, in accord with the invention.

FIG. 47 shows a representative television or video monitor display 678 of a bull 670 and bull rider 672, as well as a plurality of MMDs 674A-D attached thereto to monitor certain aspects of bull and rider activity, in accord with the invention. Display 678 also includes a graphic 676 providing data from one or more of MMDs 674 so that a view of display 678 can review movement metric content associated bull and/or rider activity. In exemplary operation, MMD 674A is attached to back rope 680 so as to monitor, for example, rump bounce impacts and frequency; MMD 674B is attached to rider rope 682 so as to monitor, for example, loosening of the grip of rider 672 onto bull 670; MMD 674C is attached to bull horn 684 so as to monitor, for example, bull head bounce and frequency; and MMD 674D is attached to rider 672 so as to monitor, for example, rider bounce and frequency, and impact upon being thrown from bull 670. A sensor (not shown) may also attach to the rider's foot or boot, if desired. MMDs 674 can for example be coupled to a reconstruction computer and receiver 152 of FIG. 8A, so as to process multiple MMDs 674 and to report meaningful data to a television, scoreboard and/or the Internet. Data collected from MMDs 674 in one embodiment are collated and stored in a database so as to characterize bull strength and throwing efficiency over time. For example, by looking at magnitude and frequency of acceleration data from MMD 674C over time for a particular bull provides detail as to how the bull behaves over time. Professional bull riding media can then better gauge which bulls to use for which riders and events.

Those skilled in the art should also appreciate that MMDs 674 can include different detectors providing data desired by sports media. For example, if the MMD contains a linear accelerometer, linear motion forces are reported; if the MMD contains a rotational accelerometer, rotational forces are reported. These MMDs may be placed on various parts of bull 670 or rider 672, such as on the body and head. Data from MMDs may be relayed to television, scoreboards and/or the Internet. Data collated on the Internet preferably includes bull and rider performance summaries.

Figure 48:
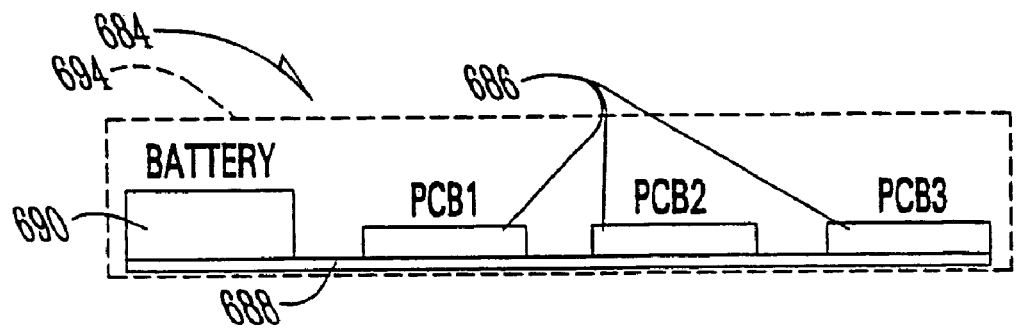
FIG. 48 shows one EMD of the invention utilizing flex strip as the "PCB" in accord with the invention.

FIG. 48 shows one EMD or MMD 684 constructed according to the invention. EMD or MMD 684 has specific advantages as a "wearable" sensor, similar to MMD 10", FIG. 2. EMD or MMD 684 utilizes "flex strip" 688 (known in the art) to mount mini-PCBs 686 (devices 686 can also be silicon chips) directly thereto. As a whole, EMD or MMD 684 can "wrap" about objects and persons to fulfill the variety of needs disclosed herein. By way of example, EMD or MMD 684 is useful for comfortable attachment to the rodeo rider 662, FIG. 46, such as to monitor and report "impact" events. Another such EMD or MMD 684 may be attached to a bull or rider to monitor and report heartbeat. In one embodiment, a Kapton flex circuit 688 connects battery 690 to the PCBs 686, and PCBs 686 to one other, so as to flexibly conform to the shape of the underlying object or body. In one option, EMD or MMD 684 is all housed high-density foam or similar flexible housing 694; this can maximize the EMD or MMD's protection and allow it to be worn close to the object of body. For example, such an EMD or MMD 684 may be worn on the torso of a person, where accurate g-levels seen by the body can be measured. In one embodiment, battery 690 is a plastic Lithium-ion power cell that has a malleable plastic case with any variety of form factor. Other batteries may also be used, in accord with the invention.

The invention of one preferred embodiment employs data taken from monitor devices such as described above and applies that data to video games, arcade games, computer games and the like (collectively a "game") to "personalize" the game to real ability and persons. For example, when a monitor device is used to capture airtime (and e.g., heart rate) of a snowboarder, that data is downloaded to a database for a game and used to "limit" how a game competitor plays the game. In this way, a snowboard game player can compete against world-class athletes, and others, with some level of realism provided by the real data used in the game.

More particularly, one missing link in the prior art between video games and reality is that one a person can be great at a video game and relatively poor at a corresponding real sport (e.g., if the game is a snowboard game, the player may not be a good snowboarder; if the game is a car race, the person may not be a good race car driver; and so on). With performance metrics captured as described herein, the data is applied such that an entirely new option is provided with games. As known in the art, games take the form of PLAYSTATION, SEGA, GAMEBOY, etc.

In operation the invention of the preferred embodiment works as follows. Individuals use a monitor device to measure one or more performance metrics in real life. Data from the monitor devices are then downloaded into a game (or computer running the game) for direct use by the game. Data used in the game may be averaged or it may be the best score for a particular player. By way of example, when the performance metric is "airtime", the option applied to the game allows the game player (typically a teenager) to measure a certain number of airtimes, in real life, and download them into the game so that the air the game player 'catches' during the game corresponds to his real airtime (e.g., best airtime, average airtime, etc.). Data used in games can be collated and interpreted in many ways, such as an individual's best seven airtimes of a day or a personal all time record for an airtime jump.

The effect of the invention applied to games is that game users are somewhat restricted in what they can do. In a ski game, for example, a kid that does not have the natural athletic ability to do flips will not, if the option is selected, be permitted to perform flips in a game. Competitions within games then become far more real. If a kid catches only one second of airtime, on average, then it is unlikely that he can catch three seconds of airtime like Olympic athletes; accordingly, when the gaming option is selected, those kids will not be permitted within the game to throw airtime (and corresponding tricks that require like airtimes) of three seconds or higher, for example. The game restricts them to doing tricks that could actually be completed in their normal airtime.

There would of course still be elements making the game unrealistic, and fun. The invention applied to games does however add a measure of realism to the games. For example, limiting a game to airtime may restrict movements to certain types, e.g., one flip instead of two. This is one example of how the invention applied to games makes the game much more real. Another gaming option is to permit the gaming user to expand their current real performance by some percentage. For example, a gaming user can instruct the game to permit 100% performance boost to his real data in competitions in the game. In this way, the gaming user knows how far off his real performance is from gaming performance. If for example it takes a 120% performance boost to beat a well-known Olympic athlete, then she knows (at least in some quasi-quantitative measure) how much harder she will need to work (i.e., 20%) to compete with the Olympic athlete.

Similar limitations to the games may be done with other metrics discussed herein, including drop distance, speed and impact, heart rate and other metrics. For example, by acquiring "impact" data through a MMD of the invention, it is known how much impact a particular athlete achieves during a jump or during a particular activity. By way of example, by collecting impact data from a boxer or karate athlete, it is roughly known the magnitude of impacts that that person endures. Such limitations are applied to games, in accord with other embodiments of the invention. Accordingly, a video game competitor may be limited to actions that he or she can actually withstand in real life. Spin rates too can limit the game in similar ways.

In the preferred embodiment of the invention, data from monitor devices applied to persons are downloaded as performance metrics into games. These metrics become parameters that are adhered to by the player if the gaming option is selected within the game. The ability to play the game, and the moving of the correct buttons, joystick or whatever, is thus linked to the real sport. By way of example, PLAYSTATION has a 'world championship' for the games. In accord with the invention, game players may now compete with their ability tied to competitions within the game, making it much more realistic on the slopes, vert ramp or other game obstacle.

In accord with one embodiment, systems like system 600 are also effectively applied to "venues" like skateparks. The data capture devices (preferably in the form of MMDs) are applied to individual users of the venue, e.g., skateboarders. Data acquired from the users are transmitted to a computer relay that in turn connects directly to game providers or Internet gaming sources. The venues are thus linked to games. Resorts with venues such as terrain parks are thus incentivized to make their venue part of the gaming world, where kids play in their park in synthesized video, and then actually use the venue to acquire data for use with the game. By tying competitors together from real venues to gaming, a real venue and a game venue become much more alike. Stigmas associated with playing games may also be reduced because gaming is then tied to reality and kids can participate in meaningful ways, both at the venue and within the game. Kids can then compete based upon real ability at both the game and in real life.

Figure 49:
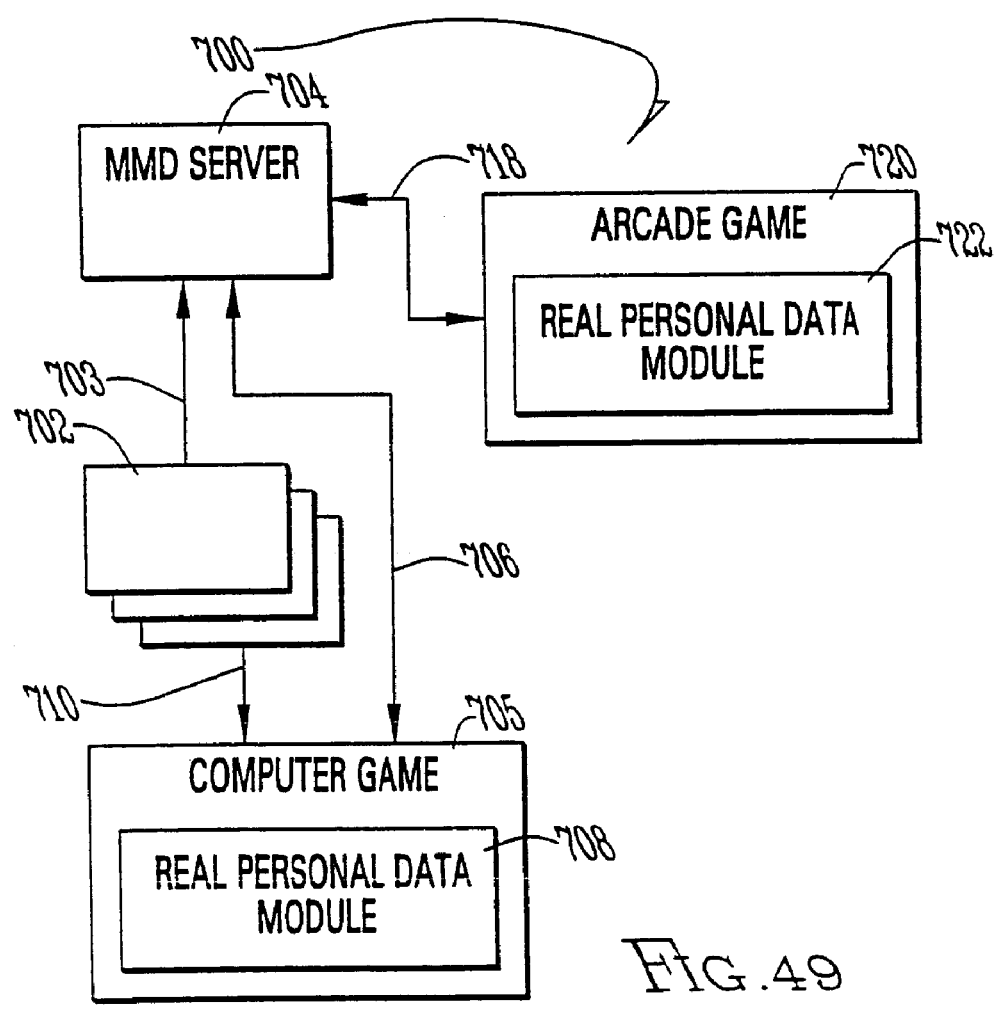
FIG. 49 depicts one computerized gaming system of the invention.

FIG. 49 shows one network gaming system 700 constructed according to the invention. System 700 operates to collect data from one or more monitor devices 702, such as through an Internet connection 703 with multiple home users of devices 702. A server 704 collates performance data and relays parameters to games. By way of example, server 704 relays these parameters to a computer game 705 through Internet connection 706. Game 705 includes a real personal data module 708 that stores parameters from server 704. Users of computer game 705 may select an option to invoke the parameters of module 708, thereby limiting the game as described above.

As an alternative, users of devices 702 may directly download game parameters to computer game 705, as through a local data link 710. Users may also type game parameters directly into module 708. In either case, computer game 705 has real limiting functions to gaming actions via the invention. Preferably server 704 controls the download of data to computer game 705 so that data is controlled and collated in a master database for other uses and competitions.

System 700 can further network with an arcade game 720 in a similar manner, such as through Internet connection 718. Real performance data is again stored in real personal data module 722 in game 720 (or at the computer controlling game 720) so that users have restrictions upon play. User ID codes facilitate storing and accessing data to a particular person. In this way, users of arcade games can access and limit their games to real data associated with their skill. Competitions between players at arcade games, each with their own real personal data in play, increase the competitiveness and fairness of game playing.

Figure 50:
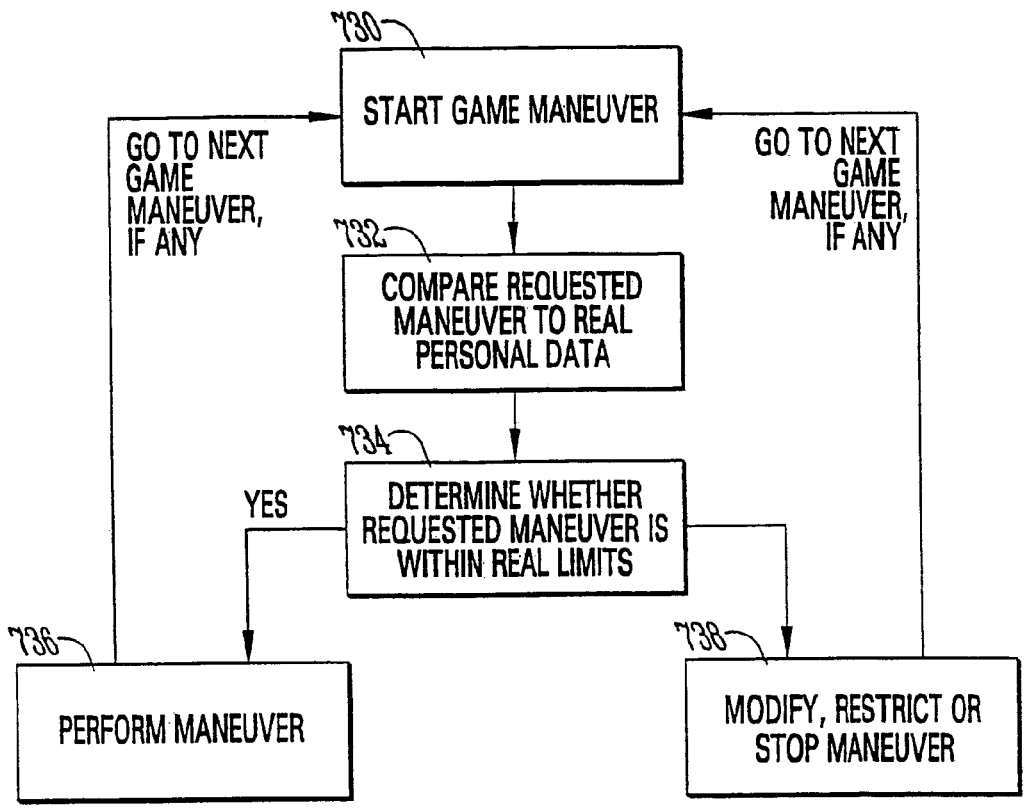
FIG. 50 schematically shows one flow chart implanting game algorithms in accord with the invention.

FIG. 50 illustrates a simplified flow chart of game operation such as described above. A start of a game maneuver starts at step 730. A start may be initiated by a joy stick action, or button action, for example. Prior to performing the action, the game compares the desired game maneuver with real personal data, at step 732. At step 734, a comparison is made to determine whether the requested maneuver is within preselected limits (e.g., within a certain percentage from real personal data) related to the real personal data. If the answer is yes, then the game performs the maneuver, at step 736. If the answer is no, then the game modifies, restricts or stops the maneuver, at step 738.

Figure 51:
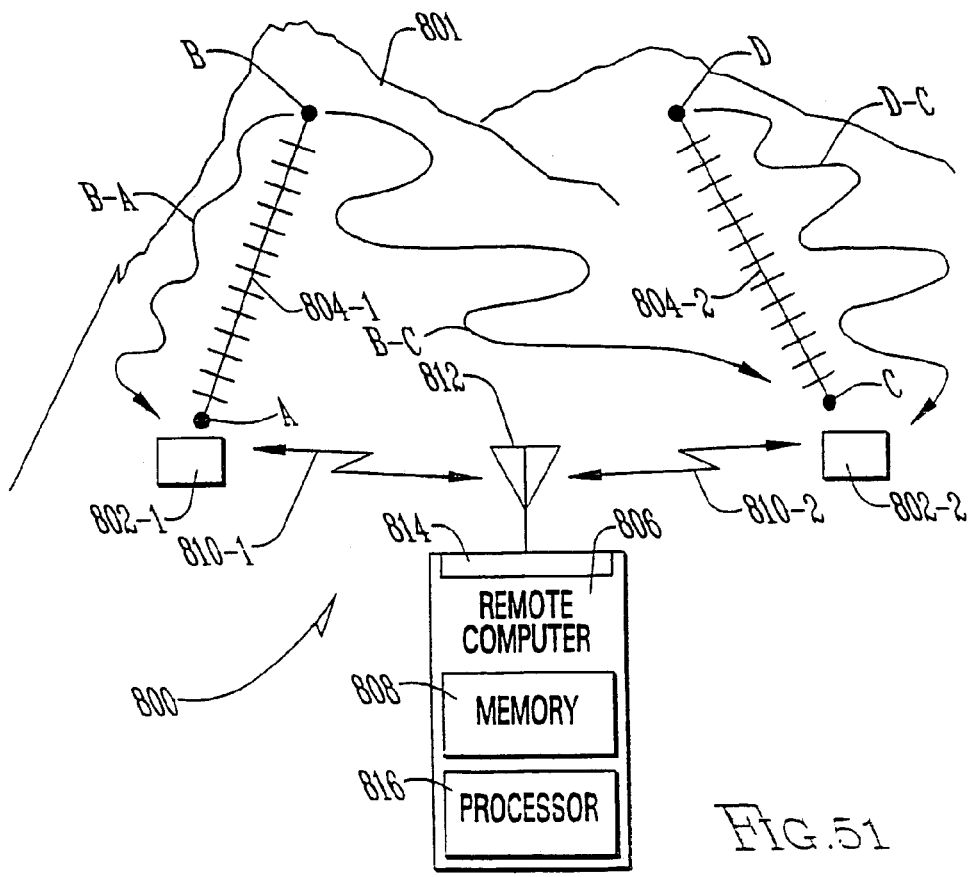
FIG. 51 shows one speed detection system for a ski resort in accord with the invention.

FIG. 51 shows one speed detection system 800 constructed according to the invention. System 800 includes a ticket reader 802 for each ski lift 804. For example, reader 802-1 covers ski lift 804-1 to read tickets of persons riding ski lift 804-1; reader 802-2 covers lift 804-2 to read tickets of persons riding lift 804-2. Lift 804-1 carries persons (e.g., skiers and snowboarders) between locations "A" and "B"; lift 804-2 carries persons from locations "C" to "D". These persons travel (e.g., by ski or snowboard) from location B to A by approximate distance B-A, from location B to C by approximate distance B-C, from location D to A by approximate distance D-A, and from location D to C by approximate distance D-C.

Approximate distances B-A, B-C, D-A, D-C are stored in remote computer 806. Specifically, computer 806 has memory 808 to store distances B-A, B-C, D-A, D-C. Computer 806 and readers 804 preferably communicate by wireless data 810-1, 810-2; thus computer 806 preferably has antenna 812, and associated receiver and transmitter 814, to facilitate communications 810. Computer 806 further has a processor 816 to process data and to facilitate control of computer 806.

Figure 52:
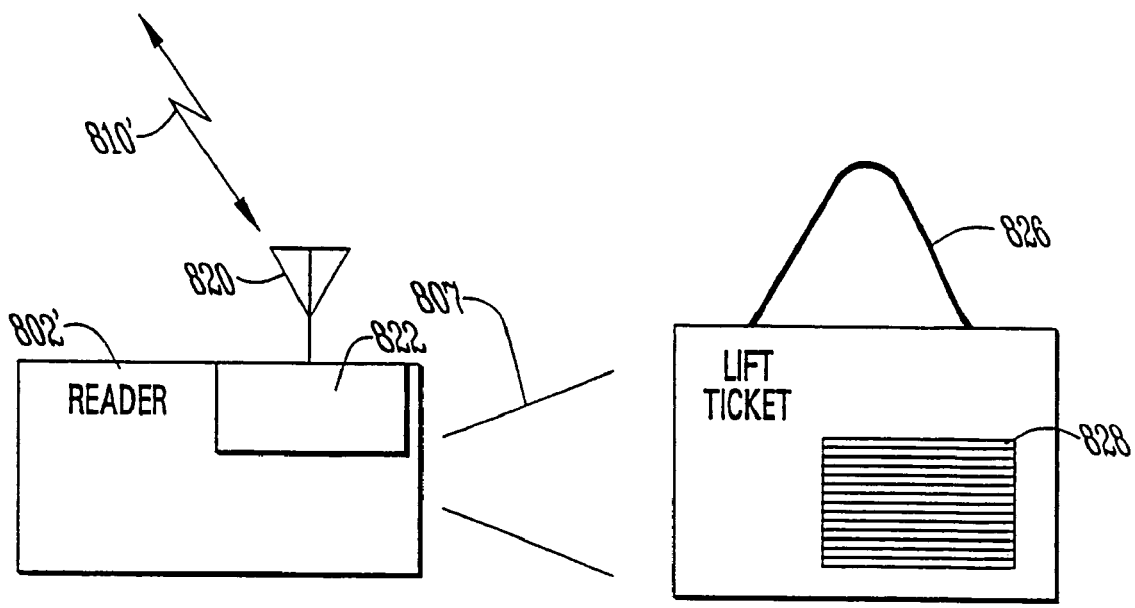
FIG. 52 shows one bar code reader suitable for use in the system of FIG. 51.

A representative reader 802' is shown in FIG. 52. Reader 802' has an antenna 820 and transmitter/receiver 822 to facilitate communications 810' with computer 806. Among other functions, reader 802' reads ski lift tickets such as ticket 826 of a person riding lifts 804 via a scan beam 807. Ticket 826 usually includes a bar code 828 read by reader 802'.

In operation, a ticket 826 is read each time for persons riding lifts 804. A time is associated with when the ticket is read and logged into computer 806. When that ticket 826 again is read, e.g., either at lift 804-1 or 804-2, a second reading time is logged into computer 806. Processor 816 of computer 806 then determines speed based upon (a) the two reading times, (b) the approximate lift time for the appropriate lift 804, and (c) the distance traveled (i.e., one of distances B-A, B-C, D-A, D-C). For example, suppose a person enters lift 804-1 at 9 am exactly and enters lift 804-2 at 9:14 am. Suppose lift 804-1 takes ten minutes, on average, to move a rider from A to B. Accordingly, this person traveled distance B-C in four minutes. If distance B-C is two miles, then that person traversed distance B-C with a speed of 30 mph. If the resort where system 800 is installed sets a maximum speed of 25 mph for the mountain 801, then that person exceeded the speed and may be expelled from the resort. Note further that the resort may specify speed zones, corresponding to each of the paths B-A, B-C, D-A, D-C. If for example path B-A has a wide path, then a speed may be set at 30 mph. A person successively repeating lift 804-1 may thus be checked for speeds exceeding 30 mph. If on the other hand path D-A has a lot of trees, then a speed of 20 mph may be set; and a rider who rides lift 804-2 and arrives at lift 804-1 can be checked for violations along route D-A.

When a ski lift 804 stops, then additional time is added to that person's journey. A feedback data mechanism tracking lift movement can augment data in computer 806 to adjust skier speed calculations on dynamic basis.

Note that system 800 serves to replace or augment sensor 231' of FIG. 10I. Since sensor 231' independently determines speed, then reader 802 may for example read sensor 231' to see whether speeds were exceeded for one or more zones. Sensor 231' may instead have a visual indicator which is triggered when a person exceeds a speed limit in any of zones for B-A, B-C, D-A, D; and a human operator sees the indicator when there is a violation.

Figure 53:
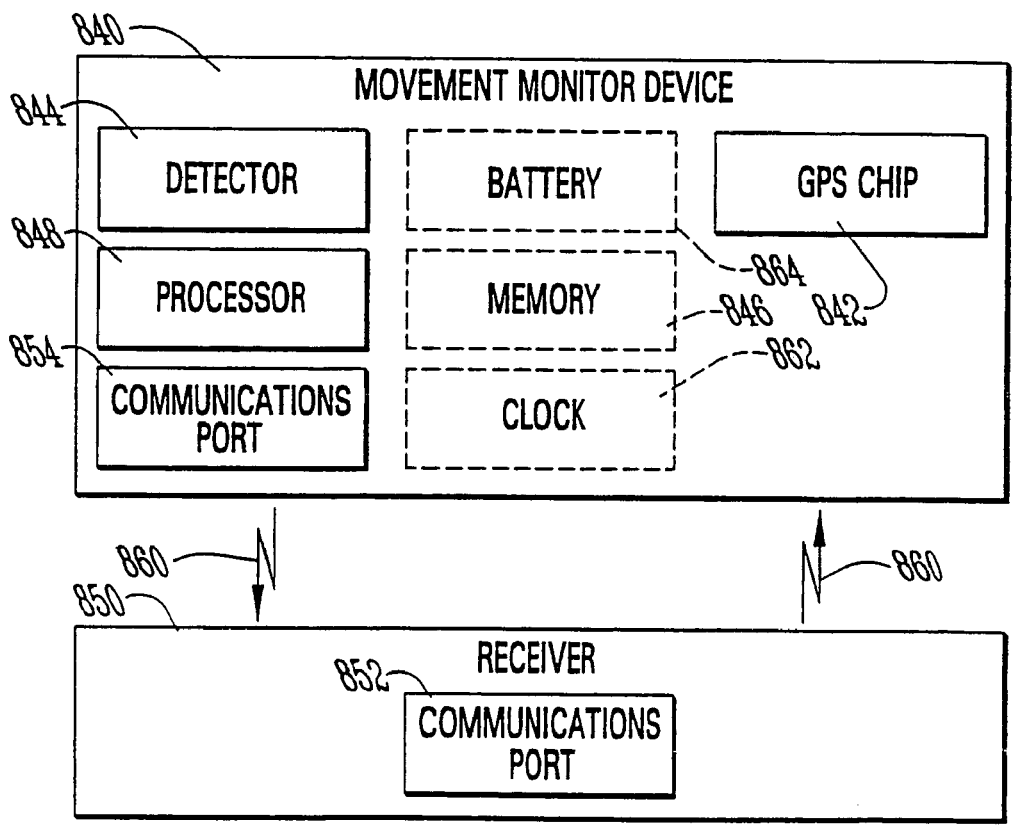
FIG. 53 shows one monitor device constructed according to the invention and incorporating a GPS receiver.

As shown in FIG. 53, one monitor device 840 of the invention incorporates a GPS receiver chip 842 to locate device 840. Device 840 is preferably integrated with an adhesive strip such as discussed in FIG. 2. Device 840 also preferably "powers on" when opened and dispensed, such as shown in FIGS. 4 and 10. In operation, device 840 is generally applied to persons or objects to assess, locate and log "events". By way of example, by attaching device 840 to a new computer shipped to a retailer, an impact event may be recorded and stored in memory 846 by an accelerometer detector 844, as described above, and a location associated with the impact event is also stored, as provided by GPS chip 842. As such, for example, the exact amount of damage received by the computer, as well as the exact location of where the damage occurred, is stored in memory 846. As described herein, other detectors 844 may be used to generate "events" (e.g., a spin event, or an airtime event, temperature, humidity, flip-over events, etc.) in conjunction with GPS chip 842. Data in memory 846 is relayed to a receiver 850 having data access codes of device 840. Alternatively, data is communicated to receiver 850 by wireless and timed-sequence transmissions. Communications ports 852, 854 facilitate data transfers 860 between device 840 and receiver 850. Transfers 860 may be one way, or two-way, as a matter of design choice. A clock 862 may be incorporated into device 840 to provide timing and/or real-time clock information used to time tag data events from one or both of detector 844 and GPS chip 842. As above, a battery 864 serves to power device 840. A processor 848 serves to manage and control device 840 to achieve its functionality.

Figure 54:
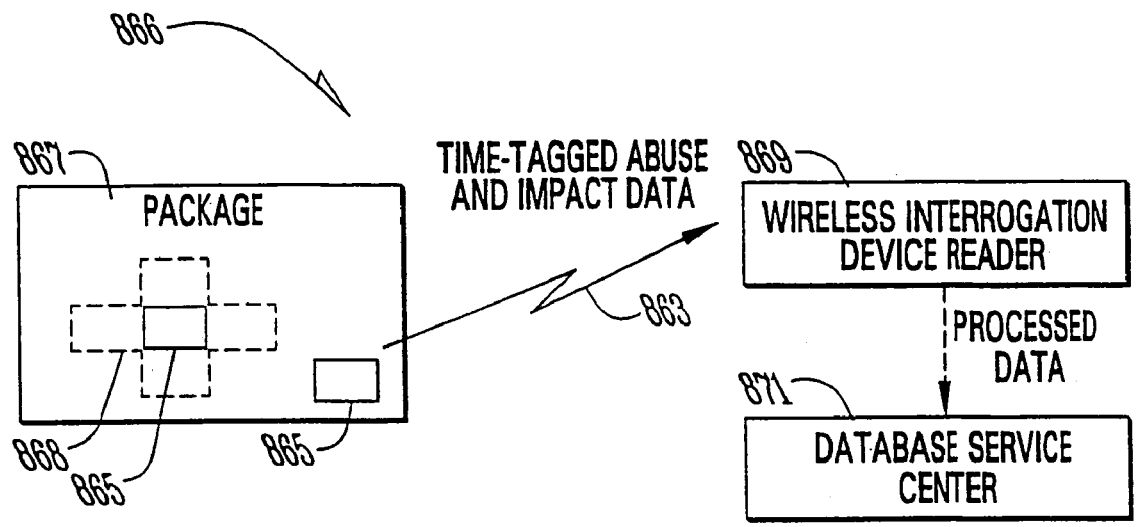
FIG. 54 shows a system suitable for use with the device of FIG. 53.

FIG. 54 shows a system 866 suitable for use with a device 840, or with other MMDs or EMDs disclosed herein. System 866 has particular advantages in the shipping industry, wherein a device 865 (e.g., device 840, or one or more EMDs or MMDs) attaches to a package 867 (or to the goods 868 within package 867) so that system 866 can monitor data associated with shipment of goods and package 868, 867. Multiple devices 865 may be attached to package 867 or goods 868 as needed or required to obtain the data of interest. Certain data determined by device 865, during shipment, include, for example, impact data or g's, temperature, data indicating being inverted, humidity and other metrics. In sum, one or more of these data are wirelessly communicated, as wireless data 863, to an interrogation device reader 869 to assess the data corresponding to shipment conditions and/or abuse of package 867 and/or goods 868. Data 863 preferably includes "time tag" data indicating when a certain "event" occurred, e.g., when goods 868 experienced a 10 g event. Preferably, data from reader 869 is further relayed to a remote database 871 so that system 866 may be operated with other similar systems 866 so as to monitor a large amount of packages and goods shipments at different locations. Damaged goods can for example be evaluated by any reader 869 and recorded into a common database 871 by the controlling company.

The invention of FIG. 54 thus has certain advantages. Companies that ship expensive equipment 868 have an incentive to prove to the receiver that any damage incurred was not the result of faulty packaging 867 or unsatisfactory production and assembly. Also, shipment insurers want to know when and where damage occurs, so that premiums may be adjusted appropriately or so that evidence may be offered to encourage the offending party to improve handling procedures.

Figure 55:
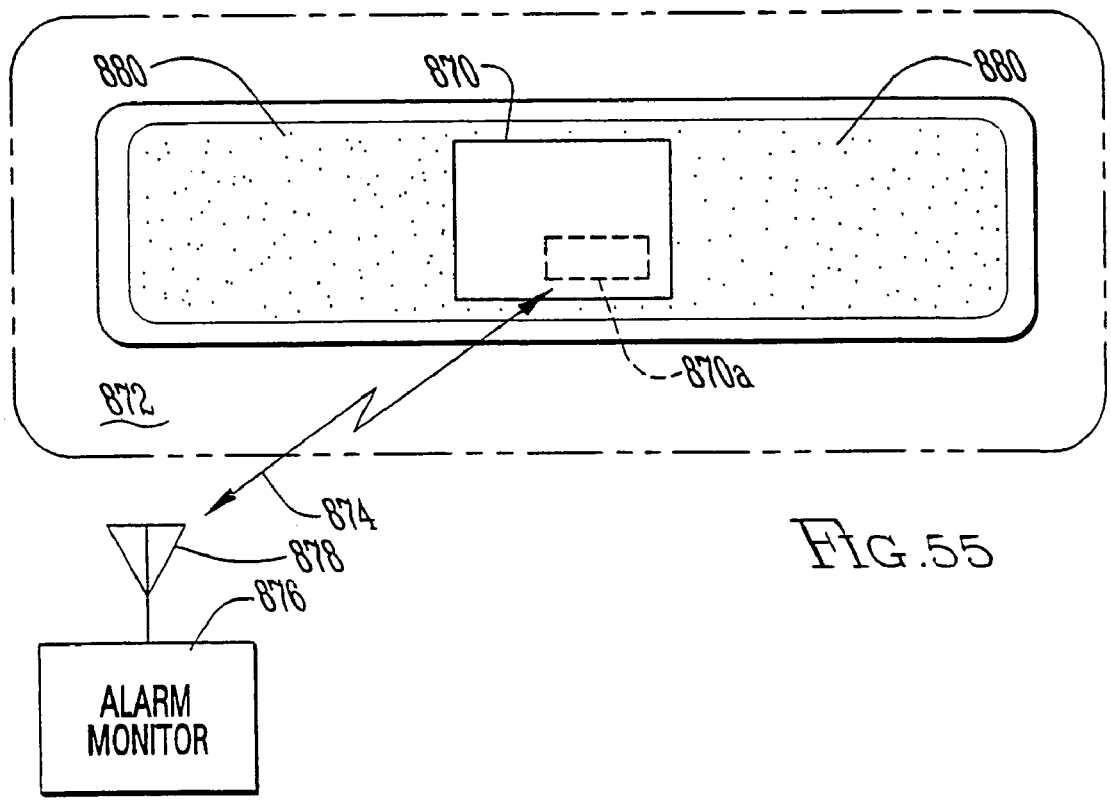
FIG. 55 shows an infant monitoring system constructed according to the invention.

The monitor devices of the invention have further application in medicine and patient health. One monitor device 870 of the invention is shown in FIG. 55. Specifically, device 870 attaches to a baby's body 872 (e.g., to a baby's chest, throat, leg, arm, buttocks or back) to monitor movement such as respiratory rate, pulse rate, or body accelerations. Device 870 of the preferred embodiment synchronizes to repetitive movements (e.g., pulse rate or respiratory rate) and generates an "event" in the absence of the repetitive movements. Device 870 can for example be device 10*w*, FIG. 2E, facilitating easy placement on the infant by the adhesive strip (which is also beneficially sterilized) to measure heart rate as an event.

Device 870 can alternatively be a monitor device using a microphone to detect "breathing" as a health metric for the infant. Regardless of the metric, the event reported by device 870 is preferably communicated immediately as wireless signals 874 to a remote monitor 876, with an antenna 878 to receive signals 874. Monitor 876 is preferably portable so as to be carried with the infant's parents. Monitor 876 generates an audible or visual alarm when an event is received from signals 874. Device 870 seeks to address the very realistic concern of parents relative to Sudden Infant Death Syndrome, or other illnesses. Device 870 preferably relays a warning event data to alarm monitor 876 within seconds of detecting trouble with the infant. For example, if device 870 detects the absence of heart rate or breathing, the alarm at monitor 876 is made in near real time.

Like other monitor devices herein, device 870 has a detector 870*a* to detect the desired metric. For purposes of illustration, other elements such as the device's communications port and processor are not shown, though reference may be made to FIG. 1 to construct device 870. In one embodiment, detector 870*a* is a piezoelectric element that generates a voltage signal at every pulse or breath of baby 872, such as shown and described in FIG; 7-7B. Detector 870*a* may alternatively be an accelerometer arranged to sense accelerations of the infant's chest (or other body portion); and thus chest (or other body portion) accelerations are used to determine the repetitive signal (or simply movement or absence of movement). Preferably, the sensitive axis of the accelerometer is perpendicular to baby body 872. For example, such an accelerometer can be used to sense accelerations of the baby's chest, rising and falling. In still another embodiment, detector 870*a* is a force-sensing resistor or electro-resistive element generating signals responsive to force or weight applied to device 870. Such a device is useful to sense when baby body 872 rolls onto device 870. Yet another detector 870*a* is a Hall Effect detector; that detector within device 870 detects when baby body 872 inverts, that is when the baby rolls over. A roll over event is one particular event of interest by parents; and in this embodiment, a warning signal 874 is generated at each roll over. Detector 870*a* can alternatively be a microphone; and the device's processor processes the sound data to detect recurring audible data indicative of breathing sounds.

Preferably, device 870 is integrated with an adhesive strip 880; and device 870 and strip 880 form an adhesive bandage monitor device such as described above in connection with FIGS. 2-2D, 8C. Device 870 and strip 880 are also preferably packaged so as to "power on" when dispensed or used. A wrapper such as described in FIGS. 4-4A may be used; or preferably device 870 and wrapper 880 dispense from a canister 200, 200' such as described above in FIGS. 10-10F. In this way, device 870 is conveniently dispensed and applied to baby body 872, and without contamination and germs.

Those skilled in the art should appreciate that device 870 may also attach to the infant in a variety of places depending on the parent's desire. Device 870 may for example attach to the back or bottom of the infant, and generate an event for every time the infant rolls over.

Figure 56:
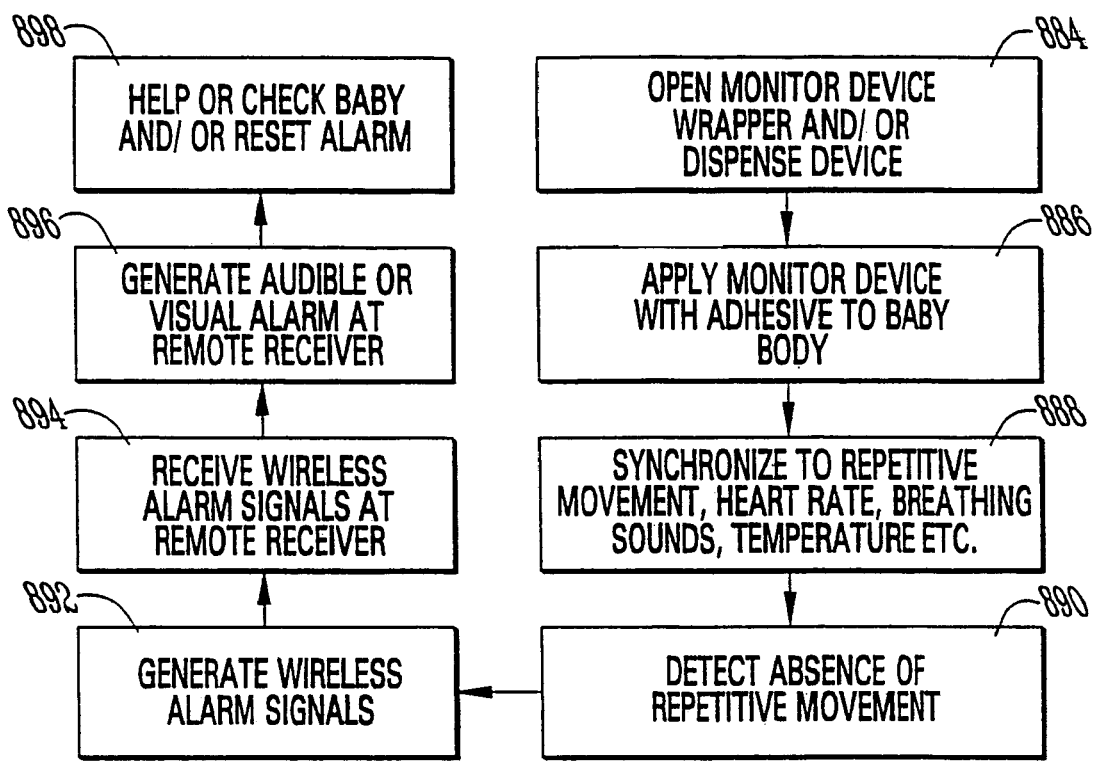
FIG. 56 schematically shows a flow chart of operational steps used in the system of FIG. 55.

FIG. 56 shows a flowchart of steps associated with applying and using one monitor device according to the invention. At start 884, the device is unwrapped and/or dispensed from a container. The device is then applied to a baby's body, preferably as an adhesive bandage package, in step 886. Once applied, the device synchronizes to baby body movement (such as repetitive movements associated with pulse or respiratory rate), breathing sounds or heart rate, in step 888. The device then searches for "events" in the form of the absence of repetitive signals, indicating for example the danger of an absence of pulse, heart rate or respiration, in step 890. In step 892, the monitor device generates a wireless signal as a warning; that signal is received at a remote receiver at step 894. Once received, remote receiver generates an audible alarm (e.g., a buzzer sounds) or visible alarm (e.g., an LED is lit), in step 896. Preferably, steps 890-896 occur in less than one or several seconds (e.g., less than five or ten or fifteen seconds). Once the alarm occurs, a parent checks the infant (step 898) to determine whether the alarm is real and, if needed, to administer aid. If for some reason the alarm was incorrect, the remote receiver is reset (step 898) and the monitor device continues to assess distressing situations to generate events.

As an alternative, the detector of the monitor device (FIG. 55) is a temperature (or alternatively a humidity) detector, and the alarm monitor merely tracks infant temperature for worried parents; such a device is useful for sick infants in particular. The temperature sensor can be coupled with other detectors (e.g., heart rate) to provide multiple functions, if desired.

The MMDs and EMDs of the invention thus have several other advantages. They may be used discretely and safely as medical diagnostic and monitoring detectors. With appropriate detectors, EMDs of the invention can for example provide for portable, wireless pulse oxymeters or blood glucose monitors. With the appropriate detectors in MMDs, rehabilitation clinicians would be able to quantitatively monitor metrics such as limb movement and balance. EMDs equipped with certain detectors may find use as real time, remote and inexpensive pH monitors and blood gas monitors.

Figure 57:
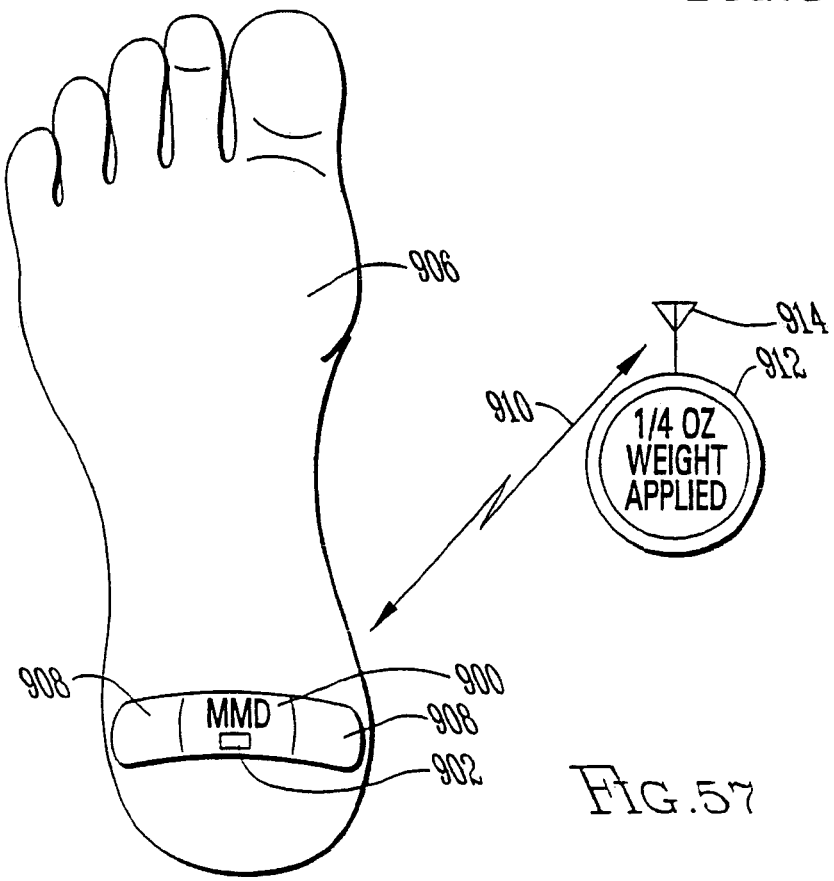
FIG. 57 shows one MMD of the invention used to gauge patient weight.

One MMD 900 of the invention and useful in medical applications is shown in FIG. 57. MMD 900 is similar to device 10 of FIG. 1, but in addition (or alternatively) has a detector 902 that senses weight. Detector 902 for example is a force sensing resistor or electro-resistive device. Preferably, MMD 900 is applied to one or more locations at the bottom of a human foot 906 via attachment with adhesive strips 908. Those skilled in the art should appreciate that MMD 900 can alternatively be located at other locations on the human body. On the occurrence of an "event", MMD 900 generates wireless signals 910 for receipt at a remote receiver 912, here shown in the form of a watch with antenna 914. Watch 912 is generally worn by the person having foot 906.

MMD 900 is preferably in the form of a MMD 10*z* of FIGS. 2B-2C, though with a weight sensing detector. In operation, MMD 900 is first calibrated: all the weight of person with foot 906 is applied to MMD 900 so that detector 902 is calibrated to that entire weight. Alternatively, a separate weight simply calibrates MMD 900. Thereafter, MMD 900 generates "events" corresponding to fractions of the entire weight that the person with foot 906 applies to MMD 900. For example, one MMD 900 generates wireless data 910 each time MMD 900 experiences at least one-fourth the entire weight; that data 910 is converted and displayed on receiver 912, as shown. In this way, when a cast is applied to a person, MMD 900 may be applied under foot, so that the person may obey doctor's orders to put no more than ¼ weight on foot 906, for example. As an alternative, MMD 900 is already calibrated to certain weights, e.g., 200 lbs, 180 lbs, etc. A pre-calibrated MMD 900 may then be applied to 200 lbs persons to generate events as needed. For example, an MMD 900 is used effectively to generate an event, to inform the person, that ½ or ¾ of the person's entire weight is on one foot.

Figure 58:
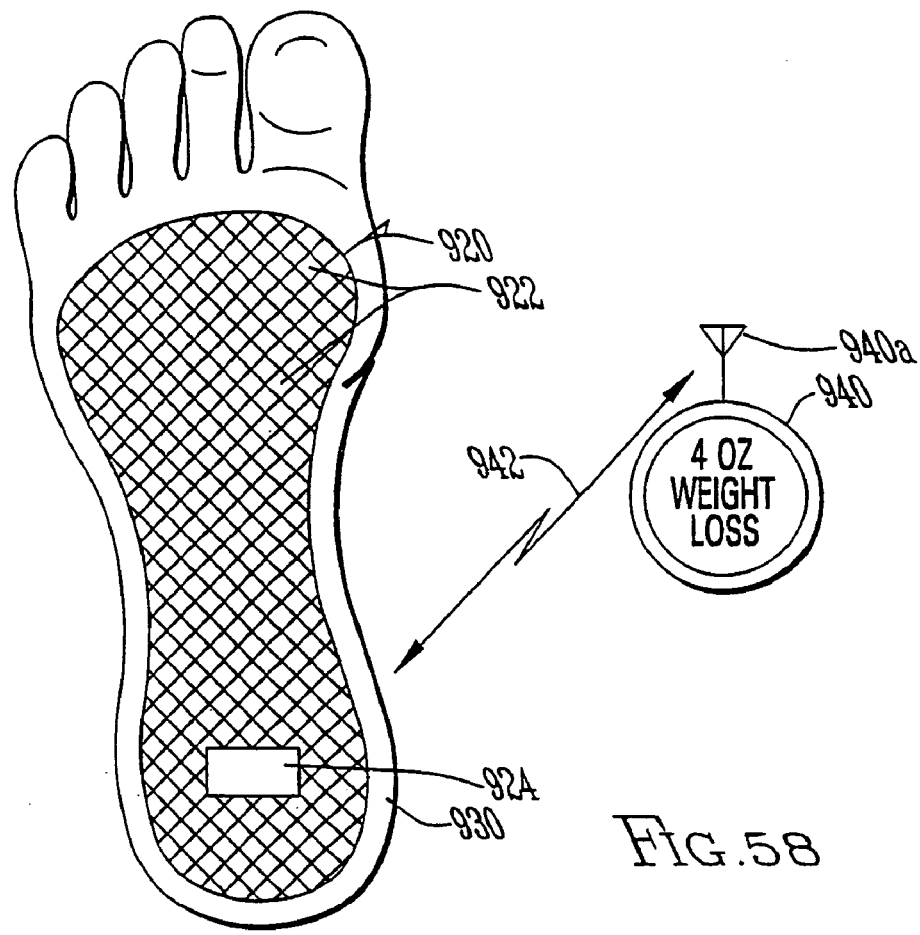
FIG. 58 shows a weight monitoring system constructed according to the invention.

A weight sensing MMD may also take the form of MMD 920, FIG. 58. Here, MMD 920 has an array of detectors 922. Detectors 922 may be force sensing resistors or other weight sensitive elements. Detectors 922 collectively and electrically couple to processor 924. Other elements (not shown)

connect with processor 924, e.g., a communications port and battery, such as monitor device 10 of FIG. 1. In operation, MMD 920 senses weight applied to foot 930 while walking or standing. Over time, MMD 920 ascertains the actual weight of the person of foot 930. Once weight is determined, MMD 920 relays weight information to a remote receiver, e.g., watch 940 with antenna 940a, via wireless signals 942. Receiver 940 displays pertinent data, e.g., what fractional weight is applied onto foot 930.

Figure 59:
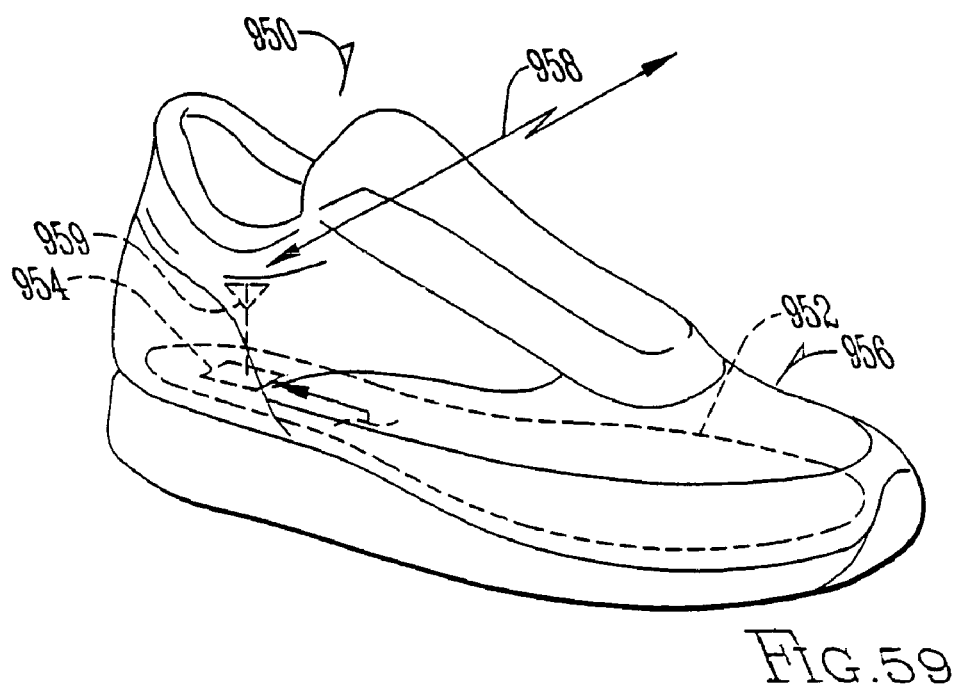
FIG. 59 shows another weight monitoring system of the invention.

In this way, a person may track his or her weight at any time. MMD 920 and receiver 940 may also communicate two-way, so that watch 940 queries MMD 920 for weight data, thereby conserving battery power. Those skilled in the art should appreciate that MMD and receiver 920, 940 may be configured differently and still be within the scope of the invention. In one embodiment, MMD 920 is integrated with a shoe pad insert to fit into any shoe. Alternatively, MMD 920 is integrated directly into a shoe, as shown in FIG. 59. Detector 922 may also have fewer or more detectors depending upon design placement of detectors relative to foot 930; that is, a single detector can be used to measure weight if arranged to accurately detect all or part of a person's weight. In such a configuration, MMD 920 may take the form of an adhesive bandage monitor device with a single detector and applied to the sole of a foot, as shown in FIG. 57. Preferably, weight is calibrated prior to use (e.g., when shoe is lifted off the ground) so that weight is determined relatively. In another embodiment, selectively positioning elements 922 to high impact areas of foot 930 (e.g., at the ball and heel of foot 930), the invention monitors impact and improper walking or running events so as to provide corrective feedback to users or doctors.

FIG. 59 shows a shoe-based weight sensing system 950 constructed according to the invention. System 950 has one or more weight sensing detectors 952 coupled to a processing section 954 (and, as a matter of design choice, other components such as shown in device 10 of FIG. 1)—all arranged with a shoe 956 (or within an insert for shoe 956). In operation, shoe 956 generates wireless signals 958 for a remote receiver (e.g., watch 940, FIG. 58) to inform the person wearing shoe 956 of his or her weight or weight loss. By integrating a transceiver and antenna 959 with processing section 954, the remote receiver interrogates shoe 956 for weight information. In this way, health conscious persons can wear shoe 956 and learn of their weight at any desired time. Such a shoe 956 is for example useful in determining weight loss. By way of example, a runner may use shoe 956 to determine weight loss in ounces, informing the runner that he or she should drink replacement water. Accordingly, in the preferred embodiment, a runner first calibrates his or her weight prior to a race; then system 950 reports weight loss relative to the calibrated weight. Those skilled in the art should appreciate that alternatives from the foregoing may be achieved without departing from the scope of the invention.

Figure 60:
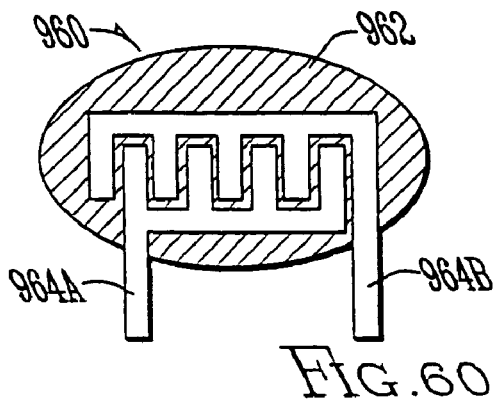
FIG. 60 shows a force-sensing resistor suitable for use in the weight monitoring systems of FIG. 58 and FIG. 59 and in the MMD of FIG. 57.

FIG. 60 shows one force-sensing resistor 960 suitable for use with the systems and/or MMD of FIGS. 57-59. Resistor 960 includes resistive material 962 and interdigitated contacts 964A, 964B; material 962 forms an electrical path between contact 964A and contact 964B. In operation, a force applied to resistor 960 increases the conductivity in the path between contacts 964A, 964B. By measuring resistance or conductance between contacts 964A, 964B, the applied force onto resistor 960 is known. Typically, resistor 960 is calibrated so that a particular resistance translates into and applied force; as such, a processor such as processor 954 or 924 may be used to monitor and report force at any given time. In one embodiment, force is reported to users in pounds, providing a typically used weight designation for such users.

Preferably, resistor 960 includes flexible polymers as active spring agents as the sensing element for loading conditions. Such polymers provide load-sensing resistors with enhanced performance and with preferable mechanical characteristics.

Figure 61:
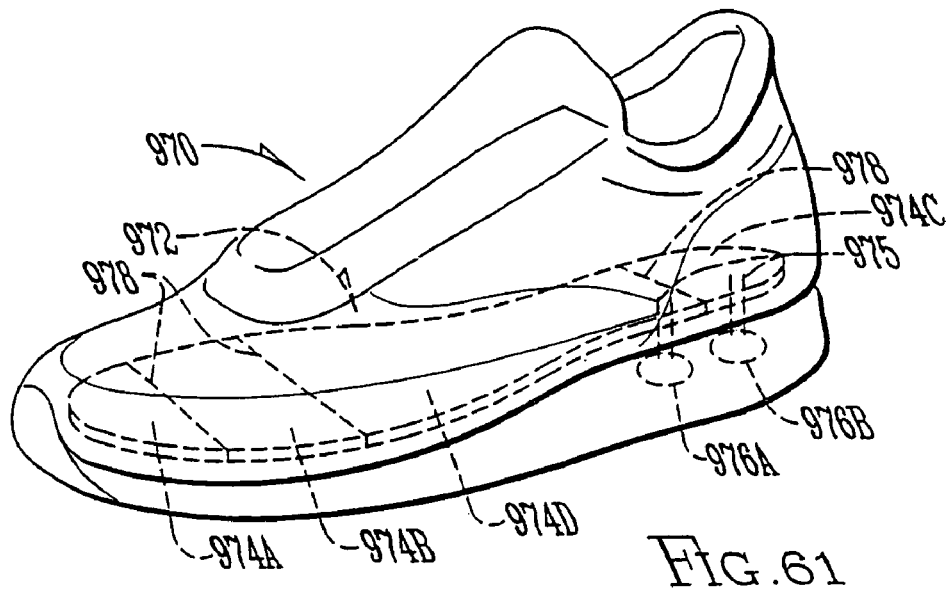
FIG. 61 shows one weight-sensing device in the form of a shoe or shoe insert, in accord with the invention.

FIG. 61 shows another weight sensing device 970 constructed according to the invention. Device 970 is formed of a shoe 972 and includes a fluid cavity 974 that displaces and pressurizes with applied force—a force such as provided by a user wearing shoe 972. A pressure sensor 976A coupled with cavity 974, through a small conduit 975, measures pressure. A processor (e.g., processor 954, 924 above) coupled with sensor 976A monitors pressure signals and converts the signals to weight. As above, preferably device 970 is calibrated such that a particular pressure corresponds to a particular weight. Preferably, and for increased accuracy, cavity 974 does not completely displace away from any portion of cavity 974 when a user applies weight to cavity 974 while wearing shoe 972.

As an alternative to a single cavity 974, cavity 974 can also be made up of separate fluid cells, as exemplified by sections 974A, 974B, 974C, and 974D, and multiple sensors 976A, 976B. In this embodiment, cavity membrane walls 978 separate sections 974A, 974B, 974C, 974D; optionally two or more of sections 974A, 974B, 974C, 974D have an individual pressure sensor monitoring pressure of the particular section, such as sensor 976A for section 974D and sensor 976B for section 974C. This embodiment is particularly useful in providing highly accurate weight sensing for a user of shoe 972. Each fluid cell 974A-D may for example have differing pressurization characteristics to manage the overall weight application of a human foot. For example, cells 974B, 974C may be formed with higher pressure cavities as they are, respectively, under the ball or heel of the foot and likely have to accommodate higher pressures (i.e., higher applied weight to those sections). In either event, a processor connected to the several pressure sensors 976A, 976B beneficially determines weight as a combination of different pressures of the different fluid cells. Alternatively, a single pressure sensor 976A may be used to sequentially measure pressure from various fluid cells 974A-D; and the processor (not shown) then determines weight based upon the several measurements.

Those skilled in the art should appreciate that the number of cells 974A-D, and the number of sensors 976A, 976B, are a matter of design choice and do not depart from the scope of the invention; more or fewer cells 974 or sensors 976 may be used without departing from the scope of the invention. Those skilled in the art should also appreciate that a shoe insert can alternatively house cavity 974 (and/or sections 974A, 974B); for example, shoe 972 can for example be a shoe insert instead of a shoe—constructed and arranged such that a user applies weight on cavity 974 in use.

A weight-sensing device of the invention, for example as set forth in FIG. 61 may benefit from additional information such as temperature, as fluid pressure characteristics vary with temperature. Accordingly, in one embodiment of the invention, an additional detector is integrated with the processor to monitor temperature. As such, a device 970 for example can include one or more pressure detector 976 and a temperature detector (not shown), both of which input data to the processor for processing to determine weight applied to cavity 974 (or sections 974A-D).

Figure 62:
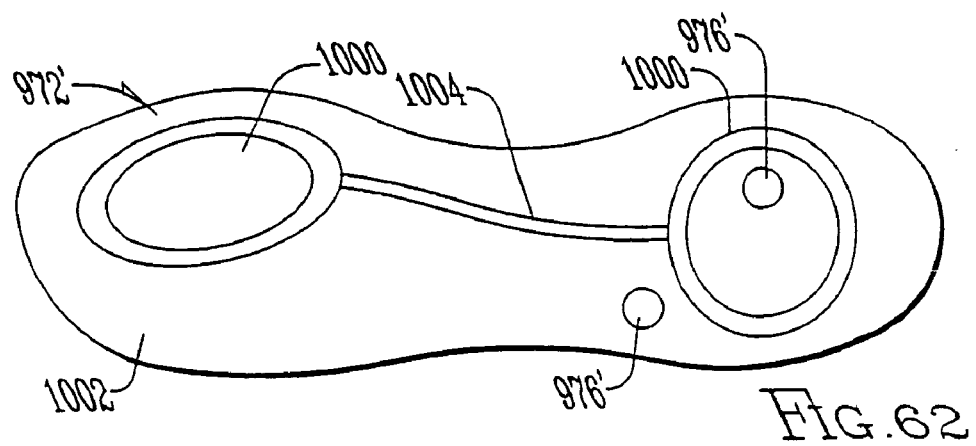
FIG. 62 illustrates fluid cavities suitable for use in a device of FIG. 61.

FIG. 62 shows an alternative arrangement of fluid sections 974' (e.g., shown as fluid sections 976', 1000, 1004) integrated with a shoe insert 972'. Preferably, sections 974' are integrated within insert 972', though FIG. 62 shows sections 974' external to insert 972' for purposes of illustration. In operation, a user stepping on insert 972' pressurizes the various sections 974'—and a processor (not shown) determines weight based upon pressure data from pressure sensors 976' connected with the various sections 974'. Higher pressure areas 1000 and lower pressure areas 1002 are then preferably measured by separate pressure sensors 976'. One or more pressure conduits 1004 may be used to couple like-pressure areas so that a single sensor 976' monitors a single like-sensor area.

The invention thus has several advantages in regard to weight loss, monitoring and human fitness. In accord with the above invention, a user of a weight monitoring system or device disclosed herein can review his or her weight at nearly any time. Runners using such a system and device to know their hydration loss; chiropodists may wish to monitor weight distribution over a patient's feet; and athletic trainers may wish to analyze weight distribution and forces. The invention of these figures assists in these areas. In making these measurements, force-sensing resistors may be used; but strain gauge pressure sensors in the shoe may also be used. Preferably, in such embodiments, the bottom surface of the foot is covered by sensors, as weight is not often evenly distributed. Accordingly, a single sensor may not encompass a preferred arrangement, and therefore multiple sensors are preferred in the sole of the shoe (or in a shoe insert), with the results of all sensors summed or combined to a single "weight" answer. In one embodiment, only a portion of the foot need to be covered, covering a certain percentage of the overall weight; and that percentage is scaled to a user's full weight. Weight and compression forces monitored in a shoe or shoe insert, in accord with the invention, can further assist in gauging caloric and/or physical effort.

Figure 63:
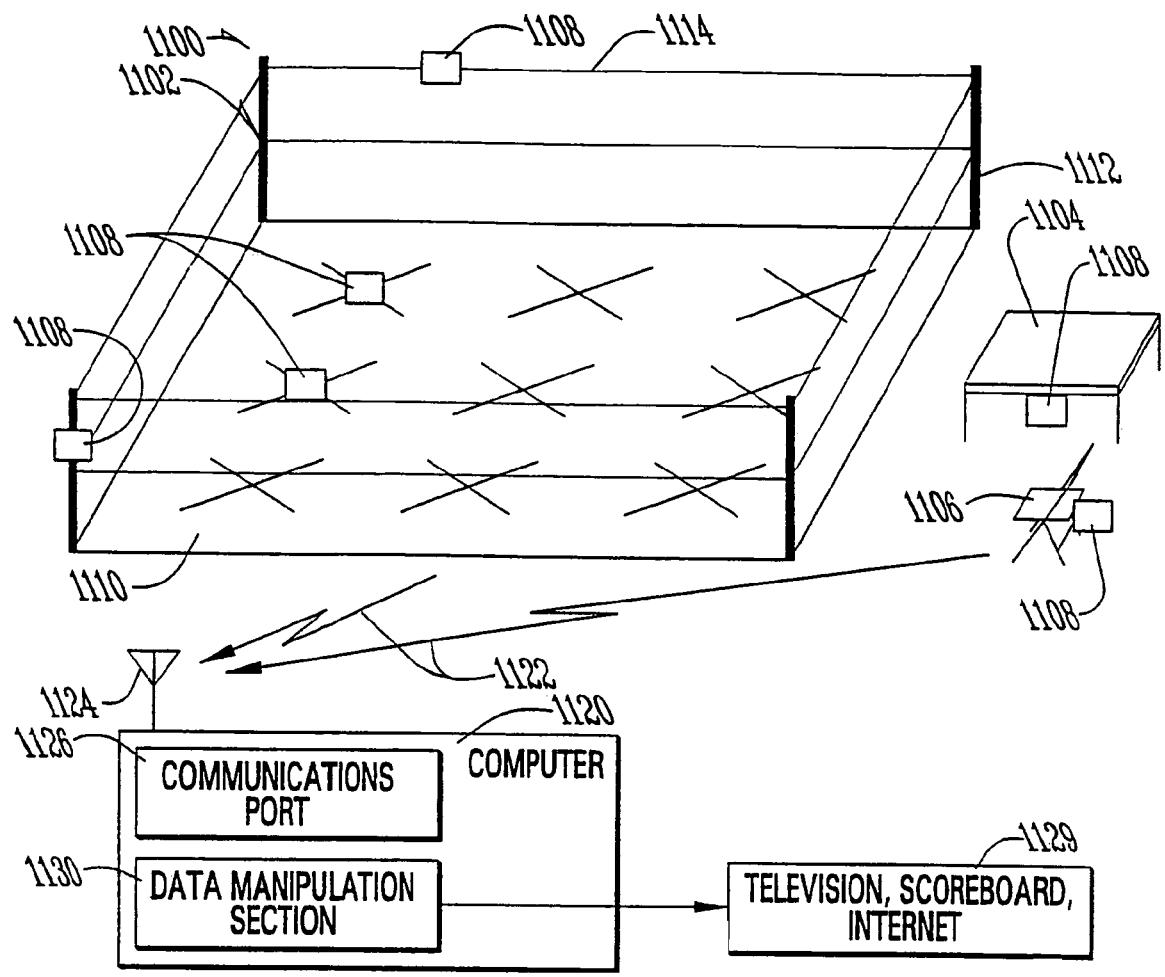
FIG. 63 shows a wrestling performance monitoring system constructed according to the invention.

FIG. 63 shows a professional wrestling rink system 1100 constructed according to the invention. System 1100 has a rink 1102 within which professional wrestlers compete (oftentimes theatrically). Adjacent rink 1102 are tables 1104 and chairs 1106, sometimes used in conjunction with rink 1102 (e.g., items 1104 and 1106 are sometimes used to smash over a wrestler as part of a performance). A plurality of sensors (e.g., MMDs or EMDs) 1108 are placed (attached, stuck to, etc.) throughout rink, table and/or chairs 1102, 1104, 1106. For example, in one preferred embodiment a plurality of MMD sensors 1108 are placed under rink canvas 1110, such as at positions marked "X", so as to report "impact" of wrestlers in rink 1102. MMD sensors 1108 may also be placed on one or more of the corner posts 1112 or ropes 1114—used to form rink 1102. Sensors 1108 are shown illustratively in a few positions about items 1102, 1104, 1106, 1110, 1112, 1114 for purposes of illustration—when in reality such sensors 1108 would be difficult to see, or would be hidden from view (for example, sensors 1108 are preferably under canvas 1110).

Data from sensors 1108 typically include information such as impact, as described above. Events associated with "impact" are communicated wirelessly to a receiving computer 1120 as wireless data 1122. Data 1122 for example includes digital data representing impact data received at any of sensors 1108 when wrestlers hit canvas 1110, move ropes 1114, or hit post 1112. Receiving computer 1120 preferably has an antenna 1124 and communications port 1126 to receive data 1122. Computer 1120 typically re-processes and then retransmits data 1122 to a media site 1129, such as television, scoreboard or the Internet, so that viewers may see data 1122 associated with wrestling at rink 1102. Since wrestling in and about rink 1102 is often based on choreographed action, computer 1120 preferably includes a data manipulation section 1130 which post processes data 1122 in predetermined ways. For example, section 1130 may apply an exponential or quadratic function to data 1122 so that, in effect, and by way of example, a 25 g impact on canvas 1110 is reported as a 25 g impact, but a 50 g impact on canvas 1110 is reported as a 1000 g impact.

Figure 64:
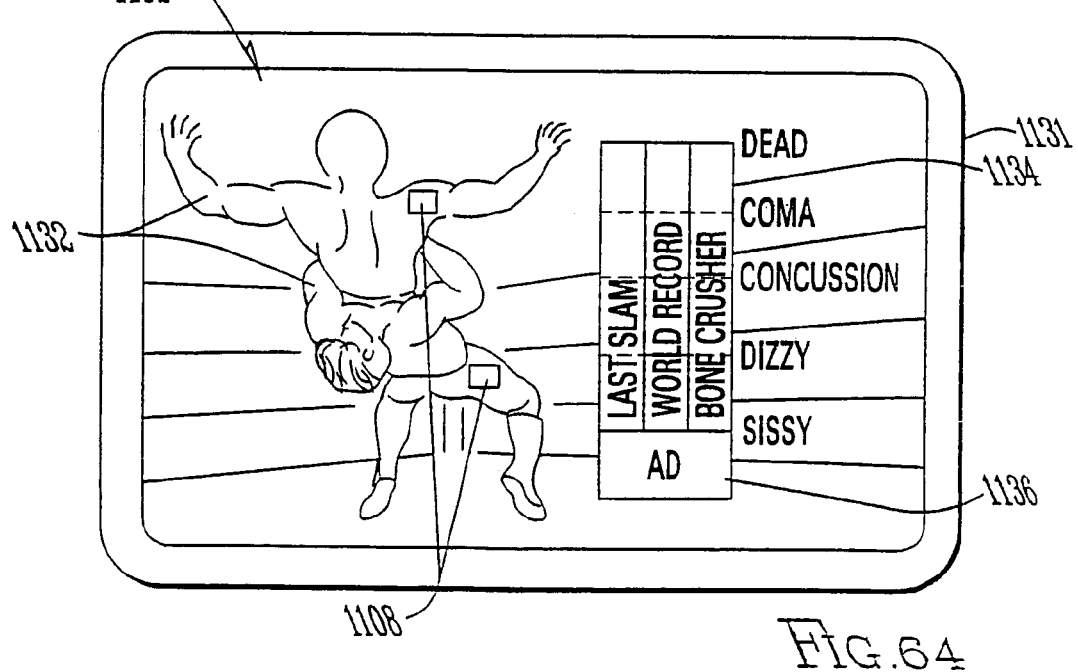
FIG. 64 shows a representative graphic output from the system of FIG. 63.

Section 1130 may also manipulate data for a particular player. For example, FIG. 64 shows a representative television display 1131 that includes data from system 1100. FIG. 53 also shows representative wrestlers 1132 in rink 1102. In a preferred embodiment, one or more sensors 1108 are also placed on wrestlers 1132, such as shown, to monitor events such as impact received directly on wrestlers 1132. In one embodiment, sensors 1108 of FIG. 64 are of the form of an adhesive bandage MMD, described above. In another embodiment, sensors 1108 are integrated into the waistband of the wrestler; this has advantages as being close to the wrestler's center of gravity and is thus more representative of total impact received by a particular wrestler.

Data from computer 1120 is thus reported to a media destination 129 such as television so that it may be displayed to audience members. FIG. 64 shows one exemplary data display 1134 overlaid with the actual wrestling performance—for television display 1131- and showing impact data in "qualitative" bar scales. Display 1134 may include qualitative wording such as shown. Display 1134 also preferably includes an advertiser overlay 1136 promoting a certain brand; typically that advertiser pays for some or all of the content provided for by system 1100 and shown in display 1134.

Thus, FIGS. 63 and 64 demonstrate benefits in which the TV viewer desires to see information such as a display of forces acting on wrestlers in real- or near real-time; the data being presented in graphical or numeric form and with a range of possible analyses performed on the forces such as latest, largest average and total. These forces typically act in at least two planes i.e. from the side and from the front or back, though the invention may also take account of forces in all three planes. Typically, the forces of interest are those acting on the main mass (torso) of the wrestler, while flailing feet and arms are not generally as important as body slams. The system of the invention thus resolves forces on individuals and can detect the force of collision between two wrestlers.

In the preferred embodiment, at least one sensor 1108 attached to ropes 1114 preferably takes the form of a long thin sensor (e.g., 0.5"×3") with a short piece wire (e.g., 3") protruding from one end to function as the antenna. This sensor's electronics utilizes a small low power accelerometer as the sensing detector, and incorporates a simple gain block, a small micro controller such as Microchips' PIC12LC672, and a small low power transmitter such as RFMs' RX6000 or RF Solutions' TX1. These electronics mount on flex circuit (e.g., as shown in FIG. 48) to allow for the excessive bending forces likely to be encountered. The power source is preferably a single small (thinnest available) lithium cell.

In the preferred embodiment, at least one sensor 1108 attached to posts 1112 incorporates a gas pressure sensor as the detector; such a sensor is incorporated into the cushions protecting the corner posts 1112 and thus registers an increase reading as the wrestlers collide with the posts Alternatively, such a sensor may be incorporated directly into a cushion attached to post 1112; preferably such a cushion is airtight. FIG. 61 shows one fluid-based pressure sensor that may be configured to such an application as the cushion with post; gas may for example replace the fluid or gel of FIG. 61. In an alternative configuration, sensors 1108 integrated with the posts 1112 may include strain gauges as the detector. Mounted directly to the posts 1112, these sensors indicate the forces acting on the post as the wrestlers impact the posts 1112. In another alternative, a post sensor may include vibration or accelerometer detector so that the sensor 1108 determines impact forces.

In one embodiment, at least one of the sensors attached to ropes 1114 include extension detectors (or LVDT devices) at the points where the ropes are mounted. Sensors 1108 with strain gauges may also be used. Sensors attached to ropes 1114 preferably detect "rope deflection" as a reported metric.

In one embodiment, sensors 1108 in the floor incorporate piezoelectric cables mounted as an interlocking grid attached to the underside of the floor. For example, such cables connect the "x" locations of FIG. 63. In such a configuration, only one sensor 1108 may be needed to monitor floor impact as all cables act as a single "detector" for a MMD sensor 1108. Floor or canvas sensors 1108 may also incorporate strain gages attached in an array on the underside or around the perimeter at points where the floor 1110 is suspended. Vibration sensors and accelerometers may alternatively be used as the detector in any floor-monitoring sensor 1108.

Figure 65:
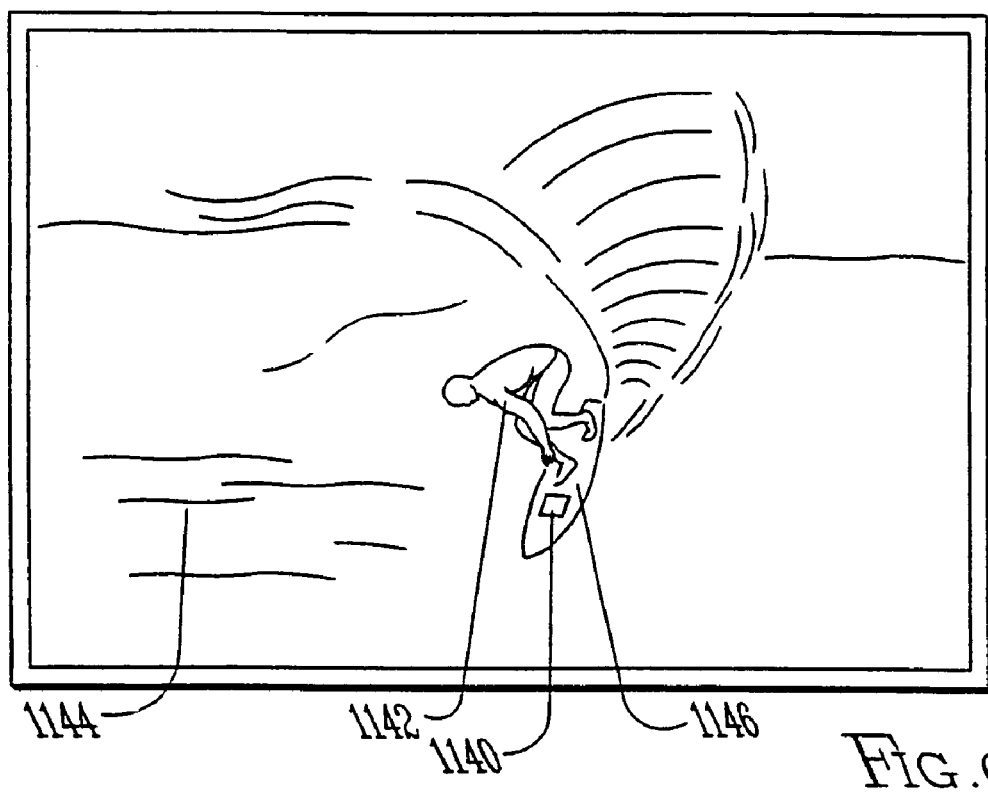
FIG. 65 shows a surfing event system according to the invention.

FIG. 65 shows one surfing application for a MMD 1140 of the invention. MMD 1140 of one preferred embodiment includes an accelerometer detector (e.g., as in MMD 10 above) and MMD 1140 determines "G's" for big bottom turns. On-board signal processing for example preferably determines the location of a big bottom turn and records an "event" associated with the number of G's in the turn. G's may also be reported for other locations. One difficulty with such measurements is that there may be many larger G forces surfboard 1146 from flips, kicks and other actions; however the invention solves this difficulty by filtering out such actions. In one embodiment, the processor within MMD 1140 monitors the low frequency component of the accelerometer detector to determine the difference in the peaks and troughs of sinusoidal movement, so that MMD 1140 reports wave size and height over time.

One MMD 1140 may also gauge the power of a wave landing on top of the surfer 1142. Such a MMD 1140 preferably includes a pressure detector to determine pressure within water 1144 when a wave lands on surfboard 1146 and on surfer 1142. A "maximum pressure" event is then reported by MMD 1140.

Another MMD 1140 includes an inclinometer or other angle determination detector to determine and report angle of the surfboard 1146; for example a maximum angle is reported for a given run or day.

Data from any particular metric (e.g., g's in a turn, angle of surfboard, pressure under water) provided by MMD 1140 is preferably reported wirelessly to a watch worn by surfer 1142; however such data may also be displayed on a display integrated with surfboard 1146 or directly with sensor 1140, such as shown with an airtime sensor in U.S. Pat. No. 5,960, 380, incorporated herein by reference. In the form of a wristwatch, one MMD of the invention includes a pressure sensor housed in the watch; the MMD watch then reports the maximum pressure events without need of a separate MMD 1140 mounted to surfboard 1146 (or integrated therein).

Figure 66:
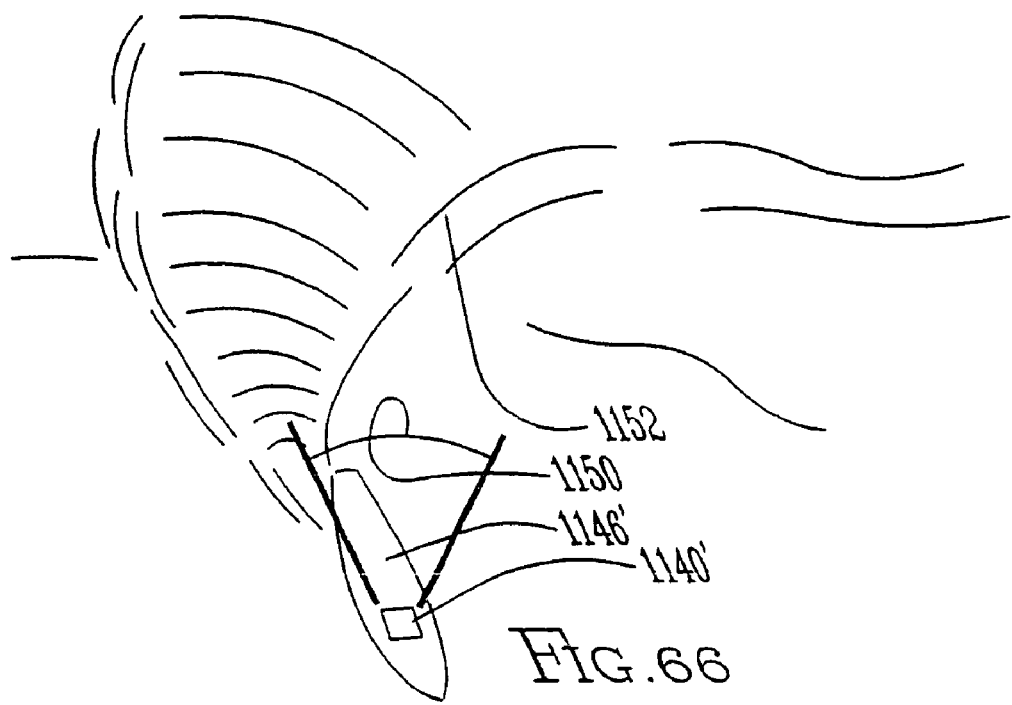
FIG. 66 shows a Green Room surfing event system according to the invention.

In one preferred embodiment, MMD 1140 includes a speed detector (such as a Doppler module or accelerometers as discussed herein or in U.S. Pat. No. 5,960,380) so that surfer speed is reported to surfer 1142. Preferably, in this embodiment, distance traveled is also reported; by way of example the receiver of data from MMD 1140 (e.g., a digital watch) converts speed to distance by multiplying speed by a time duration traveled over that speed. FIG. 66 shows MMD 1140' including a Doppler module that radiates energy 1150, as shown, to determine whether the rider of surfboard 1146' is within the "Green Room"—i.e., within a wave 1152. Preferably, such a MMD 1140' also includes a speed sensor which indicates that board 1146' is in motion so that the time duration of riding within the Green Room is determined accurately.

Figure 67:
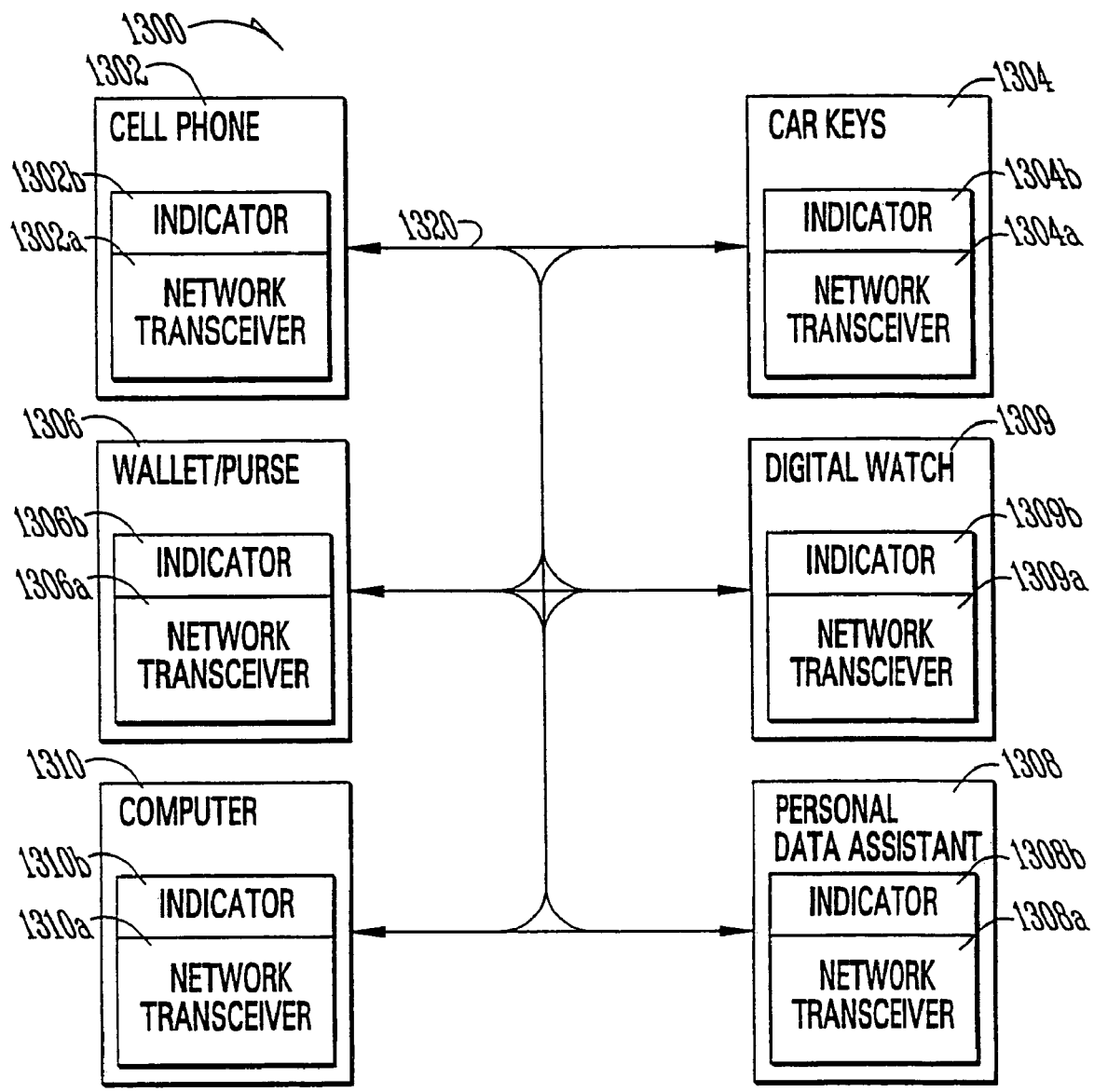
FIG. 67 shows a personal item network constructed according to the invention.

FIG. 67 shows a personal network system 1300 constructed according to the invention. System 1300 keeps track of personal items, such as cell phone 1302, car keys 1304, wallet or purse 1306, personal data assistant 1308, digital watch 1309, and/or personal computer 1310. Additional, fewer or different personal items can be tracked in system 1300, at the selection of a user of system 1300. For example, a user can set up system 1300 to keep track of cell phone 1302 and keys 1304 only. Briefly, each personal item of FIG. 67 includes a network transceiver: cell phone 1302 has transceiver 1302a, car keys 1304 has transceiver 1304a, wallet or purse 1306 has transceiver 1306a, data assistant 1308 has transceiver 1308a, watch 1309 has a transceiver 1309a, and computer 1310 has transceiver 1310a. Each transceiver 1302a, 1304a, 1306a, 1308a, 1309a, 1310a communicates with every other transceiver substantially all the time via a wireless link 1320. Those skilled in the art appreciate that each transceiver 1302a, 1304a, 1306a, 1308a, 1309a, 1310a include an antenna to receive and communicate data on link 1320. In the preferred embodiment, each transceiver 1302a, 1304a, 1306a, 1308a, 1309a, 1310a only maintains communications with any other transceiver over a selected distance, e.g., 100 feet, herein identified as the Network Distance. For example, cell phone transceiver 1302a maintains communications with every other transceiver 1304a, 1306a, 1308a, 1309a, 1310a so long as cell phone 1302 is within the Network Distance of every other device 1304, 1306, 1308, 1309, 1310. However, for example, once cell phone 1302 is separated by keys 1304 by more than the Network Distance, then cell phone 1302 ceases communications with keys 1304 but maintains communications with other items 1306, 1308, 1309, 1310 (assuming items 1306, 1308, 1309, 1310 are within the Network Distance from cell phone 1302).

In one preferred embodiment, each transceiver 1302a, 1304a, 1306a, 1308a, 1309a, 1310a includes a Bluetooth microchip and transceiver known in the art. Bluetooth transceivers only maintain a communication link (at a frequency of about 2.4 GHz in the ISM band) over a short range, e.g., 50 feet, and are not generally suitable for longer communication distances.

Optionally, one or more of transceivers 1302a, 1304a, 1306a, 1308a, 1309a, 1310a are instead transponders; and at least one of items 1302a, 1304a, 1306a, 1308a, 1309a, 1310a provide excitation energy to the transponders to "reflect" data along link 1320 to provide the functionality described herein. Those skilled in the art should appreciate that items 1302a, 1304a, 1306a, 1308a, 1309a, 1310a may incorporate other technology, such as transmitters, to facilitate like functionality. That is, not every item 1302, 1304, 1306, 1308, 1309, 1310 needs to transmit and receive data on link 1320. For example, wallet 1306 can include a transmitter instead of a transceiver to provide data about itself on link 1320; and other items 1302, 1304, 1308, 1309, 1310 can use wallet data to know whether it is in the network or not (even though wallet 1306 does not know whether other items 1302, 1304, 1308, 1309, 1310 are in the network). Transponders can provide like functionality for certain items 1302, 1304, 1306, 1308, 1309, 1310 as a matter of design choice.

Wireless link 1320 includes information about time and items in the network; preferably the information also includes location information. For example, data 1320 informs each item 1302-1310 that every other item is still within the network, and, thus, that one or more items have not moved to beyond the Network Distance. If one item—e.g., keys 1304—leaves the network so that item 1304 no longer communicates on link 1320, every other item 1302, 1306, 1308, 1310 knows that item 1304 is no longer linked and data is stored on every other item 1302, 1306, 1308, 1310 indicating a time when item 1304 left the network. Preferably, the stored data in every other item also includes where the network was when keys 1304 disappeared.

In the simplest embodiment, each of items 1302-1310 includes a corresponding indicator 1302b-1310b; each of indicators 1302b-1310b can for example be a LED, LCD, buzzer or vibrator. When any of items 1301-1310 are "lost" from the network—e.g., one item moves beyond the Network Distance—then the indicator in one or more of the other items tells the user of system 1300 that an item has "left". That person can then expend effort to location the lost item. By way of example, each of indicators 1302b-1310b may provide a beep, sound or vibration to provide the user with knowledge of a lost item 1302-1310.

In a more complex embodiment, data stored on any item 1302-1310 indicating the loss of any item within network 1300 is a "cookie" of information detailing when and where an item left the network. In this way, a user of system 1300 can locate and find the lost item by reviewing cookies in any other item. By way of example, consider a network 1300 made from keys 1304, wallet 1306, digital watch 1309 and cell phone 1302—items commonly carried by a male business person. In the preferred embodiment, this person would designate items 1302, 1304, 1306, 1309 as being "in network" (such as described below in connection with FIG. 68)—and system 1300 thereafter monitors items 1302, 1304, 1306, 1309 so that the person can keep track of items 1302, 1304, 1306, 1309. If for example this person leaves his cell phone 1302 in a restaurant, then items 1304, 1306, 1309 know this occurred and inform him of the time, and preferably the location, of when cell phone 1302 was lost. Thus for example, watch 1309 can light an LED (as indicator 1309b) that an item is lost; item 1304 can indicate (through a LCD indicator 1304b) that cell phone 1302 was lost in cell area corresponding to downtown Boston at 15:15 pm. Specifically, in one embodiment, cell phone 1302 provides "location" information of at least a cell area; and cell phone 1302 provides "time" information by its real time clock (those skilled in the art appreciate that keys 1304, digital watch 1309 or any other item can also include a real time clock as a matter of design choice). Accordingly, link 1320 has location and time information updated to each item 1304, 1306, 1309. In leaving his cell phone at the restaurant, keys 1304, wallet 1306, watch 1309 receive "cookie" deposited in internal memory indicating when and where cell phone 1302 left the network of items 1302, 1304, 1306, 1309. Accordingly, the person reviews data in either of items 1304, 1306, 1309 to learn of where he left his cell phone. Note that if he then lost item 1304, he may also learn something of when item 1304 left the smaller network of items 1304, 1306, 1309 depending upon time and location data available. Those skilled in the art appreciate that cell phone technology enables more precise location information of where a cell phone is; and preferably this information will be provided to network system 1300 so that more precise location information is available to all network items. GPS receiver chips may also be incorporated into any of items 1302-1310 to provide the location information as described herein in connection with system 1300.

Figure 68:
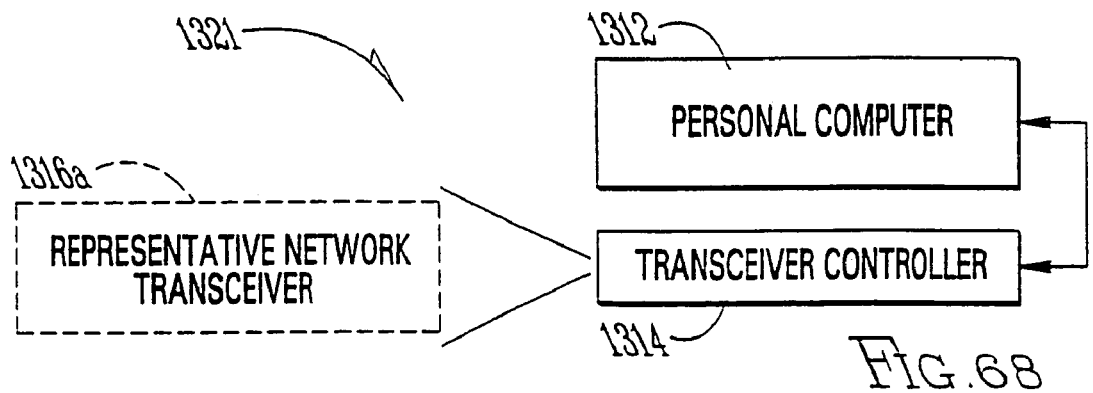
FIG. 68 shows a communications interface between a computer and one of items of FIG. 67.

Users of system 1300 "program" which items are in the network preferably through a personal computer interface, shown in FIG. 68. In FIG. 68, a personal computer 1312 connects with a transceiver controller 1314 to program a network transceiver 1316a (representative of any transceiver 1302a, 13014a, 1306a, 1308a, 1309a, 1310a, for example). Controller 1314 preferably includes a transceiver that wirelessly communications with transceiver 1316a via a data control link 1321. Computer 1312 provides security and ID information so that items networked in system 1300 are secure relative to other users with other networks. By way of example, computer 1312 may provide an password key that is only known and used by items of network 1300; so that other items of other networks does not communicate on link 1320.

Figure 69:
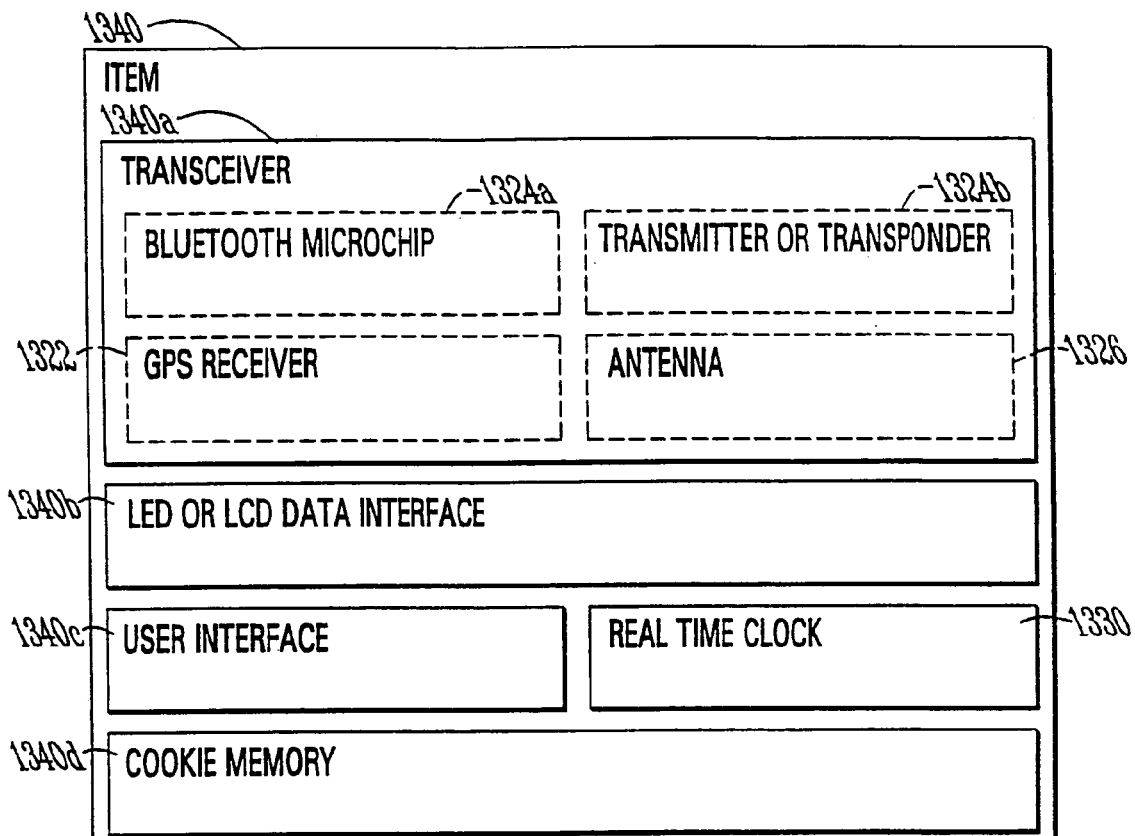
FIG. 69 illustrates electronics for one of the items within the network of FIG. 67.

Note that a "wallet" or "purse" do not generally have electronics associated therewith, to provide the functionality described above. Therefore, in the preferred embodiment, a transceiver 1306a is "attached" to a wallet or purse to provide the underlying electronics. By way of example, such a transceiver takes the form of a credit card inserted into the wallet or purse. FIG. 69 illustrates one non-electronic item 1340, e.g., a wallet 1306, attached to a transceiver 1340a suitable for construction as an attachment like a smart card. Transceiver 1340a can for example include a Bluetooth microchip 1324a or alternatively a transmitter or transponder 1324b. A GPS receiver 1322 can alternatively be included with transceiver 1340a. An antenna 1326, if needed, provides for communication along link 1320, FIG. 67. An LCD or LED data interface provides data and/or warnings to users reviewing item 1340 (and specifically transceiver 1340a). A user interface 1340c permits access to and/or modification of data or functionality of transceiver 1340a. A real time clock 1330 preferably provides time data for time stamping "lost" item information onto network link 1320, so that a user would know when item 1340 (or other items) were lost. In the preferred embodiment, a cookie memory stores "events" associated with lost items—e.g., a cell phone was lost at GPS coordinates X, Y at noon, providing obvious benefit in finding the lost item.

Figure 70:
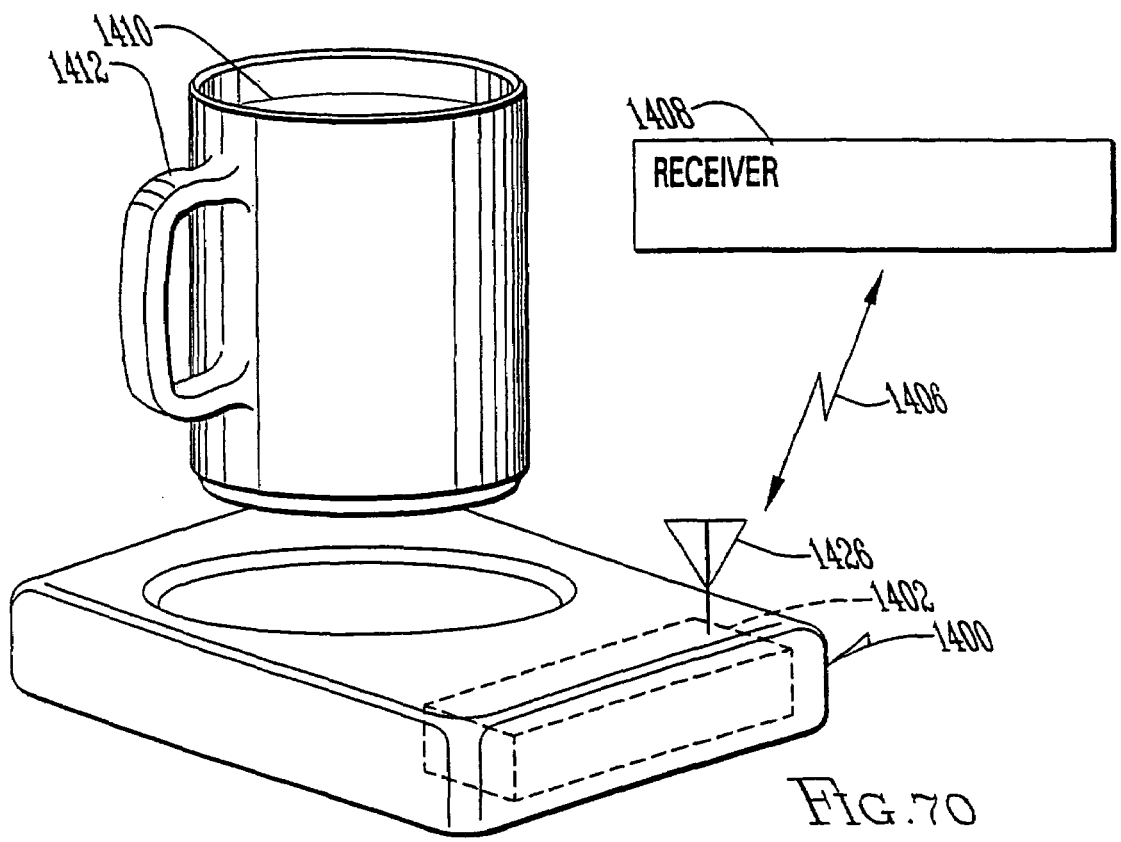
FIG. 70 and FIG. 71 show an electronic drink coaster constructed according to the invention.
Figure 71:
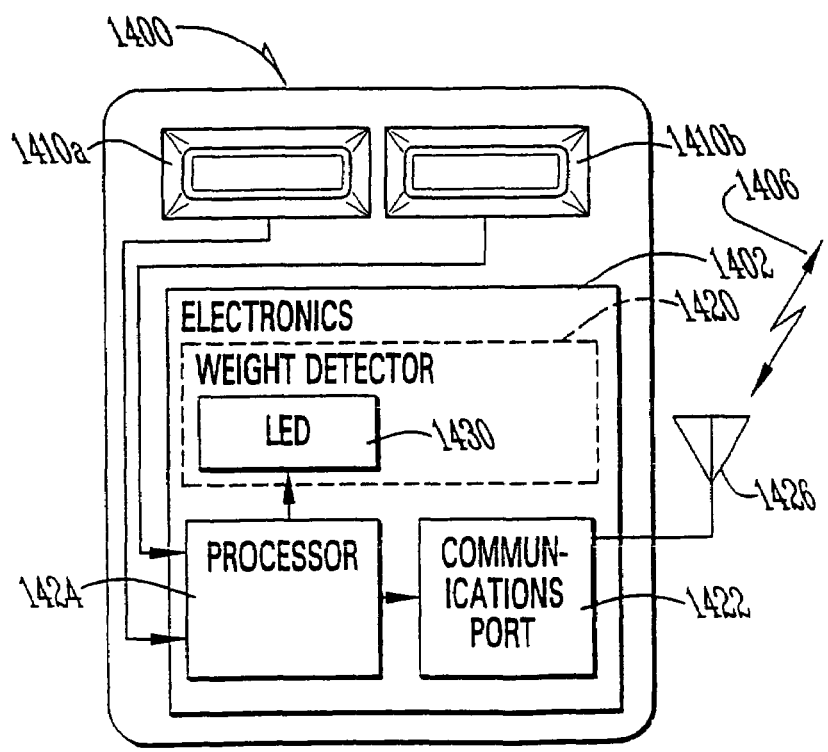

FIG. 70 and FIG. 71 show an electronic drink coaster 1400 constructed according to the invention. Internal electronics 1402 sense the weight of a drink 1404 on coaster 1400 to automatically inform a restaurant or bar, via wireless signals 1406 to a restaurant or bar receiver 1408, that the customer needs a drink or refill. In one embodiment, a customer can also place an order from coaster 1400. Liquid (e.g., beer) 1410 may be used to calibrate electronics 1402 so that electronics 1402 knows when glass 1412 is full or empty, to report the information as data 1406.

FIG. 71 shows a top plan view of coaster 1400, including customer order or calibration buttons 1410a, 1410b. Electronics 1402, typically internal to coaster 1400, include a weight detector 1420, communications port 1422, processor 1424, and antenna 1426; electronics 1402 are similar in design to many of the MMDs or EMDs described herein. Weight detector 1420 detects weight on coaster 1400; and processor 1422 decides how to use the weight information in a meaningful way. By way of example, processor 1422 knows the approximate weight of glass 1412 onto weight detector 1420, and once glass 1412 is filled with beer it also knows when glass 1412 is empty—creating one reporting event to bar receiver 1408, if desired. Users of coaster 1400 can also select inputs to coaster electronics 1402 so as to place orders, wirelessly, to restaurant receiver 1408. For example, a user of coaster 1400 can order "another beer" by pressing button 1410a. Other order functions can of course be included with coaster 1400, including an LED 1430 that provides the status of orders, sent to coaster 1400 via receiver 1408.

Figure 72:
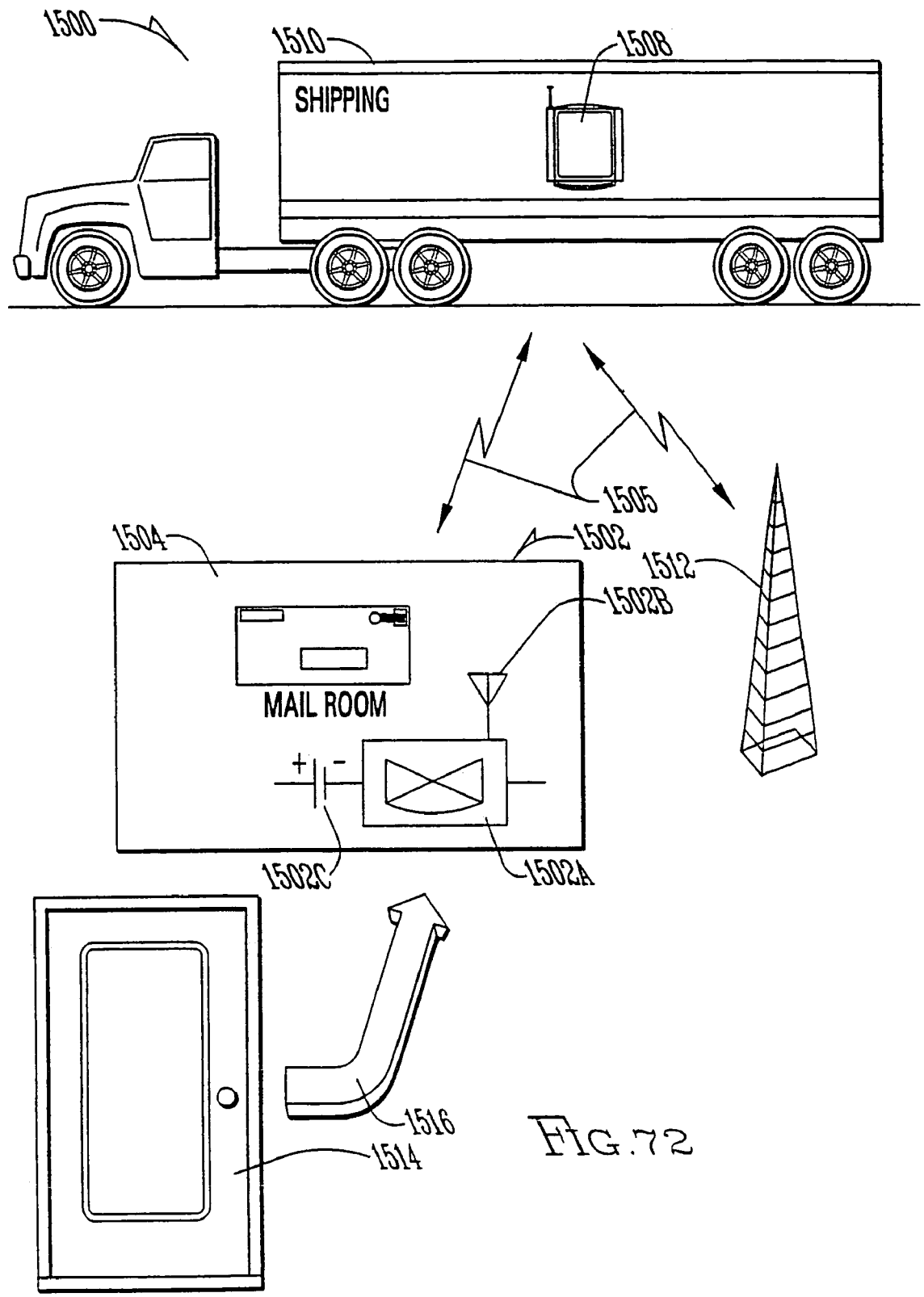
FIG. 72 shows a package management system of the invention.

FIG. 72 shows a package management system 1500, and sensor 1502, of the invention. Sensor 1502 (e.g., a MMD or EMD described herein) may be integrated directly with a shipping label 1504 for attachment to a box or envelope to ship products, goods or other material. Sensor 1502 includes an integrated circuit 1502A, a communications port 1502B and a battery 1502C to communicate data (e.g., impact, temperature, humidity) experienced by label 1504 to external devices. By way of example, a remote receiver 1508 may be used to interrogate or read data from sensor 1502. In the preferred embodiment, sensor 1502 also includes a unique package identifier (e.g., like a bar code) so as to identify label 1504 and the goods associated therewith. A receiver 1508 linked to a transportation channel of label 1504 (e.g., a transportation channel traveled by a shipping truck 1510) may then communicate with sensor 1502, e.g., via wireless link 1505, to determine whether label 1504 is in the correct channel. Accordingly, sensor 1502 helps track label 1504 and may further prevent theft of packages linked to label 1504 since the wireless system may automatically determine inappropriate location of label 1504. A remote wireless relay tower 1512 may communicate with receiver 1508 so as to manage and track label 1504 movement and location during shipment. The invention may augment or even replace manual scanning of labels for shipping packages; the invention may also prevent theft of packages by automatically identifying inappropriate packages in shipment channels.

In the preferred embodiment, a dispenser 1514 may contain several labels similar to label 1504; dispenser preferably issues label 1504 in a manner similar to canister 200, FIG. 10, so as to "power on" label 1504 with an internal time stamp. A location code and/or time code are thus preferably communicated from dispenser 1514 to sensor 1502 when label 1504 issues 1516 from dispenser 1514.

Figure 73:
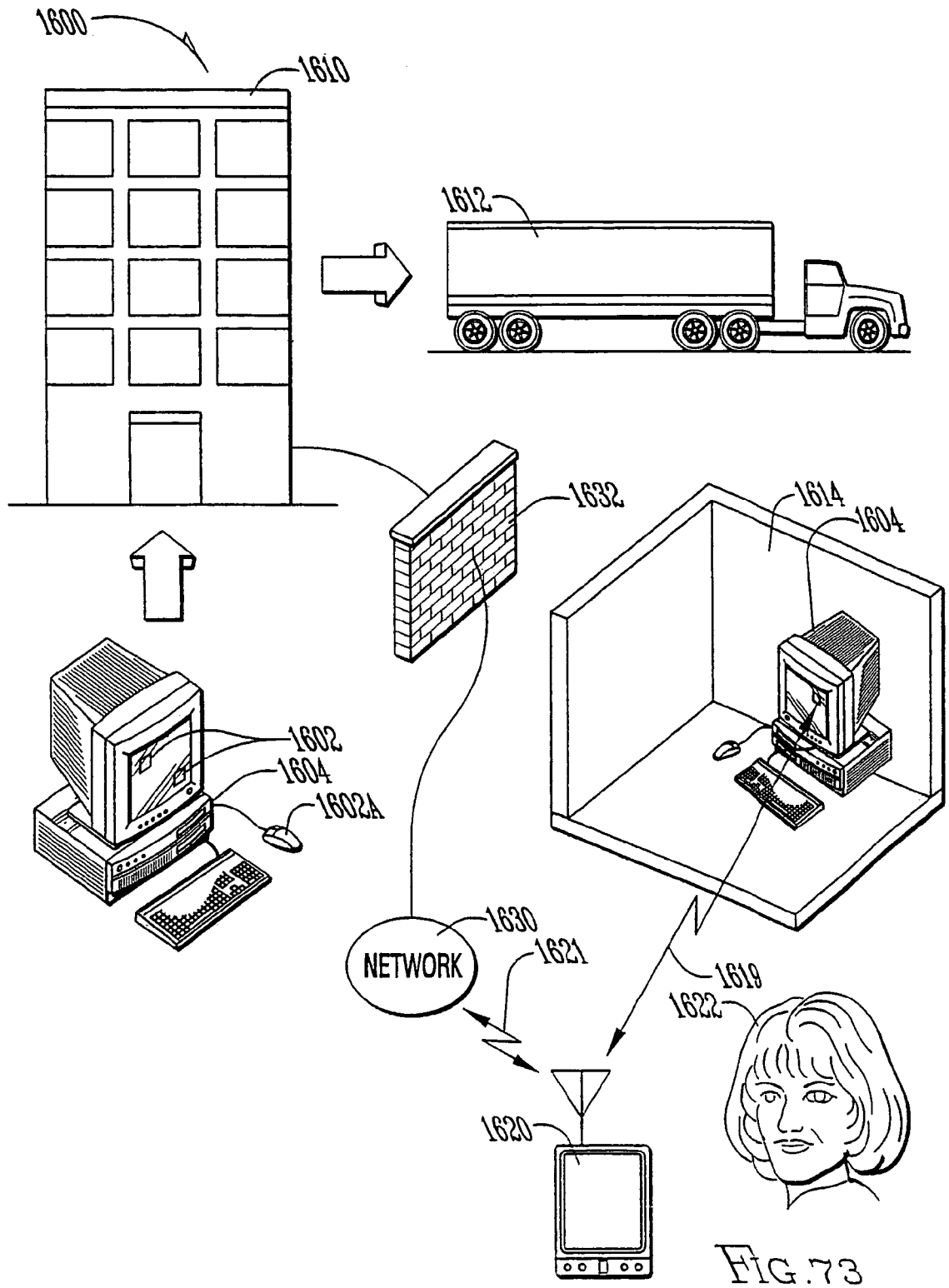
FIG. 73 shows a product integrity tracking system of the invention.

FIG. 73 shows a product integrity tracking system 1600 of the invention. One or more sensors 1602 (e.g., each of the sensors being a MMD or EMD) attach to a customer product 1604. Preferably, sensors 1602 "stick" to product 1604 similar to MMDs or EMDs discussed herein. Product 1604 may be any product of value, including, for example, medical devices, computers, furniture and pharmaceuticals (in the case of pharmaceuticals, sensors 1604 may for example attach to packaging containing the pharmaceuticals, or be arranged adjacent to product 1604, such as indicated by sensor 1602A). Typically, product 1604 initiates shipment along a shipping channel at the customer facility 1610 (e.g., a plant or laboratory). The company of facility 1610 may for example independently attach sensors 1602 to product 1604. A shipping channel may for example include a separate shipping company such as FED EX with a truck 1612. At the conclusion of travel, product 1604 reaches its destination 1614 (e.g., a place controlled by the customer of the company of facility 1610). At destination 1614, sensors 1604 are read through wireless link 1619 by an interrogating device 1620 so as to see how product 1604 fared during travel. The shipping company may have persons 1622 to take the reading or this may occur automatically at destination 1614. Data acquired from sensor 1602 may for example include impact (or "acceleration information") and temperature, each preferably with a time stamp help track event occurrences (e.g., an acceleration event greater than 10 g's at 9:10 AM, Monday). Multiple sensors 1602 provide for detecting event occurrences at different locations on product 1604. This is particularly useful for complex medical devices that may have a relatively sturdy base and a fragile robotic arm, each with different performance specifications (e.g., each with a maximum load allowance); sensors 1602 may thus each attach to separate area of product 1604 so that product integrity information 1619 may be determined for multiple locations. Data from device 1620 may communicate automatically, via link 1621, and back to facility 1610 through network 1630 (e.g., the Internet) and through a firewall 1632 so as to communicate product integrity information, in near real-time, to the company of product 1604. In this way, this company may better manage its brand integrity of product 1604 during shipment. If a damaging event occurred to product 1604, during shipment, that company will learn about it and may ship a replacement product (or move to refurbish product 1604).

What is claimed is:

1. A method for monitoring fractional weight supported by one foot of a person, comprising the steps of:
    adhering a movement monitor device underneath the foot such that the device is compressed when weight is applied to the foot;
    generating wireless signals representative of a fractional weight supported by the foot;
    remotely receiving the wireless signals as information of the fractional weight, and
    informing the person of the fractional weight.

2. The method of claim 1, further comprising utilizing one of a force sensing resistor or electro-resistive element in the movement monitor device, to respond to weight applied to the movement monitor device.

3. The method of claim 1, the step of informing comprising displaying the fractional weight to the person.

4. The method of claim 1, the step of receiving comprising displaying the fractional weight at a watch worn by the person.

5. A method of monitoring weight of a person, comprising the steps of:
    arranging one or more weight sensitive detectors underneath a foot of the person;
    receiving an interrogation signal from a remote receiver;
    responsive to the interrogation signal, processing signals from the detectors to determine weight; and
    wirelessly communicating the weight to the remote receiver.

6. The method of claim 5, further comprising reporting weight information to the person.

7. The method of claim 6, wherein reporting comprises displaying the weight to the person.

8. A method of claim 5, wherein the step of arranging weight sensitive detectors comprises integrating the detectors within a shoe.

9. A method of claim 5, wherein wirelessly communicating comprises communicating the weight as wireless data signals for the remote receiver.

10. A method of claim 1, the fractional weight comprising a target fractional weight of a total weight of the person.

11. A method of claim 1, the movement monitor device selected based upon a total weight of the person.

12. A system of monitoring weight of a person, comprising:
    a shoe and one or more pressure sensors integrated with the shoe;
    a remote receiver for generating a wireless interrogation signal; and
    a processor, responsive to the interrogation signal, for determining weight based on data from the sensors.

13. A system of claim 12, the remote receiver comprising a device selected from the group of a cell phone, an MP3 player, a pager, a watch or a personal data assistant.

14. A method for monitoring fractional weight supported by one foot of a person, comprising the steps of:
    calibrating a movement monitor device to at least one fractional weight of a person's total body weight;

adhering the movement monitor device underneath the person's foot such that the device is compressed when weight is applied to the foot;

generating wireless signals representative of a weight supported by the foot;

comparing the wireless signals with the fractional weight, and informing the person when the supported weight is substantially equal to the fractional weight.

15. A method of claim 14, further comprising the step of wirelessly communicating one or both of the supported weight and the fractional weight to a remote receiver.

16. A method of claim 15, the remote receiver generating a visual indicator when the supported weight is substantially equal to the fractional weight.

17. A method of claim 15, wherein transmitting one or both of the supported weight and the fractional weight to the remote receiver comprises transmitting to a device selected from the group of a cell phone, an MP3 player, a pager, a watch or a personal data assistant.

18. A method of claim 14, further comprising utilizing one of a force sensing resistor or electro-resistive element in the movement monitor device, to respond to weight applied to the movement monitor device.

19. A method of claim 14, further comprising the step of receiving an interrogation signal from a remote receiver; wherein the steps of generating, comparing and informing occur responsive to the interrogation signal.

* * * * *

UNITED STATES PATENT AND TRADEMARK OFFICE
CERTIFICATE OF CORRECTION

PATENT NO. : 7,620,520 B2  Page 1 of 1
APPLICATION NO. : 11/647035
DATED : November 17, 2009
INVENTOR(S) : Curtis A. Vock et al.

It is certified that error appears in the above-identified patent and that said Letters Patent is hereby corrected as shown below:

Column 4, line 13, "then need" should read --the need--;
Column 5, line 63, "function a" should read --function of a--;
Column 9, line 44, "a event" should read --an event--; line 49, "an humidity" should read --a humidity--;
Column 11, line 1, "or sensitive" should read --a sensitive--; line 15, "include" should read --includes--;
  line 46 "then need" should read --the need--; line 51, "batter" should read --battery--;
Column 35, line 36, "analyses" should read --analyzes--;
Column 36, line 13, "user select" should read --user to select--;
Column 38, line 55, "for very" should ready --for a very--;
Column 41, line 55, "Vi" should read --$V_i$--;
Column 44, line 47, "data accord" should read --data in accord--;
Column 47, line 20, "external" should read --externally--;
Column 48, line 56, "one a" should read --once a--;
Column 54, line 59, "200 lbs persons" should read --200 lb persons--;
Column 55, line 63 "into and" should read --into an--;
Column 56, line 50, "can for example be" should read --can be--;
Column 58, line 22, "1131- and" should read --1131 - and--; line 35, "i.e." should read
  --i.e.,--; line 58, "posts" should read --posts.--;
Column 59, line 29 "surfboard 1146" should read --affecting surfboard 1146--;
Column 60, line 33, "by keys" should read --from keys--;
Column 61, line 16, "location" should read --locate--;
Column 62, line 2, "13014*a*" should read --1304*a*--; line 4, "communications" should read
  --communicates--; line 8, "an password" should read --a password--; line 10 "does" should read --do--;
Column 63, line 57, "help" should read --to help--; line 64, "area" should read --areas--;

Signed and Sealed this

Ninth Day of February, 2010

David J. Kappos
*Director of the United States Patent and Trademark Office*